United States Patent
Yoshida

(10) Patent No.: US 8,621,588 B2
(45) Date of Patent: Dec. 31, 2013

(54) INFORMATION PROCESSING SYSTEM, TERMINAL DEVICE, AND SERVER

(75) Inventor: Akitoshi Yoshida, Asahikawa (JP)

(73) Assignee: National University Corporation Asahikawa Medical University, Hokkaido (JP)

(*) Notice: Subject to any disclaimer, the term of this patent is extended or adjusted under 35 U.S.C. 154(b) by 157 days.

(21) Appl. No.: 13/378,426

(22) PCT Filed: Jun. 14, 2010

(86) PCT No.: PCT/JP2010/060027
§ 371 (c)(1),
(2), (4) Date: Jan. 11, 2012

(87) PCT Pub. No.: WO2010/147077
PCT Pub. Date: Dec. 23, 2010

(65) Prior Publication Data
US 2012/0102559 A1    Apr. 26, 2012

(30) Foreign Application Priority Data

Jun. 15, 2009 (JP) .................. 2009-141792
Jun. 15, 2009 (JP) .................. 2009-141793
Jun. 17, 2009 (JP) .................. 2009-144603

(51) Int. Cl.
*G06F 21/31* (2013.01)

(52) U.S. Cl.
USPC .......... 726/7; 726/1; 726/2; 726/3; 726/4; 726/5; 726/6; 713/165; 713/166; 713/167; 713/168

(58) Field of Classification Search
USPC .............. 726/1–7, 26–27; 713/165–168
See application file for complete search history.

(56) References Cited

U.S. PATENT DOCUMENTS 7,174,462 B2 * 2/2007 Pering et al. ............ 713/182
8,020,196 B2 * 9/2011 Randle et al. ............ 726/4
(Continued)

FOREIGN PATENT DOCUMENTS

JP    09-326750 A    12/1997
JP    2001-306518 A    11/2001
(Continued)

OTHER PUBLICATIONS

Office Action from Japanese Patent App. No. 2009-141792 (May 30, 2013) with partial English translation thereof.
(Continued)

*Primary Examiner* — Kambiz Zand
*Assistant Examiner* — Tongoc Tran
(74) *Attorney, Agent, or Firm* — Cermak Nakajima LLP; Tomoko Nakajima

(57) ABSTRACT

With a terminal apparatus that includes an authentication method deciding unit that selects one of two or more authentication methods according to acquired position information, an authentication screen output unit that outputs a screen corresponding to the one authentication method, an accepting unit that accepts authentication information that is input on that screen, an authentication information sending unit that sends an authentication method identifier that identifies an authentication method and the authentication information to a server, an output information receiving unit that receives, from the server, one or more pieces of output information corresponding to the authentication method identification information in the case of success of authentication, and an output information output unit that outputs output information, information necessary for medical practice can be acquired while appropriately securing the privacy of a patient.

9 Claims, 39 Drawing Sheets

(56) References Cited

U.S. PATENT DOCUMENTS

| | | | |
|---|---|---|---|
| 8,229,758 B2* | 7/2012 | Moncrease | 705/2 |
| 2007/0143837 A1* | 6/2007 | Azeez et al. | 726/11 |
| 2007/0223685 A1* | 9/2007 | Boubion et al. | 380/2 |
| 2008/0319794 A1* | 12/2008 | Carlson et al. | 705/3 |
| 2009/0015373 A1* | 1/2009 | Kelly et al. | 340/5.62 |
| 2009/0037224 A1* | 2/2009 | Raduchel | 705/3 |
| 2009/0152343 A1* | 6/2009 | Carter et al. | 235/379 |
| 2009/0189736 A1* | 7/2009 | Hayashi | 340/5.81 |
| 2010/0332404 A1* | 12/2010 | Valin | 705/310 |

FOREIGN PATENT DOCUMENTS

| | | |
|---|---|---|
| JP | 2002-117152 A | 4/2002 |
| JP | 2002-133039 A | 5/2002 |
| JP | 2002-169895 A | 6/2002 |
| JP | 2002-232955 A | 8/2002 |
| JP | 2002-366665 A | 12/2002 |
| JP | 2003-067506 A | 3/2003 |
| JP | 2003-162578 A | 6/2003 |
| JP | 2003-264500 A | 9/2003 |
| JP | 2004-248159 A | 9/2004 |
| JP | 2005-135002 A | 5/2005 |
| JP | 2005-236818 A | 9/2005 |
| JP | 2006-074153 A | 3/2006 |
| JP | 2006-195669 A | 7/2006 |
| JP | 2007-184951 A | 7/2007 |
| JP | 2007-220075 A | 8/2007 |
| JP | 2007-251840 A | 9/2007 |
| JP | 2008-158820 A | 7/2008 |
| JP | 2008-198120 A | 8/2008 |
| JP | 2009-003760 A | 1/2009 |
| JP | 2009-053866 A | 3/2009 |
| JP | 2009-151726 A | 7/2009 |

OTHER PUBLICATIONS

Daiki Mikami et al., "Keitai Denwa ni yoru Anzensei no Takai Riyosha Ninsho ga Kano na Enkaku Iryoyo Tsushin Infrastructure-System no Kaihatsu to Hyoka," Japanese Journal of Telemedicine and Telecare, Oct. 1, 2008, vol. 4, No. 2, pp. 273-274.

International Search Report for PCT Patent App. No. PCT/JP2010/060027 (Aug. 17, 2010).

Office Action issued in Japanese Patent App. No. 2009-141793 (Aug. 2, 2013) with partial English translation.

Office Action issued in Japanese Patent App. No. 2009-144603 (Aug. 2, 2013) with partial English translation.

* cited by examiner

FIG.5

| ID | Region information | Time information | Authentication method identification information |
|---|---|---|---|
| 1 | $(x_1, y_1)\ (x_2, y_2)$ | 9:00 − 18:00 | Method 1 |
| 2 | | 18:01 − 8:59 | Method 2 |
| 3 | Others | — | Method 3 |

FIG.6

| No | First authentication information | | Second authentication information | | Terminal identification information | Output information | | | | | |
|---|---|---|---|---|---|---|---|---|---|---|---|
| | ID1 | PW1 | ID2 | PW2 | | Name | Age | Sex | History of disease | Disease under treatment | Treatment history of cancer | |
| 1 | 5631 | abc | abcd | 371 | 080-1234-5678 | Akiko Tanaka | 48 | female | Appendicitis (age 20) gastric ulcer (age 28) diabetes (age 30 to present) | diabetes | no | ...... |
| 2 | 1221 | xy3 | xyzw | 172 | 080-7788-1234 | Kazuo Yamada | 34 | male | Anemia (age 15) hypertension (age 30) | none | --- | ...... |
| 3 | 7215 | a35 | ppxx | 555 | 080-1222-7753 | Hiroko Yamamoto | 28 | female | Appendicitis (age 25) | stomach cancer gastric ulcer | yes | ...... |
| ...... | ...... | ...... | ...... | ...... | ...... | ...... | ...... | ...... | ...... | ...... | ...... | ...... |

FIG.12

| ID | Region name | Region information |
|---|---|---|
| 1 | Asahikawa | $(x_1, y_1)$ $(x_2, y_2)$ $(x_3, y_3)$ ... ... |
| 2 | Sapporo | $(x_n, y_n)$ $(x_{n+1}, y_{n+1})$ ... ... |
| ⋮ | ⋮ | ⋮ |

FIG.21

| No | First authentication information | | Second authentication information | | Terminal identification information | Output information | | | | | |
|---|---|---|---|---|---|---|---|---|---|---|---|
| | ID1 | PW1 | ID2 | PW2 | | Name | Age | Sex | History of disease | Disease under treatment | Treatment history of cancer | ... |
| 1 | 5631 | abc | abcd | 371 | 090-1234-5678 | Akiko Tanaka | 48 | female | Appendicitis (age 20) gastric ulcer (age 28) diabetes (age 30 to present) | diabetes | no | ...... |
| 2 | 1221 | xy3 | xyzw | 172 | 080-7788-1234 | Kazuo Yamada | 34 | male | Anemia (age 15) hypertension (age 30) | none | — | ...... |
| 3 | 7215 | a35 | ppxx | 555 | 080-1222-7753 | Hiroko Yamamoto | 28 | female | Appendicitis (age 25) | stomach cancer gastric ulcer | yes | ...... |
| ...... | ...... | ...... | ...... | ...... | ...... | ...... | ...... | ...... | ...... | ...... | ...... | ...... |

FIG.22

| Condition information | | | Information that is not output |
|---|---|---|---|
| Authentication method identification information | Position information | Medical procedure information | |
| Method 1 | Unregistered place | Normal | "History of disease" "Disease under treatment" = stomach cancer "Treatment history of cancer" |
| | | Emergency | "Treatment history of cancer" |
| | Registered place | Patient's doctor | ———— |
| | | Not patient's doctor | "History of disease" "Treatment history of cancer" |
| Method 2 | Unregistered place | Normal | "History of disease" "Treatment history of cancer" |
| | | Emergency | "Treatment history of cancer" |
| | Registered place | ———— | ———— |
| Method 3 | ———— | ———— | ———— |

FIG.23

| ID | User ID | Registered place | | ID of patient's doctor |
|---|---|---|---|---|
| 1 | 5631 | $(x_1, y_1)$  $(x_2, y_2)$ | | 236100 |
| | | $(x_3, y_3)$  $(x_4, y_4)$ | | |
| 2 | 1221 | $(x_5, y_5)$ | $(x_6, y_6)$ | 287007 |
| 3 | 7215 | $(x_7, y_7)$ | $(x_8, y_8)$ | 198325 |
| ⋮ | ⋮ | ⋮ | | ⋮ |

FIG.33

| Terminal identification information | Output information | | | | | |
|---|---|---|---|---|---|---|
| | Name | Age | Sex | History of disease | Disease under treatment | Treatment history of cancer | ⋯ |
| 080-1234-5678 | Akiko Tanaka | 48 | female | Appendicitis (age 20) gastric ulcer (age 28) diabetes (age 30 to present) | diabetes | no | ⋯ |
| 080-7788-1234 | Kazuo Yamada | 34 | male | Anemia (age 15) hypertension (age 30) | none | — | ⋯ |
| 080-1222-7753 | Hiroko Yamamoto | 28 | female | Appendicitis (age 25) | stomach cancer gastric ulcer | yes | ⋯ |
| ⋯ | ⋯ | ⋯ | ⋯ | ⋯ | ⋯ | ⋯ | ⋯ |

FIG.34

| Attribute name | Attribute value | Flag |
|---|---|---|
| Disease under treatment | Lung cancer | 1 |
| Treatment history of cancer | — | 1 |
| ⋮ | ⋮ | ⋮ |

INFORMATION PROCESSING SYSTEM, TERMINAL DEVICE, AND SERVER

This application is a national phase entry under 35 U.S.C. §371 of PCT Patent Application No. PCT/JP2010/060027, filed on Jun. 14, 2010, which claims priority under 35 U.S.C. §119 to Japanese Patent Application Nos. 2009-141792, filed Jun. 15, 2009, 2009-141793, filed Jun. 15, 2009, and 2009-144603, filed Jun. 17, 2009, all of which are incorporated by reference.

TECHNICAL FIELD

The present invention relates to, for example, an information processing system and the like that handle highly confidential information such as an electronic medical record.

BACKGROUND ART

Conventionally, there has been an application distribution system that performs access control by setting the access right based on user information and position information when download, update or downgrade of an application is performed (see Patent Document 1). In this system, it is possible to change the access right of the same user for the same application according to the place of use.

Also, conventionally, there has been a technique in which authentication using a password is combined with authentication using the position information of a portable terminal (see Patent Document 2).

Also, conventionally, there has been a medical information management system which enables sharing medical information securely by a plurality of medical institutions or other institutions, without requiring a patient to carry a means used only for extracting his or her medical information such as an IC card (see Patent Document 3). Note that it is possible with this system to securely and easily manage medical information in an integrated manner. It is also possible with this system to prevent recording of erroneous medical information, since a patient can check his or her own medical information that is recorded.

Also, conventionally, there has been a health management system in which a variety of personal data and medical data are converted to electronic data to be stored in a database, such that efficient medical practices may be promoted due to sharing of information (see Patent Document 4). In this system, it is possible to protect personal data, which relates to the privacy, by setting the access right to each terminal and performing personal identification. In addition, in this system, since an emergency report mode is provided in a user terminal, it is possible to take an appropriate and prompt action in emergency situations.

Also, conventionally, there has been a medical/health information shared use technique in which medical and health information of an individual is registered in a data management center in addition to information of his or her electronic medical record, thereby promoting effective use of necessary information while limiting the contents disclosed according to the access right of the user (see Patent Document 5).

Also, conventionally, there has been a medical support system that performs electronic medical record management, order management, work schedule management and the like by means of a portable terminal usable inside and outside a medical facility and having a voice call function, a data communication function, a hands-free function, a personal authentication function and the like (see Patent Document 6).

Also, conventionally, there has been an authentication system that provides an authentication technique that is useful for proving that an object existed in a certain place at a certain time (e.g., see Patent Document 7).

Also, conventionally, there has been a telemedicine network system that efficiently provides a service close to a medical service provided in Japan mainly to a traveler during overseas travel (e.g., see Patent Document 8).

Furthermore, conventionally, there has been a medical information providing service system with which an appropriate medical procedure can be performed promptly in a medical setting by providing a user (e.g., medical facilities and doctors) with medical information of an urgent patient or the like that is obtained based on the identification information of the patient (the address, name, mobile phone number, driver's license number, ID number, photo, fingerprint, and the like) (e.g., see Patent Document 9).

[Patent Document 1] JP 2005-135002A
[Patent Document 2] JP 2002-232955A
[Patent Document 3] JP 2002-366665A
[Patent Document 4] JP 2002-169895A
[Patent Document 5] JP 2003-67506A
[Patent Document 6] JP 2006-195669A
[Patent Document 7] JP 2009-3760A
[Patent Document 8] JP 2002-117152A
[Patent Document 9] JP 2008-158820A

DISCLOSURE OF INVENTION

Problem to be Solved by the Invention

However, there has been no conventional technique that, for example, performs authentication by using different authentication methods that have different authentication levels according to the position of the terminal of a patient or a doctor (e.g., according to whether the place is the hospital that the patient usually visits), and that can thereby cause different output information (e.g., medical record information) to be downloaded to the terminal according to the authentication method. Therefore, it has been impossible with conventional techniques to appropriately provide information necessary for the medical practice, while appropriately securing the privacy of the patient.

Also, it has been impossible with conventional techniques to change the authentication method (authentication level) according to the position of the user.

Also, it has been impossible with conventional techniques to change information to be output according to the authentication method. Therefore, for example, it has been impossible to perform an appropriate medical procedure while appropriately securing the privacy of the patient.

Furthermore, it has been impossible with conventional techniques to acquire necessary information from a server in an environment where communication is impossible. That is, for example, when a holder of a terminal apparatus has suddenly become ill in the mountains where communication with the server is impossible, information of that holder (user) cannot be obtained. Thus, it has been impossible to perform an appropriate medical procedure promptly even if a doctor has arrived at the location of the user.

Means for Solving the Problems

A first aspect of the present invention is directed to an information processing system including a terminal apparatus and a server, wherein the terminal apparatus includes: a position information acquiring unit that acquires position information that indicates a current position of the terminal apparatus; an authentication method deciding unit that selects one of two or more authentication methods according to the position information acquired by the position information acquiring unit; an authentication screen output unit that outputs a screen that corresponds to the one authentication method selected by the authentication method deciding unit; an accepting unit that accepts authentication information that is input by a user on the screen output by the authentication screen output unit; an authentication information sending unit that sends, to the server, an authentication method identifier that identifies the authentication method selected by the authentication method deciding unit and the authentication information accepted by the accepting unit; an output information receiving unit that receives, in a case where an execution result of an authentication unit of the server is success of authentication, from the server, one or more pieces of output information corresponding to the authentication method identification information; and an output information output unit that outputs the output information, and the server includes: an information storage unit in which two or more pieces of output information that is information to be output are each stored in association with at least one of two or more different authentication methods; an authentication information receiving unit that receives, from the terminal apparatus, the authentication method identification information and the authentication information; an authentication unit that performs authentication processing by executing, by using the authentication information received by the authentication information receiving unit, one of the two or more different authentication methods that is identified by the authentication method identification information received by the authentication information receiving unit; an information acquiring unit that acquires, in a case where an execution result of the authentication unit is success of authentication, one or more pieces of output information corresponding to the authentication method identification information; and an information sending unit that sends the output information acquired by the information acquiring unit to the terminal apparatus.

With such a configuration, it is possible to acquire information necessary for medical practice while appropriately securing the privacy of the patient, for example.

A second aspect of the present invention is directed to, with respect to the first aspect of the present invention, an information processing system wherein the terminal apparatus further includes: a terminal identification information storage unit in which terminal identification information can be stored; an output information storage unit in which output information can be stored; a non-communication environment detection unit that detects movement to an environment where communication with the server is impossible; and a sending instruction sending unit that sends, in a case where the non-communication environment detection unit has detected movement to an environment where communication with the server is impossible, a sending instruction including the terminal identification information to the server, the output information receiving unit receives output information from the server in response to sending of the sending instruction, the output information output unit accumulates the output information received by the output information receiving unit in the output information storage unit, the information storage unit of the server has stored therein two or more pieces of output information in association with at least one of the two or more different authentication methods, and has stored therein terminal identification information that identifies the terminal apparatus and output information associated with each other, the server further includes a sending instruction receiving unit that receives, from a terminal apparatus, a sending instruction that includes terminal identification information that identifies that terminal apparatus and that is an instruction to send output information, and in a case where the sending instruction receiving unit has received a sending instruction, the information acquiring unit acquires, from the information storage unit, output information that is paired with the terminal identification information included in that sending instruction.

With such a configuration, for example, even in the case where a patient has suddenly become ill in a place where communication with the server is impossible, such as in the mountains, it is possible to download the patient's information in advance such that appropriate medical procedure can be promptly performed.

A third aspect of the present invention is directed to, with respect to the first aspect of the present invention, an information processing system wherein the output information is associated with at least one authentication method and position information that indicates a position, the server further includes a terminal position information receiving unit that receives position information that indicates a position of the terminal apparatus from the terminal apparatus, and in a case where the execution result of the authentication unit is success of authentication, the information acquiring unit acquires one or more pieces of output information corresponding to the authentication method identification information and the position information.

With such a configuration, since output information that can be downloaded to a terminal (e.g., medical record information) differs according to the authentication method and the position of the terminal, it is possible to appropriately acquire information necessary for medical practice while further appropriately securing the privacy of the patient, for example.

Also, a fourth aspect of the present invention is directed to a terminal apparatus that includes: a position information acquiring unit that acquires position information that indicates a current position of the terminal apparatus; an authentication method deciding unit that selects one of two or more authentication methods according to the position information acquired by the position information acquiring unit; an authentication screen output unit that outputs a screen that corresponds to the one authentication method selected by the authentication method deciding unit; an accepting unit that accepts authentication information that is input by a user on the screen output by the authentication screen output unit; an authentication result accepting unit that accepts an authentication result, which is a result of authentication processing performed by using the authentication information; and an authentication result output unit that outputs the authentication result.

With such a configuration, it is possible to change the authentication method according to the position of the user. Accordingly, for example, a simple authentication method is employed in a place where the user is usually present or is usually expected to be present such that simple and prompt authentication is possible, and a strict authentication method is employed in a place where the user does not usually visit such that high-level security can be achieved.

Also, a fifth aspect of the present invention is directed to, with respect to the fourth aspect of the present invention, a terminal apparatus wherein the authentication method deciding unit includes: a region information storage section in which one or more pieces of region information each of which indicates a region can be stored; a determination section that determines whether the position that is indicated by the position information acquired by the position information acquiring unit is included in any of one or more regions that are indicated by the one or more pieces of region information stored in the region information storage section; and an authentication method deciding section that selects one of the two or more authentication methods in a case where the determination section has determined that the position indicated by the position information is included in any of the one or more regions.

With such a configuration, by registering a place where the user is usually present or is usually expected to be present, a simple authentication method is employed in such a place such that simple and prompt authentication is possible, and a strict authentication method is employed in a place where the user does not usually visit such that high-level security can be achieved.

Also, a sixth aspect of the present invention is directed to, with respect to the fifth aspect of the present invention, a terminal apparatus wherein the two or more authentication methods include a first authentication method and a second authentication method having a security level that is higher than that of the first authentication method, and in a case where the determination section has determined that the position indicated by the position information is included in any of the one or more regions, the authentication method deciding section selects the first authentication method from among the two or more authentication methods, and in a case where the determination section has determined that the position indicated by the position information is included in none of the one or more regions, the authentication method deciding section selects the second authentication method from among the two or more authentication methods.

With such a configuration, by registering a place where the user is usually present or is usually expected to be present, a simple authentication method is employed in such a place such that simple and prompt authentication is possible, and a strict authentication method is employed in a place where the user does not usually visit such that high-level security can be achieved.

Also, a seventh aspect of the present invention is directed to, with respect to the sixth aspect of the present invention, a terminal apparatus wherein the region information storage section has stored therein two or more pieces of region authentication information, each piece associating region information with authentication method identification information that identifies the authentication method corresponding to that region information, the determination section determines a region where the position that is indicated by the position information acquired by the position information acquiring unit is included by using the one or more pieces of region information stored in the region information storage section, and the authentication method deciding section acquires, from the region information storage section, the authentication method identification information that is associated with the region information corresponding to the region determined by the determination section.

With such a configuration, in the case where the region is divided into three or more groups, three or more authentication methods suitable for the groups can be employed.

Also, an eighth aspect of the present invention is directed to, with respect to the fifth aspect of the present invention, a terminal apparatus wherein the two or more authentication methods includes a first authentication method and a second authentication method in which authentication processing is not performed, and in a case where the determination section has determined that the position indicated by the position information is included in any of the one or more regions, the authentication method deciding section selects the second authentication method in which authentication processing is not performed, and in a case where the determination section has determined that the position indicated by the position information is included in none of the one or more regions, the authentication method deciding section selects the first authentication method from among the two or more authentication methods.

With such a configuration, it is possible to cause authentication processing to be performed only when the user is present in a specific place.

Also, a ninth aspect of the present invention is directed to an information processing system including a terminal apparatus and a server, wherein the terminal apparatus further includes: an authentication information sending unit that sends authentication information accepted by the accepting unit to the server; an authentication result receiving unit that receives an authentication result that is a result of authentication processing performed by the server; and a processing unit that performs a predetermined processing only in the case where the authentication result is success of authentication, and the server includes: an authentication information receiving unit that receives authentication information; an authentication unit that performs authentication processing by using the authentication information received by the authentication information receiving unit and acquires an authentication result; and an authentication result sending unit that sends the authentication result acquired by the authentication unit to the terminal apparatus.

With such a configuration, it is possible in the information processing system to change the authentication method according to the position of the user. Therefore, for example, a simple authentication method is employed in a place where the user is usually present or is usually expected to be present such that simple and prompt authentication is possible, and a strict authentication method is employed in a place where the user does not usually visit such that high-level security can be achieved.

Also, a tenth aspect of the present invention is directed to an information processing system including a first terminal apparatus (which may be also referred to as a terminal apparatus), a second terminal apparatus (which may be also referred to as a second terminal), and a server, wherein the first terminal apparatus includes: a first position information storage unit in which first position information that indicates a position of the first terminal apparatus can be stored; a first sending unit that sends the first position information to the server; a first receiving unit that receives an authentication result from the server; and a first output unit that outputs the authentication result, the second terminal apparatus includes: a second position information acquiring unit that acquires second position information that indicates a position of the second terminal apparatus; and a second sending unit that sends the second position information to the server, and the server includes: a first position information receiving unit that receives the first position information from the first terminal apparatus; a second position information receiving unit that receives the second position information from the second terminal apparatus; an authentication unit that determines whether the first position information and the second position information have a predetermined relation, and that acquires, if both information pieces have the predetermined relation, an authentication result indicating success of authentication, and if not, acquires an authentication result indicating failure of authentication, and an authentication result sending unit that sends the authentication result acquired by the authentication unit to the first terminal apparatus.

With such a configuration, for example, in the case where the second terminal apparatus held by the user is present near the first terminal apparatus installed in a hospital or the like (for example, the terminals are in the same room), the authentication result is success of authentication, and information can be downloaded to the first terminal apparatus.

Also, an eleventh aspect of the present invention is directed to a server that includes: an information storage unit in which two or more pieces of output information that is information to be output are each stored in association with at least one of two or more different authentication methods; an authentication information receiving unit that receives, from the terminal apparatus, authentication information used in authentication processing and authentication method identification information that identifies the authentication method; an authentication unit that performs authentication processing by executing, by using the authentication information received by the authentication information receiving unit, one of the two or more different authentication methods that is identified by the authentication method identification information received by the authentication information receiving unit; an information acquiring unit that acquires, in a case where an execution result of the authentication unit is success of authentication, one or more pieces of output information corresponding to the authentication method identification information; and an information sending unit that sends the output information acquired by the information acquiring unit to the terminal apparatus.

With such a configuration, it is possible to change information to be output according to the authentication method.

Also, a twelfth aspect of the present invention is directed to, with respect to the eleventh aspect of the present invention, a server wherein the output information is associated with at least one authentication method and position information that indicates a position, and the server further includes a terminal position information receiving unit that receives position information that indicates a position of the terminal apparatus from the terminal apparatus, and in a case where the execution result of the authentication unit is success of authentication, the information acquiring unit acquires one or more pieces of output information corresponding to the authentication method identification information and the position information.

With such a configuration, it is possible to change information to be output according to the authentication method and the position information.

Also, a thirteenth aspect of the present invention is directed to, with respect to the eleventh aspect of the present invention, a server wherein the output information is medical record information that includes information that identifies a patient and medical history of the patient, and is associated with at least one authentication method, a doctor identifier that identifies a doctor, and emergency information that indicates an emergency level for performing medical procedure, the server further includes a medical procedure information receiving unit that receives, from the terminal apparatus, medical procedure information that includes the doctor identifier or the emergency information that indicates an emergency level for performing medical procedure, and in a case where the execution result of the authentication unit is success of authentication, the information acquiring unit acquires one or more pieces of output information corresponding to the authentication method identification information and the medical procedure information.

With such a configuration, it is possible to change information to be output according to the authentication method and the medical procedure information.

Also, a fourteenth aspect of the present invention is directed to, with respect to the eleventh aspect of the present invention, a server wherein the output information is medical record information that includes information that identifies a patient and medical history of the patient, and is associated with at least one authentication method, a doctor identifier that identifies a doctor, and emergency information that indicates an emergency level for performing medical procedure, the server further includes: a terminal position information receiving unit that receives position information that indicates a position of the terminal apparatus from the terminal apparatus; a medical procedure information receiving unit that receives, from the terminal apparatus, medical procedure information that includes the doctor identifier or the emergency information indicating an emergency level for performing medical procedure; or the terminal position information receiving unit and the medical procedure information receiving unit, and the information acquiring unit acquires one or more pieces of output information that correspond to one or more of the authentication method identification information, and the position information or the medical procedure information, in a case where the execution result of the authentication unit is success of authentication.

With such a configuration, it is possible to change information to be output according to the authentication method as well as the position information and/or the medical procedure information.

Also, a fifteenth aspect of the present invention is directed to an information processing system including a server and a terminal apparatus, wherein the server includes: a terminal information storage unit in which one or more pieces of terminal information in each of which terminal identification information that identifies a terminal apparatus is associated with output information that is information to be sent to the terminal apparatus can be stored; a sending instruction receiving unit that receives, from the terminal apparatus, a sending instruction that includes the terminal identification information that identifies a terminal apparatus and that is an instruction to send output information; an output information acquiring unit that acquires, in a case where the sending instruction receiving unit has received a sending instruction, from the terminal information storage unit, output information that is paired with terminal identification information included in the sending instruction; and an output information sending unit that sends the output information acquired by the output information acquiring unit to the terminal device, and the terminal apparatus includes: a terminal identification information storage unit in which the terminal identification information can be stored; an output information storage unit in which output information can be stored; a non-communication environment detection unit that detects movement to an environment where communication with the server is impossible; a sending instruction sending unit that sends, to the server, an sending instruction including the terminal identification information in a case where the non-communication environment detection unit has detected movement to an environment where communication with the server is impossible; an output information receiving unit that receives output information from the server in response to sending of the sending instruction; an output information storage unit that accumulates the output information received by the output information receiving unit in the output information storage unit; and an output information output unit that outputs the output information accumulated in the output information storage unit.

With such a configuration, it is possible to acquire information in advance even in the case where transition is made to an environment where communication is impossible.

Also, a sixteenth aspect of the present invention is directed to, with respect to the fifteenth aspect of the present invention, an information processing system wherein the non-communication environment detection unit acquires a radio wave reception level, and in a case where the non-communication environment detection unit has detected that a state in which the acquire reception level is less than a predetermined threshold has continued for a period of time that is longer than a predetermined threshold, it detects movement to an environment where communication with the server is impossible.

With such a configuration, it is possible to acquire information in advance even in the case where transition is made to an environment where communication is impossible due to a low radio wave reception level.

Also, a seventeenth aspect of the present invention is directed to, with respect to the fifteenth aspect of the present invention, an information processing system wherein the non-communication environment detection unit includes: a region information storage section in which region information that specifies a region where communication is or will be impossible, or a region where communication is possible is stored; a position information acquiring section that acquires position information that indicates a position of the terminal apparatus; and a non-communication environment detection section that applies the position information to the region information and detects movement to an environment where communication with the server is impossible.

With such a configuration, it is possible to acquire information in advance even in the case where transition is made to an environment where communication is impossible.

Also, an eighteenth aspect of the present invention is directed to, with respect to the fifteenth aspect of the present invention, an information processing system wherein the non-communication environment detection unit receives information indicating movement to an environment where communication with the server is impossible by a close-range wireless communication means, and detects movement to an environment where communication with the server is impossible upon receipt of the information.

With such a configuration, it is possible to acquire information in advance even in the case where transition is made to an environment where communication is impossible.

Also, a nineteenth aspect of the present invention is directed to, with respect to any of the fifteenth to the eighteenth aspects of the present invention, an information processing system wherein the terminal apparatus further includes: a communication environment detection unit that detects that movement to an environment where communication with the server is possible has been made; and an output information deletion unit that deletes output information stored in the output information storage unit in the case where the communication environment detection unit has detected that movement to the environment where communication with the server is possible has been made.

With such a configuration, it is possible to delete output information in the case where movement has been made from an environment where communication with the server is impossible to an environment where communication with the server is possible. Therefore, for example, it is possible to readily secure personal privacy and confidentiality.

Also, a twentieth aspect of the present invention is directed to, with respect to any of the fifteenth to the nineteenth aspects of the present invention, an information processing system wherein the terminal apparatus further includes an accepting unit that accepts an input of an output instruction, the sending instruction sending unit includes: a sending instruction configuring section that configures a sending instruction that includes the terminal identification information and type information that indicates whether the sending instruction is a sending instruction that is sent in a case where the non-communication environment detection unit has detected movement to an environment where communication with the server is impossible, or a sending instruction that is sent in a case where the accepting unit has accepted an output instruction; and a sending instruction sending section that sends the sending instruction configured by the sending instruction configuring section to the server, and the terminal information storage unit has stored therein one or more pieces of terminal information in each of which terminal identification information that identifies a terminal apparatus, output information that is to be sent to the terminal apparatus, and a flag that indicates whether the output information is extracted if information included in the sending instruction is non-communication environment information, or if information included in the sending instruction is output instruction acceptance information are associated with each other, and the output information acquiring unit acquires, in a case where the sending instruction receiving unit has received a sending instruction, from the terminal information storage unit, output information that is paired with the terminal identification information included in the sending instruction and that is paired with the flag corresponding to the type information included in the sending instruction.

With such a configuration, it is possible to acquire information in advance even in the case where transition is made to an environment where communication is impossible.

Also, a twenty-first aspect of the present invention is directed to, with respect to any of the fifteenth to the twentieth aspects of the present invention, an information processing system wherein output information is medical record information that includes information related to diseases of the patient.

With such a configuration, for example, in the case where a holder of a terminal apparatus has suddenly become ill in a place where communication with the server is impossible, such as in the mountains, medical record information of the user can be obtained, thereby providing an environment where appropriate medical procedure can be promptly performed.

Effect of the Invention

With the information processing system of the present invention, for example, it is possible to appropriately provide necessary information, while appropriately securing personal privacy.

BEST MODE FOR CARRYING OUT THE INVENTION

Hereinafter, embodiments of an information processing system and the like will be described with reference to the drawings. Note that elements assigned the same reference numerals in the embodiments perform the same operations, and thus such elements may not be repetitively described.

Embodiment 1

In the present embodiment, an information processing system 1 that acquires position information and changes the authentication method according to the position information will be described. Also, an information processing system 1 that changes the authentication method also according to the time (time period) will be described in the present embodiment.

FIG. 1 is a conceptual diagram of the information processing system 1 of the present embodiment. The information processing system 1 includes a terminal apparatus 11, a second terminal 12 and a server 13. The terminal apparatus 11 and the second terminal 12 are, for example, a so-called personal computer and a portable terminal (including a mobile phone), respectively. The server 13 is a device that is capable of communication with the terminal apparatus 11 and the second terminal 12, and that performs authentication processing. Note that the second terminal 12 is not essential for the information processing system 1. Specifically, the information processing system 1 may be configured by the terminal apparatus 11 and the server 13.

FIG. 2 is a block diagram of the information processing system 1 of the present embodiment.

The terminal apparatus 11 includes an accepting unit 111, a position information acquiring unit 112, an authentication method deciding unit 113, an authentication screen output unit 114, an authentication information sending unit 115, an authentication result accepting unit 116, an authentication result output unit 117, and a processing unit 118.

The authentication method deciding unit 113 includes a region information storage section 1131, a determination section 1132, and an authentication method deciding section 1133.

The second terminal 12 includes a second accepting unit 121, a second sending and receiving unit 122, and a second output unit 123.

The server 13 includes a data storage unit 131, an authentication information receiving unit 132, an authentication unit 133, an authentication result sending unit 134, and a data sending and receiving unit 135.

The authentication unit 133 includes a first authentication section 1331, a second authentication section 1332, and a third authentication section 1333. Note that the authentication unit 133 may include only two authentication sections, or may include four or more authentication sections.

The accepting unit 111 accepts an input from a user. The accepting unit 111 accepts an input of a command to execute processing that requires authentication processing. The command is, for example, a command to log into the server 13 or a command to access the server 13. The accepting unit 111 accepts, for example, authentication information. The authentication information is information that is input on a screen output by the authentication screen output unit 114. The authentication information is necessary for authentication processing. The authentication information is normally input by a user. The authentication information is, for example, a user ID and a password. Also, the authentication information may include two IDs, for example.

The authentication information and the like may be input by any means such as a keyboard, a mouse, a numerical keypad, and a menu screen. The accepting unit 111 can be realized by a device driver of the input means such as a keyboard, menu screen control software, or the like.

The position information acquiring unit 112 acquires position information that indicates the current position of the terminal apparatus 11. The position information is, for example, information of (latitude, longitude). Also, the position information is, for example, information that specifies a place (e.g., address, place names, and the like). The position information acquiring unit 112 is, for example, a GPS receiver. Also, the position information acquiring unit 112 may acquire the position information according to the radio wave reception state from three base stations of the mobile phone, for example. Also, the position information acquiring unit 112 receives information that specifies a place by a close-range wireless communication means, for example.

The authentication method deciding unit 113 selects one of two or more authentication methods according to the position information acquired by the position information acquiring unit 112. The authentication method deciding unit 113 may select one of two or more authentication methods according to the position information acquired by the position information acquiring unit 112 and time. The authentication method deciding unit 113 may select one of two or more authentication methods according to time only. In the case where time is used, the authentication method deciding unit 113 acquires time from a clock held therein or from an external server (e.g., NTP server). Note that a time acquiring unit (not shown) may acquire the current time. Time referred to herein may be information of a time period (e.g., from 9:00 to 19:00, from 22:00 to 8:00, and the like). In addition, decision of the authentication method refers to acquiring authentication method identification information, which is information that identifies the authentication method. Decision of the authentication method also refers to control for transitioning to one of a plurality of processes for realizing an authentication method. The authentication method refers to a method for authenticating the terminal apparatus 11, a method for authenticating a user of the terminal apparatus 11, and the like. The plurality of authentication methods may include a method in which authentication processing is not performed. The authentication method deciding unit 113 can be generally realized by an MPU, memory or the like. The processing procedure of the authentication method deciding unit 113 is generally realized by software, and the software for this is recorded in a recording medium such as a ROM. Note that the processing procedure also may be realized by hardware (dedicated circuitry).

The region information storage section 1131 can have stored therein one or more pieces of region information that indicates a region. The region information includes, for example, upper left position information (latitude 1, longitude 1) and lower right position information (latitude 2, longitude 2) that specify a rectangular region. Also, the region information may be the name of a local government. Also, the region information storage section 1131 may have stored therein two or more pieces of region authentication information, each region authentication information associating the region information with the authentication method identification information. The authentication method identification information identifies the authentication method. Also, the region information storage section 1131 may have stored therein two or more pieces of the region authentication information, each region authentication information associating the region information, the time information, and the authentication method identification information with each other. The time information is information relating to time, and may be information indicating a time, information indicating a time period, a day of the week, and the like. Here, "associating the region information with the authentication method identification information" means that from one of the region information and the authentication method identification information, the other information can be acquired. Therefore, association information may include information that includes a set of the region information and the authentication method identification information, or may be information linking the region information to the authentication method identification information. In the latter case, the association information may be, for example, information that associates the region information with a pointer or an address that indicates the position where the authentication method identification information is stored. In the present embodiment, the former case will be described. Also, the region information is not required to be directly associated with the authentication method identification information. For example, the region information may be associated with third information, and the authentication method identification information may be associated with that third information. The region information storage section 1131 is preferably a non-volatile recording medium, but it can be realized also by a volatile recording medium. There is no restriction to the process by which region information and the like are stored in the region information storage section 1131. For example, the region information and the like may be stored in the region information storage section 1131 via a recording medium, or the region information and the like sent via a communication line or the like may be stored in the region information storage section 1131. Alternatively, the region information and the like input via an input device may be stored in the region information storage section 1131.

The determination section 1132 determines whether the position that is indicated by the position information acquired by the position information acquiring unit 112 is included in any of one or more regions indicated by one or more pieces of region information stored in the region information storage section 1131. Also, the determination section 1132 may decide the region where the position indicated by the position information acquired by the position information acquiring unit 112 is included by using the one or more pieces of region information stored in the region information storage section 1131. Also, the determination section 1132 determines whether the position information acquired by the position information acquiring unit 112 and the current time match the region information and the time information stored in the region information storage section 1131. The determination section 1132 can be generally realized by an MPU, memory or the like. The processing procedure of the determination section 1132 is generally realized by software, and the software for this is recorded in a recording medium such as a ROM. Note that the processing procedure also may be realized by hardware (dedicated circuitry).

If the determination section 1132 has determined that the position indicated by the position information is included in any of one or more regions, the authentication method deciding section 1133 selects one of two or more authentication methods. Also, if the determination section 1132 has determined that the position information acquired by the position information acquiring unit 112 and the current time match the region information and the time information stored in the region information storage section 1131, the authentication method deciding section 1133 selects one of two or more authentication methods. For example, in the case where the two or more authentication methods include a first authentication method and a second authentication method whose security level is higher than that of the first authentication method, and the determination section 1132 has determined that the position indicated by the position information is included in any of the one or more regions, the authentication method deciding section 1133 selects the first authentication method among the two or more authentication methods. Also, for example, in the case where the two or more authentication methods include a first authentication method and a second authentication method whose security level is higher than that of the first authentication method, and the determination section 1132 has determined that the position indicated by the position information is not included in the one or more regions, the authentication method deciding section 1133 selects the second authentication method among the two or more authentication methods. Note that "the security level of the second authentication method is higher than that of the first authentication method" means that, for example, the number of data pieces or the number of types of data that is input by the user is larger in the second authentication method than in the first authentication method. With respect to the types of data, the ID and the password are different types of data. Also, "the security level of the second authentication method is higher than that of the first authentication method" means that, for example, the number of terminals used is larger in the second authentication method than in the first authentication method. Also, "the security level of the second authentication method is higher than that of the first authentication method" means that, for example, the security level of the terminal used is higher than in the first authentication method. The security level of mobile phones is higher than the security level of so-called PCs, since the users of the mobile phones are identified through operation.

It is preferable that the authentication method deciding section 1133 acquires, from the region information storage section 1131, the authentication method identification information that is associated with the region information corresponding to the region for which the determination section 1132 has performed determination.

The authentication method deciding section 1133 can be generally realized by an MPU, memory or the like. The processing procedure of the authentication method deciding section 1133 is generally realized by software, and the software for this is recorded in a recording medium such as a ROM. Note that the processing procedure also may be realized by hardware (dedicated circuitry).

The authentication screen output unit 114 outputs a screen corresponding to the one authentication method decided by the authentication method deciding unit 113. For example, the authentication screen output unit 114 configures a screen by using information of a screen corresponding to the one authentication method decided by the authentication method deciding unit 113 out of information of screens stored therein, and outputs the screen. The authentication screen output unit 114 may access the server 13 by using information that identifies the one authentication method decided by the authentication method deciding unit 113, receive information of the screen corresponding to the one authentication method from the server 13, configure a screen using the information of the screen, and output the screen. It is sufficient that the authentication screen output unit 114 outputs a screen corresponding to the one authentication method decided by the authentication method deciding unit 113 as a result, and there is no restriction to the location of base information for the screen or the output algorithm used for the screen. Note that the "screen" here refers to a screen for receiving an input of information for performing authentication. Also, although it is preferable that different screens are provided corresponding to the authentication methods, one screen may be used for the authentication methods. In the case where one screen is used, it is preferable that information to be input (field to be used) differs according to the authentication method, for example. Also the same screen may be used for different authentication methods. In this case, it is preferable that the algorithm used for authentication differs according to the authentication method.

The authentication screen output unit 114 may or may not include an output device such as a display or a speaker. The authentication screen output unit 114 can be realized by a driver software of an output device, or a driver software of an output device and an output device, etc.

The authentication information sending unit 115 sends the authentication information accepted by the accepting unit 111 to the server 13. The authentication information sending unit 115 is generally realized by a wireless or wired communication means, but may also be realized by a broadcasting means.

The authentication result accepting unit 116 accepts an authentication result, which is a result of the authentication processing performed by using the authentication information. The authentication result accepting unit 116 generally receives the authentication result from the server 13. However, in the case where the terminal apparatus 11 performs authentication processing, the authentication result accepting unit 116 acquires a result of authentication performed by an authentication processing section (not shown). Here, the authentication result is information indicating success of authentication (e.g., "1") or information indicating failure of authentication (e.g., "0"), and the like. The authentication result accepting unit 116 is realized by, for example, a wireless or wired communication means, but may also be realized by a broadcasting means.

The authentication result output unit 117 outputs the authentication result accepted by the authentication result accepting unit 116. Here, "output" represents a concept that includes output to a display, projection by a projector, printing with a printer, output of a sound, sending to an outside device, accumulation in a recording medium, and delivery of processing results to other processing apparatuses or programs. The authentication result output unit 117 may or may not include an output device such as a display or a speaker. The authentication result output unit 117 can be realized by a driver software of an output device, or a driver software of an output device and an output device, etc.

The processing unit 118 performs predetermined processing only in the case where the authentication result is success of authentication. The predetermined processing is, for example, processing in which the processing unit 118 sends a command accepted by the accepting unit 111 (e.g., a command to access a database on the server 13) to the server 13, receives data from the server 13, and outputs the data. Note that the predetermined processing may be any processing. In addition, the processing unit 118 may perform different processing according to the authentication result. The processing unit 118 can be generally realized by an MPU, memory or the like. The processing procedure of the processing unit 118 is generally realized by software, and the software for this is recorded in a recording medium such as a ROM. Note that the processing procedure also may be realized by hardware (dedicated circuitry).

The second accepting unit 121 accepts an input from the user of the second terminal 12. For example, the second accepting unit 121 accepts an ID from the user of the second terminal 12. In this case, any input means such as a keyboard, a mouse, a numerical keypad, and a menu screen may be used. The second accepting unit 121 can be realized by a device driver of the input means such as a keyboard, menu screen control software, or the like.

The second sending and receiving unit 122 sends information (input) accepted by the second accepting unit 121 to the server 13. Also, the second sending and receiving unit 122 receives information from the server 13. The second sending unit 122 is generally realized by a wireless or wired communication means, but may also be realized by a broadcasting means.

The second output unit 123 outputs information received from the server 13. The second output unit 123 may or may not include an output device such as a display or a speaker. The second output unit 123 can be realized by a driver software of an output device, or a driver software of an output device and an output device, etc.

Various types of data can be stored in the data storage unit 131. Here, "various types of data" refers to, for example, medical record information of each user of the terminal apparatus 11. The medical record information includes, for example, name, age, sex, medical history, diseases under treatment, current medications, disease information of family members, and the like. The data storage unit 131 is preferably a non-volatile recording medium, but it can be realized also by a volatile recording medium.

The authentication information receiving unit 132 receives authentication information from the terminal apparatus 11, or from the terminal apparatus 11 and the second terminal 12. The authentication information receiving unit 132 is generally realized by a wireless or wired communication means, but may be realized by a means for receiving broadcasting.

The authentication unit 133 performs authentication processing using the authentication information received by the authentication information receiving unit 132, and acquires an authentication result. Note that there are cases where authentication processing is performed by using two or more pieces of authentication information. The authentication unit 133 includes two or more authentication sections. Here, description will be given assuming that the authentication unit 133 mainly includes the first authentication section 1331, the second authentication section 1332 and the third authentication section 1333. In addition, the two or more authentication sections use mutually different authentication methods. The authentication unit 133 can be generally realized by an MPU, memory or the like. The processing procedure of the authentication unit 133 is generally realized by software, and the software for this is recorded in a recording medium such as a ROM. Note that the processing procedure also may be realized by hardware (dedicated circuitry).

The first authentication section 1331 performs authentication by using, for example, authentication information made up of the ID and the password of the terminal apparatus 11. That is, the first authentication section 1331 has stored therein one or more sets of an ID and a password, and searches for the set that matches the ID and the password included in the authentication information received by the authentication information receiving unit 132. The first authentication section 1331 determines the authentication result to be success of authentication if the matching set is found, and determines the authentication result to be failure of authentication if the matching set is not found, so as to acquire information corresponding to the authentication result (for example, "1" is acquired in the case of success of authentication, and "0" is acquired in the case of failure of authentication). Note that the sets of the ID and the password may be held by the data storage unit 131, for example.

The second authentication section 1332 performs authentication processing by using, for example, authentication information made up of the ID and the password of the terminal apparatus 11, and second authentication information sent to the second terminal 12 (temporary authentication information). That is, for example, the second authentication section 1332 has stored therein one or more sets of an ID and a password, and searches for the set that matches the ID and the password included in the authentication information received by the authentication information receiving unit 132, and sends the second authentication information to the second terminal 12 if the matching set is found. Then, if the second authentication information has been sent from the terminal apparatus 11, the second authentication section 1332 determines that the authentication result is success of authentication. In contrast, if there is no set that matches the authentication information, or the second authentication information sent from the terminal apparatus 11 does not match the second authentication information that the second authentication section 1332 has sent to the second terminal 12, the second authentication section 1332 determines the authentication result to be failure of authentication.

The third authentication section 1333 performs authentication processing by using, for example, authentication information made up of two IDs and two passwords of the terminal apparatus 11, and the second authentication information (temporary authentication information) sent to the second terminal 12. Note that for example, the third authentication section 1333 performs the first authentication processing by using first ID and password, and then performs the second authentication processing by using the second ID and password, and the second authentication information.

The first authentication section 1331, the second authentication section 1332, and the third authentication section 1333 can be generally realized by an MPU, memory or the like. The processing procedure of first authentication section 1331 and the like is generally realized by software, and the software for this is recorded in a recording medium such as a ROM. Note that the processing procedure also may be realized by hardware (dedicated circuitry).

The authentication result sending unit 134 sends the authentication result acquired by the authentication unit 133 (final authentication result) to the terminal apparatus 11. The authentication result sending unit 134 is generally realized by a wireless or wired communication means, but may also be realized by a broadcasting means.

The data sending and receiving unit 135 receives a command from the terminal apparatus 11, and sends data corresponding to the command to the terminal apparatus 11. Note that the data sent here is data stored in the data storage unit 131. The data sending and receiving unit 135 is generally realized by a wireless or wired communication means, but may be realized by a means for receiving broadcasting.

Next, an operation performed by the information processing system 1 will be described. First, an operation performed by the terminal apparatus 11 will be described with reference to FIG. 3.

(Step S301) The accepting unit 111 determines whether an input of a command to execute processing that requires authentication processing has been accepted. The procedure proceeds to step S302 if an input of the command has been accepted, and if not, the procedure returns to step S301.

(Step S302) The position information acquiring unit 112 acquires position information that indicates the current position of the terminal apparatus 11. Also, a time acquiring unit (not shown) acquires the current time. Note that it is not essential to acquire the current time.

(Step S303) The authentication method deciding unit 113 selects one of two or more authentication methods according to the position information (or the position information and the current time) acquired in step S302. An example of the algorithm used for deciding the authentication method is as described below. The determination section 1132 searches the region information storage section 1131 by using the position information (or the position information and the current time) acquired in step S302. Then, the authentication method deciding section 1133 acquires, from the region information storage section 1131, authentication method identification information that corresponds to the region information (or, the region information and the time information) matching the position information (or, the position information and the current time) acquired in step S302.

(Step S304) The authentication screen output unit 114 determines whether the authentication method decided in step S303 is a first authentication method. If it is the first authentication method, the procedure proceeds to step S305, and if not, the procedure proceeds to step S306.

(Step S305) The authentication screen output unit 114 outputs a screen (authentication screen) for performing authentication corresponding to the first authentication method. For example, the authentication screen output unit 114 reads screen definition information (e.g., HTML data) corresponding to the first authentication method, interprets the screen definition information, and outputs the authentication screen. Note that in this case, the authentication screen output unit 114 holds the screen definition information in association with information that identifies the authentication method. A program (this program may be a function, method or the like) for outputting a screen corresponding to the first authentication method may be called. Then, the procedure proceeds to step S309.

(Step S306) The authentication screen output unit 114 determines whether the authentication method decided in step S303 is a second authentication method. If it is the second authentication method, the procedure proceeds to step S307, and if not, the procedure proceeds to step S308.

(Step S307) The authentication screen output unit 114 outputs a screen (authentication screen) for performing authentication corresponding to the second authentication method. Then, the procedure proceeds to step S309.

(Step S308) The authentication screen output unit 114 outputs a screen (authentication screen) for performing authentication corresponding to a third authentication method. Then, the procedure proceeds to step S309.

(Step S309) The accepting unit 111 determines whether authentication information has been accepted from the user. If authentication information has been accepted, the procedure proceeds to step S310, and if not, the procedure returns to step S309.

(Step S310) The authentication information sending unit 115 sends the authentication information accepted in step S309 to the server 13.

(Step S311) The authentication result accepting unit 116 determines whether the authentication result, which is a result of authentication processing performed by using authentication information, has been received from the server 13. If the authentication result has been received, the procedure proceeds to step S312, and if not, the procedure returns to step S311.

(Step S312) The authentication result output unit 117 outputs the authentication result accepted by the authentication result accepting unit 116. The authentication result output here is the final authentication result. Note that it is not essential to output the authentication result.

(Step S313) The processing unit 118 determines whether the authentication result is success of authentication. If the authentication result is success of authentication, the procedure proceeds to step S314, and if the authentication result is failure of authentication, the procedure returns to step S301.

(Step S314) The processing unit 118 performs predetermined processing corresponding to the input from the user. Then, the procedure returns to step S301.

Note that there is no restriction to details of the processing performed in step S314 of the flowchart in FIG. 3.

Note that in the flowchart shown in FIG. 3, the processing ends due to powering off or interruption for aborting the processing.

Next, an operation performed by the second terminal 12 will be described. The second accepting unit 121 of the second terminal 12 accepts an input from the user of the second terminal 12. Then, the second sending and receiving unit 122 sends information (input) accepted by the second accepting unit 121 to the server 13. Information may be received from the server 13. Then, the second output unit 123 outputs information received by the second sending and receiving unit 122. Note that the information output here is, for example, information necessary for authentication.

Next, an operation of the server 13 will be described with reference to the flowchart shown in FIG. 4.

(Step S401) The authentication information receiving unit 132 determines whether authentication information has been received from the terminal apparatus 11, or the terminal apparatus 11 and the second terminal 12. Note that the authentication information includes, for example, authentication method identification information that identifies the authentication method.

(Step S402) The authentication unit 133 performs authentication processing corresponding to the authentication method identification information included in the authentication information received by the authentication information receiving unit 132, and acquires an authentication result. An example of the details of the authentication processing is as described above.

(Step S403) The authentication result sending unit 134 sends the authentication result acquired in step S402 to the terminal apparatus 11. Then, the procedure returns to step S401.

(Step S404) The data sending and receiving unit 135 determines whether a command (command instructing the sending of data) has been received from the terminal apparatus 11. If the command has been received, the procedure proceeds to step S405, and if not, the procedure returns to step S401.

(Step S405) The data sending and receiving unit 135 acquires data stored in the data storage unit 131 according to the command received in step S404.

(Step S406) The data sending and receiving unit 135 sends the data received in step S405 to the terminal apparatus 11.

Note that although data search processing and sending processing are performed after authentication in the flowchart shown in FIG. 4, there is no restriction to the details of the processing.

Note that in the flowchart shown in FIG. 4, the processing ends due to powering off or interruption for aborting the processing.

Hereinafter, a specific operation of the information processing system 1 of the present embodiment will be described. The conceptual diagram of the information processing system 1 is shown in FIG. 1.

The region information storage section 1131 holds a region authentication information management table shown in FIG. 5. The region authentication information management table holds one or more records, each record including attribute values of "ID", "Region information", "Time information", and "Authentication method identification information". "ID" is information that identifies the record. The information $(x_1, y_1) (x_2, y_2)$ corresponding to the attribute "Region information" in the records of "ID=1 and 2" each means (latitude, longitude), and the information $(x_1, y_1) (x_2, y_2)$ indicates a rectangular region. Note that the rectangular region indicated by the region information $(x_1, y_1) (x_2, y_2)$ indicates the region of the premise of a hospital (hospital A) that users (user 1 to user 3) of the terminal apparatus 11 usually visit. "Others" in the record of "ID=3" indicates that this record is applied when the region information is not $(x_1, y_1) (x_2, y_2)$. That is, the record of "ID=1" in the region authentication information management table indicates that the authentication method employed during a time period "9:00 to 18:00" (e.g., regular consultation hours) of the hospital A is the "method 1". Also, the record of "ID=2" in the region authentication information management table indicates that the authentication method employed during a time period "18:01 to 8:59" (e.g., out of consultation hours) of the hospital A is the "method 2". Furthermore, the record of "ID=3" in the region authentication information management table indicates that the authentication method employed in regions other than the hospital A is the "method 3". Note that the security levels of the authentication methods have the following relationship: method 1<method 2<method 3. The method 1 is realized by the first authentication section 1331. The method 2 is realized by the second authentication section 1332. The method 3 is realized by the third authentication section 1333.

In addition, the data storage unit 131 holds a medical record information management table shown in FIG. 6. The medical record information management table manages information such as medical history of patients (medical record information), information necessary for authentication, and the like. The medical record information management table holds one or more records, each record including "No.", "First authentication information", "Second authentication information", "Terminal identification information" and "Output information". "No." is information that identifies the record. "First authentication information" includes "ID1" and "PW1" used by the first authentication section 1331, the second authentication section 1332 and the third authentication section 1333. "Second authentication information" includes "ID2" and "PW2" used only by the third authentication section 1333. "ID1" and "ID2" are IDs necessary for logging into or accessing the server 13. "PW1" and "PW2" are passwords necessary for logging into or accessing the server 13. "Terminal identification information" is information that identifies the second terminal 12, and here it is the telephone number of the second terminal 12. Note that here, the second terminal 12 is a so-called mobile phone, for example. "Output information" includes attributes of the user (patient) of the second terminal 12, medical record information (medical information), which is information related to diseases, of the user (patient), and the like.

Now, three specific examples will be described.

Example 1

It is assumed that a user 1 visited the hospital A that he or she usually visits to see his or her doctor, namely, doctor X, for examination. It is assumed that doctor X attempts to acquire medical record information of the user 1 from the server 13 by using the terminal apparatus 11 installed in the hospital A.

Then, the doctor X has input a command to access the server 13 to the terminal apparatus 11.

The terminal apparatus 11 accepts the input of the command to access the server 13. The GPS receiver serving as the position information acquiring unit 112 acquires position information $(x_3, y_3)$ indicating the current position of the terminal apparatus 11. It is assumed that the time acquiring unit (not shown) acquires the current time "9:45".

Next, the authentication method deciding unit 113 searches the region authentication information management table shown in FIG. 5 using the position information $(x_3, y_3)$ and the current time "9:45" that have been acquired. Then, the authentication method deciding unit 113 detects that the position indicated by the position information $(x_3, y_3)$ is within the rectangular region indicated by the region information $(x_1, y_1) (x_2, y_2)$. The authentication method deciding unit 113 determines that the current time "9:45" corresponds to the time period "9:00 to 18:00" and acquires authentication method identification information "method 1".

Next, the authentication screen output unit 114 displays an authentication screen in which the decided authentication method corresponds to the authentication method identification information "method 1", as shown in FIG. 7.

Then, it is assumed that the doctor X has input the ID "5631" and the PW "abc" and has pressed the "Login" button in order to access the medical record information of the user 1. Note that for example, it is also possible that the doctor X acquires the ID "5631" and the PW "abc" from the user 1 and inputs them.

Then, the authentication information sending unit 115 configures authentication information "method 1, ID: 5631, PW: abc" and sends that authentication information to the server 13.

The authentication information receiving unit 132 of the server 13 receives the authentication information "method 1, ID: 5631, PW: abc".

Then, the authentication unit 133 calls the first authentication section 1331 based on "method 1" included in the authentication information received by the authentication information receiving unit 132, and forwards "ID: 5631, PW: abc" to the first authentication section 1331.

Next, the first authentication section 1331 determines whether there is first authentication information that matches "ID: 5631, PW: abc" in the medical record information management table shown in FIG. 6. The first authentication section 1331 determines that the record of "ID=1" in the medical record information management table in FIG. 6 matches "ID: 5631, PW: abc".

Then, the authentication unit 133 acquires an authentication result "success of authentication".

Next, the authentication result sending unit 134 sends the acquired authentication result "success of authentication" to the terminal apparatus 11.

The authentication result accepting unit 116 receives the authentication result "success of authentication" from the server 13. Then, the authentication result output unit 117 outputs the authentication result "success of authentication" accepted by the authentication result accepting unit 116.

Thereafter, medical record information (information in the record of "ID=1" in FIG. 6) of the user 1 is downloaded and output by the terminal apparatus 11 according to the operation performed by the doctor X on the terminal apparatus 11.

Then, the doctor X of the user 1 can readily perform medical practice while referencing the medical record information of the user 1.

Example 2

Next, it is assumed that a user 2 suddenly has become ill in the night and has visited the hospital A that he or she usually visits, and that doctor Y of the hospital A (who is not the doctor of the user 2) sees the user 2.

The doctor Y has input the command to access the server 13 to the terminal apparatus 11.

The terminal apparatus 11 accepts the input of the command to access the server 13. The GPS receiver serving as the position information acquiring unit 112 acquires the position information $(x_3, y_3)$ indicating the current position of the terminal apparatus 11. It is assumed that the time acquiring unit (not shown) acquires the current time "22:18".

Next, the authentication method deciding unit 113 searches the region authentication information management table shown in FIG. 5 using the position information $(x_3, y_3)$ and the current time "22:18" that have been acquired. Then, the authentication method deciding unit 113 detects that the position indicated by the position information $(x_3, y_3)$ is within the rectangular region indicated by the region information $(x_1, y_1) (x_2, y_2)$. The authentication method deciding unit 113 determines that the current time "22:18" corresponds to the time period "18:01 to 8:59" and acquires authentication method identification information "method 2".

Next, the authentication screen output unit 114 displays an authentication screen in which the decided authentication method corresponds to the authentication method identification information "method 2", as shown in FIG. 7.

Then, it is assumed that the doctor Y has input the ID "1221" and the PW "xy3" and has pressed the "Login" button in order to access the medical record information of the user 2. Note that the doctor Y acquires the ID "1221" and the PW "xy3" from the user 2, and inputs them.

Then, the authentication information sending unit 115 configures authentication information "method 2, ID: 1221, PW: xy3" and sends that authentication information to the server 13.

The authentication information receiving unit 132 of the server 13 receives the authentication information "method 2, ID: 1221, PW: xy3".

Then, the authentication unit 133 calls the second authentication section 1332 based on "method 2" included in the authentication information received by the authentication information receiving unit 132, and forwards "ID: 1221, PW: xy3" to the second authentication section 1332.

Next, the second authentication section 1332 determines whether there is the first authentication information that matches "ID: 1221, PW: xy3" in the medical record information management table shown in FIG. 6. The second authentication section 1332 determines that the record of "ID=2" in the medical record information management table in FIG. 6 matches "ID: 1221, PW: xy3".

Then, the second authentication section 1332 automatically configures second authentication information (temporary authentication information).

Note that it is assumed that the second authentication section 1332 has executed f(1221, xy3) by using "ID: 1221, PW: xy3", and has configured second authentication information (a85bq9), for example. Then, the second authentication section 1332 temporarily stores the second authentication information (a85bq9) in a storage section (not shown).

Next, the second authentication section 1332 reads out terminal identification information "080-7788-1234" in the record of "ID=2" from the table shown in FIG. 6.

Then, the authentication result sending unit 134 sends the second authentication information (a85bq9) to the second terminal 12 identified by the terminal identification information "080-7788-1234".

Also, the authentication result sending unit 134 sends a processing result of the first authentication processing "success of authentication" to the terminal apparatus 11.

The second sending and receiving unit 122 of the second terminal 12 receives the second authentication information (a85bq9) from the server 13. Then, the second output unit 123 outputs the second authentication information (a85bq9) received from the server 13. FIG. 8 is an example of the second authentication information output by the second terminal 12.

Next, the authentication result accepting unit 116 of the terminal apparatus 11 receives the processing result of the first authentication processing "success of authentication".

Then, the authentication screen output unit 114 outputs a second authentication screen for performing second authentication. An example of the second authentication screen is shown in FIG. 9.

Then, the doctor Y inputs the second authentication information (a85bq9) in the input field of the second authentication screen shown in FIG. 9, and presses the "Send" button.

The accepting unit 111 accepts the second authentication information (a85bq9), and the authentication information sending unit 115 sends the second authentication information (a85bq9) accepted by the accepting unit 111 to the server 13.

Next, the authentication information receiving unit 132 of the server 13 receives the second authentication information (a85bq9) from the terminal apparatus 11.

Next, the second authentication section 1332 determines whether the second authentication information (a85bq9) matches the temporarily stored second authentication information. Here, since both information pieces match, the second authentication section 1332 determines the final authentication result to be "success of authentication".

Next, the authentication result sending unit 134 sends the final authentication result "success of authentication" to the terminal apparatus 11.

Next, the authentication result accepting unit 116 receives the final authentication result "success of authentication" from the server 13. Then, the authentication result output unit 117 outputs the authentication result "success of authentication" accepted by the authentication result accepting unit 116.

Thereafter, the medical record information (information in the record of "ID=2" in FIG. 6) of the user 2 is downloaded and output by the terminal apparatus 11 according to the operation performed by the doctor Y on the terminal apparatus 11.

Then, the doctor Y can readily perform medical practice while referencing the medical record information of the user 2.

Example 3

Next, it is assumed that the user 3 has become ill when he or she is walking on the street, and has been put in an ambulance. It is also assumed that the user 3 told the ID and the password upon request from an ambulance crew member Z, and that the ambulance crew member Z attempts to conduct emergency treatment while referencing the medical record information of the user 3.

First, the ambulance crew member Z has input the command to access the server 13 to the terminal apparatus 11 installed in the ambulance car.

The terminal apparatus 11 accepts the input of the command to access the server 13. The GPS receiver serving as the position information acquiring unit 112 acquires position information ($x_4$, $y_4$) indicating the current position of the terminal apparatus 11. It is assumed that the time acquiring unit (not shown) acquires the current time "14:33".

Next, the authentication method deciding unit 113 searches the region authentication information management table shown in FIG. 5 using the position information ($x_4$, $y_4$) and the current time "14:33" that have been acquired. Then, the authentication method deciding unit 113 detects that the position indicated by the position information ($x_4$, $y_4$) is outside the rectangular region indicated by the region information ($x_1$, $y_1$) ($x_2$, $y_2$). The authentication method deciding unit 113 acquires authentication method identification information "method 3".

Next, the authentication screen output unit 114 displays an authentication screen in which the decided authentication method corresponds to the authentication method identification information "method 3", as shown in FIG. 10.

Then, it is assumed that the ambulance crew member Z has input an ID "7215" and a PW "a35" and has pressed the "Login" button in order to access the medical record information of the user 3. Note that it is assumed that the ambulance crew member Z has acquired the ID "7215" and the PW "a35" from the user 3 and has input them.

Then, the authentication information sending unit 115 configures authentication information "method 3, ID: 7215, PW: a35" and sends that authentication information to the server 13

The authentication information receiving unit 132 of the server 13 receives the authentication information "method 3, ID: 7215, PW: a35".

Then, the authentication unit 133 calls the third authentication section 1333 based on "method 3" included in the authentication information received by the authentication information receiving unit 132, and forwards "ID: 7215, PW: a35" to the third authentication section 1333.

Next, the third authentication section 1333 determines whether there is the first authentication information that matches "ID: 7215, PW: a35" in the medical record information management table shown in FIG. 6. The third authentication section 1333 determines that the record of "ID=3" in the medical record information management table in FIG. 6 matches "ID: 7215, PW: a35".

Then, the third authentication section 1333 automatically configures second authentication information (e.g., "78zqy5"). Then, the second authentication section 1332 temporarily stores the second authentication information (78zqy5) in a storage section (not shown).

Next, the third authentication section 1333 reads out terminal identification information "090-1222-7753" in the record of "ID=3" from the table shown in FIG. 6.

Then, the authentication result sending unit 134 sends the second authentication information (78zqy5) to the second terminal 12 identified by the terminal identification information "090-1222-7753".

Also, the authentication result sending unit 134 sends a processing result of the first authentication processing "success of authentication" to the terminal apparatus 11.

The second sending and receiving unit 122 of the second terminal 12 receives the second authentication information (78zqy5) from the server 13. Then, the second output unit 123 outputs the second authentication information (78zqy5) received from the server 13.

Next, the authentication result accepting unit 116 of the terminal apparatus 11 receives the processing result of the first authentication processing "success of authentication".

Then, the authentication screen output unit 114 outputs a second authentication screen for performing second authentication. An example of the second authentication screen is shown in FIG. 11. In FIG. 11, it is required to input the second ID, the second password and the second authentication information.

Next, the ambulance crew member Z acquires the second ID and the second password from the user 3 and also acquires the second authentication information "78zqy5" output in the display of the second terminal 12 of the user 3.

Then, the ambulance crew member Z inputs the second ID "ppxx", the second password "555", and the second authentication information "78zqy5" in the screen of FIG. 11, and presses the "Send" button.

The accepting unit 111 accepts the second ID "ppxx", the second password "555", and the second authentication information "78zqy5", and the authentication information sending unit 115 sends the authentication information accepted by the accepting unit 111 (second ID: ppxx, second password: 555, second authentication information: 78zqy5) to the server 13.

Next, the authentication information receiving unit 132 of the server 13 receives the authentication information (second ID: ppxx, second password: 555, second authentication information: 78zqy5) from the terminal apparatus 11.

Next, the third authentication section 1333 determines whether the second authentication information (78zqy5) matches the temporarily stored second authentication information. Here, the third authentication section 1333 determines that both information pieces match.

Also, the third authentication section 1333 determines whether the second ID "ppxx" and the second password "555" match the ID2 and PW2 of the user 3. Since they match each other, the third authentication section 1333 decides the final authentication result to be "success of authentication".

Next, the authentication result sending unit 134 sends the final authentication result "success of authentication" to the terminal apparatus 11.

The authentication result accepting unit 116 receives the final authentication result "success of authentication" from the server 13. Then, the authentication result output unit 117 outputs the authentication result "success of authentication" accepted by the authentication result accepting unit 116.

Thereafter, the medical record information (information in the record of "ID=3" in FIG. 6) of the user 3 is downloaded and output by the terminal apparatus 11 according to the operation performed by the ambulance crew member Z on the terminal apparatus 11.

Then, the ambulance crew member Z can readily conduct emergency treatment while referencing the medical record information of the user 2.

As described above, with the present embodiment, it is possible to change the authentication method according to the position. For example, it is possible to access the server 13 with a simple authentication method in a place where the user is usually present. When the user has moved to a place where the user is not usually present, access to the server 13 is made while ensuring a high security level.

Also, with the present embodiment, it is possible to change the authentication method according to the position, the time period, and the like.

Note that in the present embodiment, three or more authentication methods are used according to the position or the like. However, it is sufficient that two authentication methods are switched according to the position. In this case, for example, the region information storage section 1131 holds a region authentication information management table shown in FIG. 12. The region authentication information management table shown in FIG. 12 manages only the position information to which a simple authentication method, namely, the authentication method 1, is applied. In the region authentication information management table in FIG. 12, one or more records, each record including "ID", "Region name", and "Region information", are stored. "Region information" indicates (latitude, longitude) corresponding to the boundary of the local government indicated by "Region name". In FIG. 12, in the case where the server 13 is accessed in a city such as Asahikawa, Sapporo, or the like, it is possible to access the server 13 with a simple authentication method (for example, with the above-described authentication method 1). In regions that are not managed in the region authentication information management table of FIG. 12, it is possible to access the server 13 with a strict authentication method (for example, with the above-described authentication method 2). Note that it is preferable that the records in the region authentication information management table are set for each user.

Although the terminal apparatus 11 decides the authentication method in the present embodiment, the server may decide the authentication method. In addition, although the terminal apparatus 11 outputs the authentication screen corresponding to the authentication method in the present embodiment, the server may output the authentication screen. FIG. 13 shows a block diagram of an information processing system 2 used in such a case. That is, a server 23 includes a position information receiving unit 231 that receives position information of a terminal apparatus 21, the authentication method deciding unit 113, an authentication screen sending unit 232, the authentication information receiving unit 132, the authentication unit 133, the authentication result sending unit 134, and the like. Also, the terminal apparatus 21 includes the accepting unit 111, the position information acquiring unit 112, a position information sending unit 211 that sends the position information to the server 23, an authentication screen receiving unit 212 that receives the authentication screen from the server 23, an authentication screen output unit 213 that outputs the authentication screen, the authentication information sending unit 115, the authentication result accepting unit 116, the authentication result output unit 117 and the processing unit 118.

Furthermore, the processing in the present embodiment may be realized by software. Such software may be distributed by downloading of software product or the like. In addition, such software may be recorded on a recording medium such as a CD-ROM and distributed. Also, needless to say, such software or the recording medium in which the software is recorded may be distributed as a computer program product. Note that this applies to other embodiments of the invention as well. Software that realizes a terminal apparatus of the present embodiment may be a program as described below. That is, this program is a program for causing a computer to function as a position information acquiring unit that acquires position information that indicates a current position of the terminal apparatus, an authentication method deciding unit that selects one of two or more authentication methods according to the position information acquired by the position information acquiring unit, an authentication screen output unit that outputs a screen that corresponds to the one authentication method selected by the authentication method deciding unit, an accepting unit that accepts authentication information that is input by a user on the screen output by the authentication screen output unit, an authentication result accepting unit that accepts an authentication result, which is a result of authentication processing performed by using the authentication information, and an authentication result output unit that outputs the authentication result.

With the program, it is preferable that the computer is caused to function such that the authentication method deciding unit has stored in a storage medium one or more pieces of region information each of which indicates a region, and includes a determination section that determines whether the position that is indicated by the position information acquired by the position information acquiring unit is included in any of one or more regions that are indicated by the one or more pieces of region information stored in the storage medium, and an authentication method deciding section that selects one of the two or more authentication methods in a case where the determination section has determined that the position indicated by the position information is included in any of the one or more regions.

Also, with the program, it is preferable that the two or more authentication methods include a first authentication method and a second authentication method having a security level that is higher than that of the first authentication method, and in a case where the determination section has determined that the position indicated by the position information is included in any of the one or more regions, the authentication method deciding section selects the first authentication method from among the two or more authentication methods, and in a case where the determination section has determined that the position indicated by the position information is included in none of the one or more regions, the authentication method deciding section selects the second authentication method from among the two or more authentication methods.

Also, with the program, it is preferable that the storage medium has stored therein two or more pieces of region authentication information, each piece associating region information with authentication method identification information that identifies the authentication method corresponding to that region information, the determination section determines a region where the position that is indicated by the position information acquired by the position information acquiring unit is included by using the one or more pieces of region information stored in the storage medium, and the authentication method deciding section acquires, from the storage medium, the authentication method identification information that is associated with the region information corresponding to the region determined by the determination section.

Embodiment 2

In the present embodiment, an information processing system 3 will be described in which the authentication result is obtained as success of authentication only when the positions of two terminal apparatuses satisfy a specific condition. The specific condition is, for example, that the distance between the positions of two terminal apparatuses is within a fixed distance, or that the two terminal apparatuses are present in the same region.

The conceptual diagram of the information processing system 3 of the present embodiment is similar to that shown in FIG. 1. Also, FIG. 14 is a block diagram of the information processing system 3 of the present embodiment.

The information processing system 3 includes a terminal apparatus 31, a second terminal 32, and a server 33. Note that in the present invention, the terminal apparatus may be referred to as a first terminal apparatus. Also, the second terminal may be referred to a second terminal apparatus, when appropriate.

The terminal apparatus 31 includes the accepting unit 111, a first position information storage unit 311, a first sending unit 312, a first receiving unit 313, a first output unit 314 and the processing unit 118.

The second terminal 32 includes a second terminal identifier storage unit 120, a second position information acquiring unit 321, and a second sending unit 322.

The server 33 includes a first position information receiving unit 331, a second position information receiving unit 332, an authentication unit 333, an authentication result sending unit 334, the data storage unit 131, and the data sending and receiving unit 135.

The terminal apparatus 31 is a terminal fixed in a certain place, for example. The terminal apparatus 31 is, for example, a terminal for a doctor to reference medical record information such as medical history of patients in a hospital. Note that the terminal apparatus 31 may be a portable terminal.

The second terminal 32 is, for example, a portable terminal held by a patient. Note that the second terminal 32 may be provided in other forms such as a laptop computer.

In addition, the server 33 is a device for performing authentication processing. The server 33 may be a server for downloading various types of information to the terminal apparatus 31 in the case where the result of the authentication processing is success of authentication, for example. There is no restriction to the processing performed by the server 33.

In the first position information storage unit 311, first position information that indicates the position of the terminal apparatus 31 can be stored. The terminal apparatus 31 includes a section for acquiring the first position information, and the first position information acquired by that section may be stored in the first position information storage unit 311. The first position information may be any information as long as it identifies the position of the terminal apparatus 31, such as (latitude, longitude). The first position information storage unit 311 is preferably a non-volatile recording medium, but it can be realized also by a volatile recording medium. There is no restriction to the process by which the first position information is stored in the first position information storage unit 311. For example, the first position information may be stored in the first position information storage unit 311 via a recording medium, or the first position information sent via a communication line or the like may be stored in the first position information storage unit 311. Alternatively, the first position information input via an input device may be stored in the first position information storage unit 311.

The first sending unit 312 sends the first position information to the server 33. The first sending unit 312 may send the first position information in accordance with an instruction given by the user, or may send the first position information periodically. It is preferable that the first sending unit 312 sends a second terminal apparatus identifier (e.g., telephone number, IP address, and the like of the second terminal 32) that identifies the second terminal 32 and the first position information as a pair. The first sending unit 312 is generally realized by a wireless or wired communication means, but may also be realized by a broadcasting means.

The first receiving unit 313 receives the authentication result from the server 33. The authentication result is, for example, success of authentication (e.g., "1") or failure of authentication (e.g., "0"). The first receiving unit 313 is generally realized by a wireless or wired communication means, but may be realized by a means for receiving broadcasting.

The first output unit 314 outputs the authentication result. Here, "output" represents a concept that includes output to a display, projection by a projector, printing with a printer, output of a sound, sending to an outside device, accumulation in a recording medium, and delivery of processing results to other processing apparatuses or programs. The first output unit 314 may or may not include an output device such as a display or a speaker. The first output unit 314 can be realized by a driver software of an output device, or a driver software of an output device and an output device, etc.

The second position information acquiring unit 321 acquires second position information that indicates the position of the second terminal 32. The second position information is, for example, (latitude, longitude). The second position information acquiring unit 321 can be realized by, for example, a GPS receiver.

The second sending unit 322 sends the second position information to the server 33. The first sending unit 312 normally sends the second position information in accordance with an instruction given by a user. Also, it is preferable that the second sending unit 322 sends the second terminal apparatus identifier that identifies the second terminal 32 and the second position information as a pair. The second sending unit 322 is generally realized by a wireless or wired communication means, but may also be realized by a broadcasting means.

The first position information receiving unit 331 receives the first position information from the terminal apparatus 31. The first position information receiving unit 331 is generally realized by a wireless or wired communication means, but may be realized by a means for receiving broadcasting.

The second position information receiving unit 332 receives the second position information from the second terminal 32. The second position information receiving unit 332 is generally realized by a wireless or wired communication means, but may be realized by a means for receiving broadcasting.

The authentication unit 333 determines whether the first position information and the second position information have a predetermined relation. If the first position information and the second position information have the predetermined relation, the authentication result indicating success of authentication is acquired, and if not, the authentication result indicating failure of authentication is acquired. Here, the predetermined relation is, for example, that the distance between the point indicated by the first position information and the point indicated by the second position information is less than a predetermined distance, or less than or equal to the predetermined distance. The authentication unit 333 can be generally realized by an MPU, memory or the like. The processing procedure of the authentication unit 333 is generally realized by software, and the software for this is recorded in a recording medium such as a ROM. Note that the processing procedure also may be realized by hardware (dedicated circuitry).

The authentication result sending unit 334 sends the authentication result acquired by the authentication unit 333 to the terminal apparatus 31. The authentication result sending unit 334 is generally realized by a wireless or wired communication means, but may also be realized by a broadcasting means.

Next, an operation of the information processing system 3 will be described. First, an operation of the terminal apparatus 31 will be described. The accepting unit 111 of the terminal apparatus 31 accepts a second terminal identifier, and also accepts an instruction to start authentication processing. Then, the first sending unit 312 reads out first position information from the first position information storage unit 311. The first sending unit 312 sends the first position information and the accepted second terminal identifier to the server 33 as a pair. Then, in response to this sending, the first receiving unit 313 receives an authentication result (success of authentication or failure of authentication). Next, the first output unit 314 outputs the authentication result. If the authentication result is success of authentication, thereafter, the first receiving unit 313 of the terminal apparatus 31 accesses the server 33 according to instructions given by a user (e.g., doctor), and receives information (e.g., medical record information of the patient). Then, the first output unit 314 outputs the information (e.g., medical record information of the patient). Note that the processing unit 118 may perform various types of processing on the received information.

Next, an operation of the second terminal 32 will be described. As a result of an unshown section (acceptance section) of the second terminal 32 having accepted an instruction given by the user, the second position information acquiring unit 321 acquires the second position information. Then, the second sending unit 322 sends the second position information and the second terminal identifier in the second terminal identifier storage unit 120 to the server 33 as a pair.

Next, an operation of the server 33 will be described with reference to the flowchart shown in FIG. 15.

(Step S1501) The first position information receiving unit 331 determines whether the first position information has been received. If the first position information has been received, the procedure proceeds to step S1502, and if not, the procedure proceeds to step S1509. Note that here, the first position information receiving unit 331 may receive the first position information and the second terminal identifier.

(Step S1502) The authentication unit 333 stores, at least temporarily, the first position information, or the first position information and second terminal identifier that have been received in step S1501 in a recording medium (not shown).

(Step S1503) The second position information receiving unit 332 determines whether the second position information has been received. If the second position information has been received, the procedure proceeds to step S1504, and if not, the procedure returns to step S1503. Note that here, the second position information receiving unit 332 may receive the second position information and the second terminal identifier.

(Step S1504) The authentication unit 333 stores, at least temporarily, the second position information, or the second position information and second terminal identifier that have been received in step S1503 in a recording medium (not shown).

(Step S1505) The authentication unit 333 determines whether the first position information received in step S1501 and the second position information received in step S1503 satisfy a predetermined condition. Note that here, when acquiring the first position information and the second position information, the authentication unit 333 may acquire the first position information and the second position information that are each paired with the same second terminal identifier, the first position information and the second position information that are associated with each other using other information, or the first position information and the second position information that have the shortest difference in the reception time. Also, the authentication unit 333 may calculate the distance between the position indicated by the first position information and the position indicated by the second position information, and determine whether the calculated distance is less than or equal to a predetermined distance (that is stored in advance in a recording medium), or less than the predetermined distance. Also, the authentication unit 333 may determine whether the first position information and the second position information both indicate a position in a predetermined region (that is stored in advance in a recording medium). For example, consider a case in which the predetermined region is a rectangular region having its upper left position at (x1, y1) and its lower right position at (x2, y2). In this case, the authentication unit 333 determines whether the first position information (x3, y3) and the second position information (x4, y4) satisfy the following conditions, that is, $x1 \leq x3 \leq x2$, $y1 \leq y3 \leq y2$, $x1 \leq x4 \leq x2$, and $y1 \leq y4 \leq y2$ (where $x1 < x2$, and $y1 < y2$). The authentication unit 333 moves to step S1506 if the determination result is that the conditions are satisfied, and if not, it moves to step S1507.

(Step S1506) The authentication unit 333 assigns "success of authentication" to a variable "authentication result". Then, the procedure proceeds to step S1508.

(Step S1507) The authentication unit 333 assigns "failure of authentication" to the variable "authentication result".

(Step S1508) The authentication result sending unit 334 sends the authentication result to the second terminal 32, and the procedure returns to step S1501. Note that the authentication unit 333 normally stores the second terminal apparatus identifier, the first terminal identifier and the authentication result in association with each other in a storage section (not shown).

(Step S1509) The data sending and receiving unit 135 determines whether an instruction to send data has been received from the second terminal 32. If the instruction to send data has been received, the procedure proceeds to step S1510, and if not, the procedure returns to step S1501. Note that the instruction to send data normally includes the second terminal apparatus identifier for communicating with the second terminal 32.

(Step S1510) The data sending and receiving unit 135 determines whether the terminal apparatus 31 that has sent the instruction to send data, which has been received in step S1509, is the second terminal 32 for which authentication has succeeded. If the terminal apparatus is the second terminal 32 that was authenticated, the procedure proceeds to step S1511, and if not, the procedure returns to step S1501. Note that for example, the data sending and receiving unit 135 acquires the authentication result that is paired with the second terminal apparatus identifier included in the instruction to send data that has been received in step S1509 from a storage section (not shown), and determines whether the terminal apparatus is the second terminal 32 that was authenticated.

(Step S1511) The data sending and receiving unit 135 reads out data corresponding to the instruction to send data received in step S1509 from the data storage unit 131.

(Step S1512) The data sending and receiving unit 135 sends the data acquired in step S1511 to the second terminal 32. Then, the procedure returns to step S1501.

Note that in the flowchart shown in FIG. 15, the processing ends due to powering off or interruption for aborting the processing.

Also, in the flowchart shown in FIG. 15, the server 33 receives the second position information after having received the first position information. However, there is no restriction to the receiving order of the first position information and the second position information.

A specific operation of the information processing system 3 of the present embodiment will be described below. The conceptual diagram of the information processing system 3 is shown in FIG. 1.

It is assumed that the terminal apparatus 31 is a terminal that is installed in a hospital and used by doctors for referencing medical record information of patients. The second terminal 32 is a portable terminal held by a patient. Medical record information of patients is stored in the server 33, and if the authentication result is success of authentication, the medical record information of the patient who holds the second terminal 32 that was authenticated is sent to the authenticated terminal apparatus 31 according to an instruction given by the terminal apparatus 31.

First position information (Xa, Ya) that indicates the position of the hospital (or doctor's examination room in the hospital) is stored in the first position information storage unit 311 of the terminal apparatus 31.

The second terminal identifier "09012227753" of the second terminal 32 (here, telephone number of the second terminal 32) is stored in the second terminal identifier storage unit 120 of the second terminal 32. Furthermore, the medical record information management table shown in FIG. 6 is held in the data storage unit 131 of the server 33.

In this situation, it is assumed that the holder of the second terminal 32 (Hiroko Yamamoto) has visited a doctor (Y)'s examination room of the hospital for examination.

It is assumed that the doctor (Y) has acquired the mobile phone number of the patient (Hiroko Yamamoto) for authentication, has input her mobile phone number, and has pressed the "Send" button, as shown in the screen (FIG. 16) of the terminal apparatus 31.

Note that needless to say, the information that is input is not limited to the mobile phone number. The input information may be any information that identifies the patient or the second terminal 32. For example, the name and the birth date of the patient may be used as the input information.

Then, the accepting unit 111 of the terminal apparatus 31 accepts an instruction to send information for authentication.

Next, the first sending unit 312 reads out the first position information (Xa, Ya) from the first position information storage unit 311. Then, the first sending unit 312 sends the first position information (Xa, Ya) and the accepted second terminal identifier "09012227753" to the server 33 as a pair. Note that here, the terminal apparatus 31 also sends identification information (e.g., IP address) of the terminal apparatus 31 to the server 33, in order for the server 33 to return the authentication result to the terminal apparatus 31.

Next, the patient inputs, to her own second terminal 32, an instruction to send the second position information to the server 33.

Then, an unshown section (accepting section) of the second terminal 32 accepts the user's instruction (the instruction to send the second position information to the server 33). The second position information acquiring unit 321 accepts second position information (Xb, Yb). Then, the second sending unit 322 sends the second position information (Xb, Yb) and the second terminal identifier "09012227753" in the second terminal identifier storage unit 120 to the server 33 as a pair.

The first position information receiving unit 331 of the server 33 receives the first position information (Xa, Ya) and the second terminal identifier "09012227753". Then, the authentication unit 333 temporarily stores the first position information (Xa, Ya) and the second terminal identifier "09012227753" that have been received in a recording medium.

Next, the second position information receiving unit 332 receives the second position information (Xb, Yb) and the second terminal identifier "09012227753". Then, the authentication unit 333 temporarily stores the second position information (Xb, Yb) and the second terminal identifier "09012227753" that have been received in a recording medium.

Next, the authentication unit 333 reads out the first position information (Xa, Ya) and the second position information (Xb, Yb) that are each paired with the second terminal identifier "09012227753" from a recording medium.

Then, the authentication unit 333 calculates a distance (d) between the position indicated by the first position information and the position indicated by the second position information, and determines whether the distance is less than or equal to a predetermined distance (da). Assuming the condition d<da, the authentication unit 333 calculates the distance (d) between the position indicated by the first position information and the position indicated by the second position information. Then, the authentication unit 333 reads out a pre-stored distance (da), which constitutes the condition (the condition that the distance is less than or equal to the predetermined distance (da)). Then, the authentication unit 333 compares the distance (d) with the distance (da), determines that the distance between the position indicated by the first position information and the position indicated by the second position information is less than or equal to the predetermined distance based on the comparison result that d<da, and determines that the authentication result is success of authentication.

Then, the authentication unit 333 assigns "success of authentication" to the variable "authentication result". Next, the authentication result sending unit 334 sends the authentication result "success of authentication" to the second terminal 32.

Next, the first receiving unit 313 of the terminal apparatus 31 receives the authentication result "success of authentication". Next, the first output unit 314 outputs the authentication result "success of authentication".

Thereafter, the doctor (Y) can acquire the medical record information of the patient (Hiroko Yamamoto) from the server 33. Since processing for acquiring medical record information is a known technique, the description thereof is not given here.

As described above, with the present embodiment, the authentication result is obtained as success of authentication in the case where the positional relation between two terminal apparatuses satisfies a predetermined positional relation. In this manner, it is possible for the information referencing side (e.g., doctor) to reference information only if the information providing side (e.g., patient) is present. As a result, it is possible to secure the privacy of the information providing side, to prevent leakage of confidential information, and the like.

Note that in the present embodiment, the authentication result is obtained as success of authentication in the case where the first position information and the second position information are less than or equal to a predetermined distance (or less than the predetermined distance) from each other. However, it is possible that the authentication result is obtained as success of authentication in the case where the first position information and the second position information are greater than or equal to a predetermined distance (greater than the predetermined distance) from each other. In this case, it is possible to reference information in the absence of a person to whom the information should not be disclosed. In addition, as described above, it is also possible that the authentication result is obtained as success of authentication in the case where the first position information and the second position information both indicate a point within a predetermined region. In this case, the region applied to the first position information and the region applied to the second position information may be different. Furthermore, it is also possible that the authentication result is obtained as success of authentication in the case where the first position information and the second position information both indicate a point outside a predetermined region. In this case as well, the region applied to the first position information and the region applied to the second position information may be different.

Embodiment 3

In the present embodiment, an information processing system 4 that can change information to be output according to the authentication method will be described. An information processing system 1 that can change information to be output according to the position information of a terminal will be also described. In addition, an information processing system 4 that can change information to be output according to the medical procedure information will be also described.

FIG. 17 is a conceptual diagram of the information processing system 4 of the present embodiment. The information processing system 4 includes a terminal apparatus 171, a second terminal 172, and a server 173. The terminal apparatus 171 and the second terminal 172 are, for example, a so-called personal computer and a portable terminal (including a mobile phone). The server 173 is a device that is capable of communication with the terminal apparatus 171 and the second terminal 172, and that performs authentication processing. Note that the second terminal 172 is not essential for the information processing system 4. Specifically, the information processing system 4 may be configured by the terminal apparatus 171 and the server 173.

FIG. 18 is a block diagram of the information processing system 4 of the present embodiment.

The terminal apparatus 171 includes a terminal accepting unit 1711, a position information acquiring unit 1712, a terminal sending unit 1713, a terminal receiving unit 1714, and a terminal output unit 1715.

The second terminal 172 includes a second accepting unit 1721, a second sending and receiving unit 1722, and a second output unit 1723.

The server 173 includes an information storage unit 1731, an authentication information receiving unit 1732, an authentication unit 1733, a terminal position information receiving unit 1734, a medical procedure information receiving unit 1735, an information acquiring unit 1736, an authentication result sending unit 1737, and an information sending unit 1738.

The authentication unit 1733 includes a first authentication section 17331, a second authentication section 17332, and a third authentication section 17333.

The terminal accepting unit 1711 accepts an input from a user. The terminal accepting unit 1711 accepts an input of a command to execute processing that requires authentication processing. The command is, for example, a command to log into the server 173 or a command to access the server 173. The terminal accepting unit 1711 accepts, for example, authentication information. The authentication information is necessary for authentication processing. The authentication information is normally input by a user. The authentication information is, for example, a user ID and a password. Also, the authentication information may include two IDs, for example.

The authentication information and the like may be input by any means such as a keyboard, a mouse, a numerical keypad, and a menu screen. The accepting unit 1711 can be realized by a device driver of the input means such as a keyboard, menu screen control software, or the like.

The position information acquiring unit 1712 acquires position information that indicates the current position of the terminal apparatus 171. The position information is, for example, information of (latitude, longitude). Also, the position information is, for example, information that specifies a place (e.g., address, place names, and the like). The position information acquiring unit 1712 is, for example, a GPS receiver. Also, the position information acquiring unit 1712 may acquire the position information according to the radio wave reception state from three base stations of the mobile phone, for example. Also, the position information acquiring unit 1712 receives information that specifies a place by a close-range wireless communication means, for example.

The terminal sending unit 1713 sends information or commands accepted by the terminal accepting unit 1711, the position information acquired by the position information acquiring unit 1712, and the like to the server 173. The terminal sending unit 1713 is generally realized by a wireless or wired communication means, but may also be realized by a broadcasting means.

The terminal receiving unit 1714 receives information such as the authentication result or output information from the server 173. The output information is information to be output to the terminal apparatus 171. There is no restriction to the content of the output information. Examples of the output information include, medical record information of patients, information included in the diary of users, information relating to the privacy of users, and the like. The terminal receiving unit 1714 is generally realized by a wireless or wired communication means, but may be realized by a means for receiving broadcasting. Note that in the case where the terminal receiving unit 1714 receives the output information, the terminal receiving unit 1714 may be referred to as an output information receiving unit.

The terminal output unit 1715 outputs information received by the terminal receiving unit 1714 (e.g., authentication result, output information and the like). Here, "output" represents a concept that includes output to a display, projection by a projector, printing with a printer, output of a sound, sending to an outside device, accumulation in a recording medium, and delivery of processing results to other processing apparatuses or programs. The terminal output unit 1715 may or may not include an output device such as a display or a speaker. The terminal output unit 1715 can be realized by a driver software of an output device, or a driver software of an output device and an output device, etc. Note that in the case where the terminal output unit 1715 outputs the output information, the terminal output unit 1715 may be referred to as an output information output unit.

The second accepting unit 1721 accepts an input from the user of the second terminal 172. For example, the second accepting unit 1721 accepts an ID from the user of the second terminal 172. In this case, any input means such as a keyboard, a mouse, a numerical keypad, and a menu screen may be used. The second accepting unit 1721 can be realized by a device driver of the input means such as a keyboard, menu screen control software, or the like.

The second sending and receiving unit 1722 sends information (input) accepted by the second accepting unit 1721 to the server 173. Also, the second sending and receiving unit 1722 receives information from the server 173. The second sending and receiving unit 1722 is generally realized by a wireless or wired communication means, but may also be realized by a broadcasting means.

The second output unit 1723 outputs information received from the server 173. The second output unit 1723 may or may not include an output device such as a display or a speaker. The second output unit 1723 can be realized by a driver software of an output device, or a driver software of an output device and an output device, etc.

In the information storage unit 1731, two or more pieces of output information that are associated with at least one of two or more different authentication methods are stored. The "output information associated with the authentication method" refers to, for example, output information that is paired with at least one authentication method identification information that identifies the authentication method. The "output information associated with the authentication method" may be any information as long as output information to be acquired is decided upon decision of the authentication method. The information storage unit 1731 is preferably a non-volatile recording medium, but it can be realized also by a volatile recording medium.

There is no restriction to the process by which the output information is stored in the information storage unit 1731. For example, the output information may be stored in the region information storage section 1731 via a recording medium, or the output information sent via a communication line or the like may be stored in the region information storage section 1731. Alternatively, the output information input via an input device may be stored in the region information storage section 1731.

The authentication information receiving unit 1732 receives, from the terminal apparatus 171, the authentication information used for authentication processing and the authentication method identification information. The authentication information receiving unit 1732 is generally realized by a wireless or wired communication means, but may be realized by a means for receiving broadcasting.

The authentication unit 1733 performs authentication processing by executing one of two or more different authentication methods by using the authentication information received by the authentication information receiving unit 1732, the one authentication method being identified by the authentication method identification information received by the authentication information receiving unit 1732. That is, the authentication unit 1733 can perform authentication processing according to two or more different authentication methods. The authentication unit 1733 includes two or more authentication sections. Here, description will be given assuming that the authentication unit 1733 mainly includes the first authentication section 17331, the second authentication section 17332 and the third authentication section 17333. The two or more authentication sections use mutually different authentication methods. In addition, there may be cases in which the authentication unit 1733 performs authentication processing using two or more pieces of authentication information. The authentication unit 1733 can be generally realized by an MPU, memory or the like. The processing procedure of the authentication unit 1733 is generally realized by software, and the software for this is recorded in a recording medium such as a ROM. Note that the processing procedure also may be realized by hardware (dedicated circuitry).

The first authentication section 17331 performs authentication by using, for example, authentication information made up of the ID and the password of the terminal apparatus 171. That is, the first authentication section 17331 has stored therein one or more sets of an ID and a password, and searches for the set that matches the ID and the password included in the authentication information received by the authentication information receiving unit 1732. The first authentication section 17331 determines the authentication result to be success of authentication if the matching set is found and determines the authentication result to be failure of authentication if the matching set is not found, so as to acquire information corresponding to the authentication result (for example, "1" is acquired in the case of success of authentication, and "0" is acquired in the case of failure of authentication). Note that the sets of ID and password may be held by the data storage unit 1731, for example.

The second authentication section 17332 performs authentication processing by using, for example, authentication information made up of the ID and the password of the terminal apparatus 171 and second authentication information sent to the second terminal 172 (temporary authentication information). That is, for example, the second authentication section 17332 has stored therein one or more sets of an ID and a password, and searches for the set that matches the ID and the password included in the authentication information received by the authentication information receiving unit 1732, and sends the second authentication information to the second terminal 172 if the matching set is found. Then, if the second authentication information has been sent from the terminal apparatus 171, the second authentication section 17332 determines that the authentication result is success of authentication. In contrast, if there is no matching set, or if the second authentication information sent from the terminal apparatus 171 does not match the second authentication information sent to the second terminal 172, the second authentication section 17332 determines the authentication result to be failure of authentication.

The third authentication section 17333 performs authentication processing by using, for example, authentication information made up of two IDs and two passwords of the terminal apparatus 171, and the second authentication information (temporary authentication information) sent to the second terminal 172. Note that for example, the third authentication section 17333 performs the first authentication processing by using first ID and password, and then performs the second authentication processing by using the second ID and password and the second authentication information.

Note that in the description given above, when the authentication method performed by the first authentication section 17331 is the "method 1", the authentication method performed by the second authentication section 17332 is the "method 2", and the authentication method performed by the third authentication section 17333 is the "method 3", the degree of the security (security level) gets more strict (increases) in the following order: method 1<method 2<method 3. Note that "the security level of the second authentication method is higher than that of the first authentication method" means that, for example, the number of data pieces or the number of types of data input by a user is larger in the second authentication method than in the first authentication method. With respect to the types of data, the ID and the password are different types of data. "The security level of the second authentication method is higher than that of the first authentication method" also means that, for example, the number of terminals used is larger in the second authentication method than in the first authentication method. "The security level of the second authentication method is higher than that of the first authentication method" also means that, for example, the security level of the terminal used is higher than in the first authentication method. The security level of mobile phones is higher than the security level of so-called PCs, since the users of mobile phones are identified through the operation.

The first authentication section 17331, the second authentication section 17332, and the third authentication section 17333 can be generally realized by an MPU, memory or the like. The processing procedure of the first authentication section 17331 and the like is generally realized by software, and the software for this is recorded in a recording medium such as a ROM. Note that the processing procedure also may be realized by hardware (dedicated circuitry).

The terminal position information receiving unit 1734 receives position information that indicates the position of the terminal apparatus 171 from the terminal apparatus 171. The terminal position information receiving unit 1734 is generally realized by a wireless or wired communication means, but may be realized by a means for receiving broadcasting.

The medical procedure information receiving unit 1735 receives medical procedure information including a doctor identifier or emergency information from the terminal apparatus 171. The doctor identifier may be any information as long as it can identify the doctor, such as a doctor's ID, a doctor's name, or the like. The emergency information is information that indicates the emergency level of the medical procedure. The medical procedure information receiving unit 1735 is generally realized by a wireless or wired communication means, but may be realized by a means for receiving broadcasting.

If the result of execution performed by the authentication unit 1733 is success of authentication, the information acquiring unit 1736 acquires one or more pieces of output information that correspond to the authentication method identification information. Normally, the lower the security level of the authentication method indicated by the authentication method identification information, the lower the confidentiality of the output information acquired by the information acquiring unit 1736. Also, if the result of execution performed by the authentication unit 1733 is success of authentication, the information acquiring unit 1736 may acquire one or more pieces of output information that correspond to the authentication method identification information and the position information. Also, if the result of execution performed by the authentication unit 1733 is success of authentication, the information acquiring unit 1736 may acquire one or more pieces of output information that correspond to the authentication method identification information and the medical procedure information. In addition, if the result of execution performed by the authentication unit 1733 is success of authentication, the information acquiring unit 1736 may acquire one or more pieces of output information that correspond to the authentication method identification information, and at least one of the position information and the medical procedure information. The information acquiring unit 1736 can be generally realized by an MPU, memory or the like. The processing procedure of the information acquiring unit 1736 is generally realized by software, and the software for this is recorded in a recording medium such as a ROM. Note that the processing procedure also may be realized by hardware (dedicated circuitry).

The authentication result sending unit 1737 sends the authentication result (final authentication result) acquired by the authentication unit 1733 to the terminal apparatus 171. The authentication result sending unit 1737 is generally realized by a wireless or wired communication means, but may also be realized by a broadcasting means.

The information sending unit 1738 sends the output information acquired by the information acquiring unit 1736 to the terminal apparatus 171. The information sending unit 1738 is generally realized by a wireless or wired communication means, but may also be realized by a broadcasting means.

Next, an operation of the information processing system 4 will be described. First, an operation of the terminal apparatus 171 will be described with reference to the flowchart shown in FIG. 19.

(Step S1901) The terminal accepting unit 1711 determines whether an input of a command to execute processing that requires authentication processing has been accepted. The procedure proceeds to step S1902 if an input of the command has been accepted, and if not, the procedure returns to step S1901. Note that the command includes authentication method identification information that identifies the authentication method. For example, icons corresponding to the authentication screens for the respective authentication methods are displayed on the screen of the terminal apparatus 171, and the user inputs a command that includes the authentication method identification information by selecting and indicating (e.g., double-clicking) one of the icons.

(Step S1902) The terminal output unit 1715 outputs an authentication screen corresponding to the authentication method identification information included in the command accepted in step S1901. Note that for example, the terminal output unit 1715 holds information corresponding to the authentication screen (for example, definition information of the authentication screen) in advance, and reads in the information so as to configure and output the authentication screen.

(Step S1903) The terminal accepting unit 1711 determines whether authentication information has been accepted. If the authentication information has been accepted, the procedure proceeds to step S1904, and if not, the procedure returns to step S1903.

(Step S1904) The terminal sending unit 1713 sends the authentication information and the like. The authentication information and the like refer to, for example, information that includes the authentication information accepted in step S1903, and the authentication method identification information included in the command accepted in step S1901.

(Step S1905) The terminal receiving unit 1714 determines whether the authentication result has been received in response to sending of the authentication information and the like in step S1904. If the authentication result has been received, the procedure proceeds to step S1906, and if not, the procedure returns to step S1905.

(Step S1906) The terminal output unit 1715 outputs the authentication result received in step S1905. Note that the processing for outputting the authentication result is not essential.

(Step S1907) The terminal accepting unit 1711 determines whether the authentication result received in step S1905 is success of authentication. If the authentication result is success of authentication, the procedure proceeds to step S1908, and if not, the procedure returns to step S1901.

(Step S1908) The terminal accepting unit 1711 determines whether an input from the user has been accepted. The input referred to here is a command to acquire information from the server 173. If the input has been accepted, the procedure proceeds to step S1909, and if not, the procedure returns to step S1908.

(Step S1909) The position information acquiring unit 1712 acquires position information that indicates the current position of the terminal apparatus 171.

(Step S1910) The terminal sending unit 1713 configures an information acquisition command that includes the position information acquired in step S1909, and sends the information acquisition command to the server 173. Note that the information acquisition command is a command to acquire information from the server 173.

(Step S1911) The terminal receiving unit 1714 determines whether output information has been received from the server 173 in response to sending of the information acquisition command in step S1910. If the output information has been received, the procedure proceeds to step S1912, and if not, the procedure returns to step S1911.

(Step S1912) The terminal output unit 1715 outputs the output information received in step S1911. Then, the procedure returns to step S1901.

Note that in the flowchart shown in FIG. 19, the processing ends due to powering off or interruption for aborting the processing.

Next, an operation performed by the second terminal 172 will be described. The second accepting unit 1721 of the second terminal 172 accepts an input from the user of the second terminal 172. Then, the second sending and receiving unit 1722 sends information (input) accepted by the second accepting unit 1721 to the server 173. The second sending and receiving unit 1722 may receive information from the server 173. Then, the second output unit 1723 outputs the information received by the second sending and receiving unit 1722. Note that the information output here is information necessary for authentication.

Next, an operation of the server 173 will be described with reference to the flowchart shown in FIG. 20.

(Step S2001) The authentication information receiving unit 1732 determines whether authentication information has been received from the terminal apparatus 171, or the terminal apparatus 171 and the second terminal 172. If the authentication information has been received, the procedure proceeds to step S2002, and if not, the procedure proceeds to step S2005. Note that the authentication information includes, for example, authentication method identification information that identifies the authentication method. Also, the authentication information normally includes the user ID that identifies the user (e.g., patient).

(Step S2002) The authentication unit 1733 performs authentication processing that corresponds to the authentication method identification information included in the authentication information received by the authentication information receiving unit 1732, and acquires the authentication result. An example of the details of the authentication processing is as described above.

(Step S2003) The authentication result sending unit 1737 sends the authentication result acquired in step S2002 to the terminal apparatus 171.

(Step S2004) The authentication unit 1733 associates the authentication method identification information with the user ID, and temporarily stores the authentication method identification information and the user ID in a recording medium (not shown). Then, the procedure returns to step S2001.

(Step S2005) The terminal position information receiving unit 1734 and/or the medical procedure information receiving unit 1735 determines whether an information acquisition command has been received from the terminal apparatus 171. If the information acquisition command has been received, the procedure proceeds to step S2006, and if not, the procedure returns to step S2001. Note that the information acquisition command received here generally includes a user ID, and may include position information, medical procedure information and the like.

(Step S2006) The information acquiring unit 1736 acquires position information from the information acquisition command received in step S2005. Note that there may be cases where the position information cannot be acquired.

(Step S2007) The information acquiring unit 1736 acquires medical procedure information from the information acquisition command received in step S2005. Note that there may be cases where the medical procedure information cannot be acquired.

(Step S2008) The information acquiring unit 1736 reads out the temporarily stored authentication method identification information.

(Step S2009) The information acquiring unit 1736 searches the information storage unit 1731 using the user ID, the authentication method identification information and the like included in the information acquisition command, and acquires output information on a memory. Note that the authentication method identification information and the like include, in addition to the authentication method identification information, the position information, the medical procedure information, or the position information and the medical procedure information, and the like, for example. Also, the authentication method identification information and the like may further include time information. The time information indicates the time at which the information acquisition command sent from the terminal apparatus 171 was received, and is acquired from, for example, an unshown clock or an external server (e.g., NTP server).

(Step S2010) The information sending unit 1738 sends the output information acquired in step S2009 to the terminal apparatus 171. Then, the procedure returns to step S2001.

Note that in the flowchart shown in FIG. 20, the processing ends due to powering off or interruption for aborting the processing.

A specific operation of the information processing system 4 of the present embodiment will be described below. The conceptual diagram of the information processing system 4 is shown in FIG. 1.

The information storage unit 1731 holds a medical record information management table shown in FIG. 21. The medical record information management table manages information such as medical history of patients (medical record information) and information necessary for authentication. The medical record information management table holds one or more records, each record including "No.", "First authentication information", "Second authentication information", "Terminal identification information", and "Output information". "No" is information that identifies the record. "First authentication information" includes "ID1" and "PW1" that are used by the first authentication section 17331, the second authentication section 17332 and the third authentication section 17333. "Second authentication information" includes "ID2" and "PW2" that are used only by the third authentication section 17333. "ID1" and "ID2" are IDs necessary for logging into or accessing the server 173. "ID1" is the user ID, in this case. "PW1" and "PW2" are passwords necessary for logging into or accessing the server 173. "Terminal identification information" is information that identifies the second terminal 172, and here it is the telephone number of the second terminal 172. Note that here, the second terminal 172 is a so-called mobile phone. "Output information" includes attributes of the user (patient) of the second terminal 172, medical record information (medical information), which is information related to diseases, of the user (patient), and the like.

A search condition management section (not shown) of the authentication unit 1733 has stored therein a search condition management table shown in FIG. 22. The search condition management table is a control table in which information is managed that is for deciding output information to be output with respect to the conditions, each condition including one or more of the authentication method identification information, the position information and the medical procedure information. Two or more records are stored in the search condition management table, each record including attribute values of "Condition information" and "Information not to be output". "Condition information" is an attribute having information that indicates search conditions as its attribute values, and includes the attributes "authentication method identification information", "position information", and "medical procedure information". In this case, in the attribute "position information", in the case where the position information indicating the position of the terminal apparatus 171 corresponds to a place that the user (patient) has registered, the attribute value "registered place" is matched, and if the position information does not correspond to any place registered by the user, the attribute value "unregistered place" is matched. In the attribute "medical procedure information", emergency information or information that classifies doctors is stored. The emergency information indicates an emergency level for performing a medical procedure, and in this case, can have a value "normal" or "emergency". The information that classifies doctors can have a value "patient's doctor" or "not patient's doctor". In the case where a condition indicated by the "condition information" is matched in the search condition management table, all attribute values or specific attribute values of the corresponding attributes indicated by the attribute "Information not to be output" are not searched for. Also, in the search condition management table, the symbol "-" means "no information".

Then, the first record of the search condition management table shown in FIG. 22 indicates that in the case where the authentication method identification information "method 1", the position information "unregistered place", and the medical procedure information "normal" are matched, all attribute values of "medical history", information relating to "stomach cancer" out of the attribute values of "disease under treatment", and all attribute values of "treatment history of cancer" will not be acquired.

Also, in the search condition management table shown in FIG. 22, it is indicated that in the case where the authentication method identification information "method 1", the position information "unregistered place", and the medical procedure information "emergency" are matched, all attribute values of "treatment history of cancer" will not be acquired.

Also, in the search condition management table shown in FIG. 22, it is indicated that in the case where the authentication method identification information "method 1", the position information "registered place", and the medical procedure information "patient's doctor" are matched, all output information will be acquired.

Also, in the search condition management table shown in FIG. 22, it is indicated that in the case where the authentication method identification information "method 2", the position information "unregistered place", the medical procedure information "normal" are matched, all attribute values of "medical history" and "treatment history of cancer" will not be acquired.

Also, in the search condition management table shown in FIG. 22, it is indicated that in the case where the authentication method identification information "method 2" and the position information "registered place" are matched, all output information will be acquired.

Also, in the search condition management table shown in FIG. 22, it is indicated that in the case where the authentication method identification information "method 3" is matched, all output information will be acquired.

A registration information management section (not shown) of the authentication unit 1733 has stored therein a registration information management table shown in FIG. 23. One or more records can be stored in the registration information management table, each record including attribute values of "No", "User ID", "Registered place", and "ID of patient's doctor". "No" is information that identifies the record. "User ID" is the user ID of a patient. "Registered place" includes position information that specifies the place of the patient's hospital. In this case, the "registered place" is specified by (latitude, longitude) corresponding to the northwest (upper left) point and (latitude, longitude) corresponding to the southeast (lower right) point, and the place of the patient's hospital is specified as a rectangular region. Note that a patient can register two or more places. "ID of patient's doctor" is information that identifies the patient's doctor. Note that although each record in the registration information management table is generally registered by the user, there is no restriction to the process for the registration.

In this state, three specific examples will be described below.

Example 1

It is assumed that a user 1 (Akiko Tanaka) has visited a hospital A that she usually visits to see her doctor X for examination. It is assumed that the doctor X has attempted to acquire the medical record information of the user 1 from the server 173 using the terminal apparatus 171 installed in the hospital A. Then, it is assumed that the button of "Authentication method 1", which is a simple authentication method, has been pressed on the screen of the terminal apparatus 171 shown in FIG. 24.

The terminal accepting unit 1711 accepts a command including the authentication method identification information "method 1" (e.g., a command to log into the server 173).

Next, the terminal output unit 1715 outputs an authentication screen (FIG. 25) that corresponds to the authentication method identification information "method 1" included in the accepted command.

Then, it is assumed that the user 1 or the doctor X has input the ID "5631" and the PW "abc" and has pressed the "Login" button in order to access the medical record information of the user 1. Note that for example, it is also possible that the doctor X may acquire the ID "5631" and the PW "abc" from the user 1 and input them.

Then, the terminal sending unit 1713 configures authentication information "authentication method identification information: method 1, ID: 5631, PW: abc", and sends the authentication information to the server 173.

The authentication information receiving unit 1732 of the server 173 receives the authentication information "authentication method identification information: method 1, ID: 5631, PW: abc".

Then, the authentication unit 1733 calls the first authentication section 17331 based on "method 1" included in the authentication information received by the authentication information receiving unit 1732, and forwards "ID: 5631, PW: abc" to the first authentication section 17331.

Next, the first authentication section 17331 determines whether there is first authentication information that matches "ID: 5631, PW: abc" in the medical record information management table shown in FIG. 21. The first authentication section 17331 determines that the record of "No=1" in the medical record information management table in FIG. 21 matches "ID: 5631, PW: abc".

Then, the authentication unit 1733 acquires an authentication result "success of authentication".

Next, the authentication result sending unit 1737 sends the acquired authentication result "success of authentication" to the terminal apparatus 171.

Then, the authentication unit 1733 temporarily stores the authentication method identification information "method 1" in an unshown recording medium in association with the user ID "5631".

Next, the terminal receiving unit 1714 receives the authentication result "success of authentication" in response to sending of the authentication information and the like. Then, the terminal output unit 1715 outputs the authentication result "success of authentication".

Next, it is assumed that the user 1 or the doctor X inputs a command to acquire information to the terminal apparatus 171 before starting examination. Here, the command to acquire information is assumed to include the user ID "5631" and the doctor identifier "236100" of the doctor X. The command to acquire information is also assumed to include the emergency information "normal".

Next, the position information acquiring unit 1712 acquires the position information (Xa, Ya) that indicates the current position of the terminal apparatus 171.

Next, the terminal sending unit 1713 configures an information acquisition command that includes the acquired position information (Xa, Ya), the doctor identifier "236100", and the emergency information "normal", and sends the information acquisition command to the server 173. Note that the information acquisition command is a command to acquire information from the server 173. Here, the information acquisition command is, for example, "send_info 5631, (Xa, Ya), 236100, normal".

Next, the server 173 receives the information acquisition command "send_info 5631, (Xa, Ya), 236100, normal" from the terminal apparatus 171.

Next, the information acquiring unit 1736 acquires the user ID "5631", the position information (Xa, Ya), the medical procedure information (the doctor identifier "236100" and the emergency information "normal") from the received information acquisition command.

Next, the information acquiring unit 1736 reads out the temporarily stored authentication method identification information "method 1" that corresponds to the user ID "5631".

Next, the information acquiring unit 1736 acquires output information using the user ID "5631", the authentication method identification information "method 1", the position information (Xa, Ya), and the medical procedure information (the doctor identifier "236100" and the emergency information "normal") that are included in the information acquisition command. That is, the information acquiring unit 1736 first determines that the position information (Xa, Ya) is included in the region of the registered place "$(x_1, y_1)$, $(x_2, y_2)$" that is paired with the user ID "5631", and acquires the position information "registered place". Note that a technique for determining whether a certain position is included in a certain region is a known technique, such a technique will not be described in detail here. Also, the information acquiring unit 1736 determines that the doctor identifier "236100" included in the medical procedure information matches the ID of the patient's doctor that is paired with the user ID "5631" in the registration information management table in FIG. 22, and acquires the medical procedure information "patient's doctor". Next, the information acquiring unit 1736 applies the authentication method identification information "method 1", the position information "registered place", and the medical procedure information "patient's doctor" to the registration information management table in FIG. 22, and determines that no information is prohibited from being output ("-"). Then, the information acquiring unit 1736 reads out all output information that corresponds to the user ID "5631", namely, "Name: Akiko Tanaka, Age: 48, Sex: female, Medical history: appendicitis (age 20), gastric ulcer (age 28), diabetes (age 30 to present), Disease under treatment: diabetes, Treatment history of cancer: no, etc.", and loads the output information on a memory.

Then, the information sending unit 1738 sends the acquired output information to the terminal apparatus 171.

Next, in response to sending of the information acquisition command, the terminal receiving unit 1714 receives, from the server 173, the output information "Name: Akiko Tanaka, Age: 48, Sex: female, Medical history: appendicitis (age 20), gastric ulcer (age 28), diabetes (age 30 to present), Disease under treatment: diabetes, Treatment history of cancer: no, etc.".

Next, the terminal output unit 1715 outputs the received output information as shown in FIG. 26. In this state, the doctor X, who is the patient's doctor, can perform appropriate medical practice while referencing all the medical record information of the patient (Akiko Tanaka). That is, since the doctor who performs medical practice is the patient's doctor whom she trusts, the user 1 can allow the doctor to perform medical practice while promptly acquiring her medical record information from the server 173 with a simple authentication method, and showing all the medical record information (output information) including confidential information to the doctor.

Example 2

Next, it is assumed that the user 1 (Akiko Tanaka) suddenly has become ill in the night and has visited the hospital A that she usually visits, and that doctor Y of the hospital A (who is not the doctor of the user 2) sees the user 1. It is assumed that at that time, the doctor Y attempts to acquire the medical record information of the user 1 using the terminal apparatus 171 installed in the hospital A from the server 173. Then, it is assumed that the button of "Authentication method 1", which is a simple authentication method, has been pressed on the screen of the terminal apparatus 171 shown in FIG. 24.

The terminal accepting unit 1711 accepts a command including the authentication method identification information "method 1" (for example, a command to log into the server 173).

Next, the terminal output unit 1715 outputs an authentication screen (FIG. 25) that corresponds to the authentication method identification information "method 1" included in the accepted command.

Then, it is assumed that the user 1 or the doctor Y has the input ID "5631" and the PW "abc" and has pressed the "Login" button in order to access the medical record information of the user 1. Note that, for example, the doctor X may acquire the ID "5631" and the PW "abc" from the user 1 and input them.

Then, the terminal sending unit 1713 configures authentication information "authentication method identification information: method 1, ID: 5631, PW: abc", and sends the authentication information to the server 173.

The authentication information receiving unit 1732 of the server 173 receives the authentication information "authentication method identification information: method 1, ID: 5631, PW: abc".

Then, the authentication unit 1733 calls the first authentication section 17331 based on "method 1" included in the authentication information received by the authentication information receiving unit 1732, and forwards "ID: 5631, PW: abc" to the first authentication section 17331.

Next, the first authentication section 17331 determines whether there is first authentication information that matches "ID: 5631, PW: abc" in the medical record information management table shown in FIG. 21. The first authentication section 17331 determines that the record of "No=1" in the medical record information management table in FIG. 21 matches "ID: 5631, PW: abc".

Then, the authentication unit 1733 acquires an authentication result "success of authentication".

Next, the authentication result sending unit 1737 sends the acquired authentication result "success of authentication" to the terminal apparatus 171.

Then, the authentication unit 1733 temporarily stores the authentication method identification information "method 1" in an unshown recording medium in association with the user ID "5631".

Next, the terminal receiving unit 1714 receives the authentication result "success of authentication" in response to sending of the authentication information and the like. Then, the terminal output unit 1715 outputs the authentication result "success of authentication".

Next, it is assumed that the user 1 or the doctor Y inputs a command to acquire information to the terminal apparatus 171 before starting examination. Here, the command to acquire information is assumed to include the user ID "5631" and the doctor identifier "721503" of the doctor Y. The command to acquire information is also assumed to include the emergency information "normal".

Next, the position information acquiring unit 1712 acquires the position information (Xa, Ya) that indicates the current position of the terminal apparatus 171.

Next, the terminal sending unit 1713 configures an information acquisition command that includes the acquired position information (Xa, Ya), the doctor identifier "721503", and the emergency information "normal", and sends the information acquisition command to the server 173. Note that the information acquisition command is a command to acquire information from the server 173. Here, the information acquisition command is, for example, "send_info 5631, (Xa, Ya), 721503, normal".

Next, the server 173 receives the information acquisition command "send_info 5631, (Xa, Ya), 721503, normal" from the terminal apparatus 171.

Next, the information acquiring unit 1736 acquires the user ID "5631", the position information (Xa, Ya), the medical procedure information (the doctor identifier "721503" and the emergency information "normal") from the received information acquisition command.

Next, the information acquiring unit 1736 reads out the temporarily stored authentication method identification information "method 1" that corresponds to the user ID "5631".

Next, the information acquiring unit 1736 acquires output information by using the user ID "5631", the authentication method identification information "method 1", the position information (Xa, Ya), and the medical procedure information (the doctor identifier "721503" and the emergency information "normal") that are included in the information acquisition command. That is, the information acquiring unit 1736 first determines that the position information (Xa, Ya) is included in the region of the registered place "$(x_1, y_1)$, $(x_2, y_2)$" that is paired with the user ID "5631", and acquires the position information "registered place". Also, the information acquiring unit 1736 determines that the doctor identifier "721503" included in the medical procedure information does not match the ID of the patient's doctor that is paired with the user ID "5631" in the registration information management table in FIG. 22, and acquires the medical procedure information "not patient's doctor". Next, the information acquiring unit 1736 applies the authentication method identification information "method 1", the position information "registered place", and the medical procedure information "not patient's doctor" to the registration information management table in FIG. 22, and determines that all information of the attributes "medical history" and "treatment history of cancer" will not be output. Then, the information acquiring unit 1736 reads out output information that corresponds to the user ID "5631" and that does not include the attribute values of the "medical history" and the "treatment history of cancer", namely, "Name: Akiko Tanaka, Age: 48, Sex: female, Disease under treatment: diabetes, etc.", and loads the output information on a memory.

Then, the information sending unit 1738 sends the acquired output information to the terminal apparatus 171.

Next, in response to sending of the information acquisition command, the terminal receiving unit 1714 receives, from the server 173, the output information "Name: Akiko Tanaka, Age: 48, Sex: female, Disease under treatment: diabetes, etc." in response to sending of the information acquisition command.

Next, the terminal output unit 1715 outputs the received output information as shown in FIG. 27. In this state, the doctor Y can perform necessary medical practice while referencing part of the medical record information of the patient (Akiko Tanaka), and preventing leakage of confidential information of the patient.

Example 3

Next, it is assumed that a user 2 (Kazuo Yamada) has become ill when he is walking on the street, and has been put in the ambulance. It is also assumed that an ambulance crew member Z has attempted to reference the medical record information of the user 2 using the terminal apparatus 171 disposed in the ambulance car.

That is, it is assumed that the ambulance crew member Z has pressed the button of "Authentication method 2", which is a normal authentication method, on the screen of the terminal apparatus 171 disposed in the ambulance car.

The terminal accepting unit 1711 accepts a command including the authentication method identification information "method 2" (for example, a command to log into the server 173).

Next, the terminal output unit 1715 outputs an authentication screen (FIG. 24) that corresponds to the authentication method identification information "method 2" included in the accepted command.

Then, it is assumed that the ambulance crew member Z has input the ID "1221" and the PW "xy3" and has pressed the "Login" button in order to access the medical record information of the user 2. Note that for example, the ambulance crew member Z acquires the ID "1221" and the PW "xy3" from the user 2 and inputs them.

Then, the terminal sending unit 1713 configures authentication information "authentication method identification information: method 2, ID: 1221, PW: xy3", and sends the authentication information to the server 173.

The authentication information receiving unit 1732 of the server 173 receives the authentication information "authentication method identification information: method 2, ID: 1221, PW: xy3".

Then, the authentication unit 1733 calls the second authentication section 17332 based on "method 2" included in the authentication information received by the authentication information receiving unit 1732, and forwards "ID: 1221, PW: xy3" to the second authentication section 17332.

Next, the second authentication section 17332 determines whether there is first authentication information that matches "ID: 1221, PW: xy3" in the medical record information management table shown in FIG. 21. The second authentication section 17332 determines that the record of "No=2" in the medical record information management table in FIG. 21 matches "ID: 1221, PW: xy3".

Then, the second authentication section 17332 automatically configures second authentication information (temporary authentication information). Note that it is assumed that the second authentication section 17332 has executed f(1221, xy3) by using "ID: 1221, PW: xy3", and has configured second authentication information (a85bq9), for example. Then, the second authentication section 17332 temporarily stores the second authentication information (a85bq9) in a storage section (not shown).

Next, the second authentication section 17332 reads out terminal identification information "080-7788-1234" in the record of "ID=2" from the table shown in FIG. 21.

Then, the authentication result sending unit 1737 sends the second authentication information (a85bq9) to the second terminal 172 identified by the terminal identification information "080-7788-1234".

Also, the authentication result sending unit 1737 sends a processing result of the first authentication processing, "success of authentication", to the terminal apparatus 171.

The second sending and receiving unit 1722 of the second terminal 172 receives the second authentication information (a85bq9) from the server 173. Then, the second output unit 1723 outputs the second authentication information (a85bq9) received from the server 173. FIG. 27 is an example of the second authentication information output to the second terminal 12.

Next, the terminal receiving unit 1714 of the terminal apparatus 171 receives the processing result of the first authentication processing, "success of authentication".

Then, the terminal output unit 1715 outputs a second authentication screen for performing second authentication. The second authentication screen is shown in FIG. 28.

Then, the ambulance crew member Z inputs the second authentication information (a85bq9) in the input field of the second authentication screen in FIG. 28, and presses the "Send" button.

The terminal accepting unit 1711 accepts the second authentication information (a85bq9), and the terminal sending unit 1713 sends the second authentication information (a85bq9) accepted by the terminal accepting unit 1711 to the server 173.

Next, the authentication information receiving unit 1732 of the server 173 receives the second authentication information (a85bq9) from the terminal apparatus 171.

Next, the second authentication section 17332 determines whether the second authentication information (a85bq9) matches the temporarily stored second authentication information. Here, since both information pieces match, the second authentication section 17332 decides the final authentication result to be "success of authentication". Then, the authentication unit 1733 acquires the authentication result "success of authentication".

Next, the authentication result sending unit 1737 sends the acquired authentication result "success of authentication" to the terminal apparatus 171.

Then, the authentication unit 1733 temporarily stores the authentication method identification information "method 2" in an unshown recording medium in association with the user ID "1221".

Next, the terminal receiving unit 1714 receives the authentication result "success of authentication" in response to sending of the authentication information and the like. Then, the terminal output unit 1715 outputs the authentication result "success of authentication".

Next, it is assumed that the user 2 or the ambulance crew member Z inputs a command to acquire information to the terminal apparatus 171 before starting emergency treatment. Here, the command to acquire information is assumed to include the user ID "1221" and the doctor identifier of the ambulance crew member Z "—(none)". The command to acquire information is also assumed to include the emergency information "emergency".

Next, the position information acquiring unit 1712 acquires the position information (Xb, Yb) that indicates the current position of the terminal apparatus 171.

Next, the terminal sending unit 1713 configures an information acquisition command that includes the acquired position information (Xb, Yb), the doctor identifier "-", and the emergency information "emergency", and sends the information acquisition command to the server 173. Note that the information acquisition command is a command to acquire information from the server 173. Here, the information acquisition command is, for example, "send_info 1221, (Xb, Yb), -, emergency".

Next, the server 173 receives the information acquisition command "send_info 1221, (Xb, Yb), -, emergency" from the terminal apparatus 171.

Next, the information acquiring unit 1736 acquires the user ID "1221", the position information (Xb, Yb), the medical procedure information (the doctor identifier "-" and the emergency information "emergency") from the received information acquisition command.

Next, the information acquiring unit 1736 reads out the temporarily stored authentication method identification information "method 2" that corresponds to the user ID "1221".

Next, the information acquiring unit 1736 acquires output information by using the user ID "1221", the authentication method identification information "method 2", the position information (Xb, Yb), and the medical procedure information (the doctor identifier "-" and the emergency information "emergency") that are included in the information acquisition command. That is, the information acquiring unit 1736 first determines that the position information (Xb, Yb) is not included in the region of the registered place "($x_5$, $y_5$), ($x_6$, $y_6$)" that is paired with the user ID "1221", and acquires the position information "unregistered place". Also, the information acquiring unit 1736 determines that the doctor identifier "-" included in the medical procedure information does not match the ID of the patient's doctor that is paired with the user ID "1221" in the registration information management table in FIG. 22, and acquires the medical procedure information "not patient's doctor". Next, the information acquiring unit 1736 applies the authentication method identification information "method 2", the position information "unregistered place", and the medical procedure information "not patient's doctor" and "emergency" to the registration information management table in FIG. 22, and determines that attribute values of the attribute "treatment history of cancer" will not be output. Then, the information acquiring unit 1736 reads out output information that corresponds to the user ID "1221" and that does not include the attribute values of the "treatment history of cancer", namely, "Name: Kazuo Yamada, Age: 34, Sex: male, Medical history: anemia (age 15), hypertension (age 30), Disease under treatment: none, etc.", and loads the output information on a memory.

Then, the information sending unit 1738 sends the acquired output information to the terminal apparatus 171.

Next, in response to sending of the information acquisition command, the terminal receiving unit 1714 receives, from the server 173, the output information "Name: Kazuo Yamada, Age: 34, Sex: male, Medical history: anemia (age 15), hypertension (age 30), Disease under treatment: none, etc.".

Next, the terminal output unit 1715 outputs the received output information "Name: Kazuo Yamada, Age: 34, Sex: male, Medical history: anemia (age 15), hypertension (age 30), Disease under treatment: none, etc.". In this state, the ambulance crew member Z can perform necessary emergency treatment while referencing part of the medical record information of the patient (Kazuo Yamada), and preventing leakage of confidential information of the patient.

As described above, with the present embodiment, it is possible to change information to be output according to the authentication method. Also, with the present embodiment, it is possible to change information to be output according to the position information. Furthermore, with the present embodiment, it is possible to change information to be output according to the medical procedure information (the identifier of the doctor who sees the patient, the emergency level, and the like).

Based on the description given above, with the present embodiment, it is possible to provide information necessary for medical procedure while appropriately securing the privacy of patients.

Note that the operator of the terminal apparatus 171 selects the authentication method in the present embodiment. However, the authentication method may be automatically selected.

Also, with the present embodiment, the output information is mainly the medical record information. However, needless to say, there is no restriction to the content of the output information.

Also, in the present embodiment, it is sufficient that information that corresponds to any of one or more of the authentication method, the position information, and the medical procedure information (information necessary for performing medical practice such as the identifier of the doctor who will see the patient, the emergency level, and the like) is acquired by using information of the one or more of the authentication method, the position information, and the medical procedure information, and the acquired information is output by the terminal apparatus 171. That is, in the present embodiment, it is not necessary to filter the output information using all of the authentication method, the position information and the medical procedure information.

Embodiment 4

In the present embodiment, an information processing system will be described that detects (predicts) that transition to an environment where communication is impossible is likely to be made or is to be made, and automatically downloads information. Also, a function will be described in which it is detected that the terminal apparatus has transitioned to an environment where communication is possible, and the information that has been automatically downloaded is deleted from the terminal apparatus.

Note that although information to be downloaded, output, or the like in the present embodiment is mainly medical record information (also referred to as medical information) of patients that is used in medical setting, the information is not limited to the medical information.

FIG. 29 is a conceptual diagram of an information processing system 5 of the present embodiment. The information processing system 5 includes a server 51 and one or more terminal apparatuses 52. Information provided to the terminal apparatus 52 is stored in the server 51, and the information is sent to the terminal apparatus 52 when needed. The terminal apparatus 52 accumulates information received from the server 51, and outputs the information when needed.

FIG. 30 is a block diagram of the information processing system 5 of the present embodiment. The server 51 includes a terminal information storage unit 511, a sending instruction receiving unit 512, an output information acquiring unit 513, and an output information sending unit 514.

The terminal apparatus 52 includes a terminal identification information storage unit 521, an output information storage unit 522, an accepting unit 523, a non-communication environment detection unit 524, a sending instruction sending unit 525, an output information receiving unit 526, an output information accumulation unit 527, an output information output unit 528, a communication environment detection unit 529, and an output information deletion unit 530.

The non-communication environment detection unit 524 includes a region information storage section 5241, a position information acquiring section 5242, and a non-communication environment detection section 5243.

The sending instruction sending unit 525 includes a sending instruction configuring section 5251 and a sending instruction sending section 5252.

The terminal information storage unit 511 can have stored therein one or more pieces of terminal information. The terminal information is information in which the terminal identification information that identifies a terminal apparatus 52 is associated with output information to be output to the terminal apparatus 52. The output information is, normally, information output by the terminal apparatus 52. The output information is, for example, medical record information including information relating to diseases of the patient. The medical record information can be also referred to as medical information of the patient. The medical information includes, for example, the name, the address, the mobile phone number, the driver's license number, the ID number, medical history of the patient, drugs being taken by the patient, medical history of patient's family members, and the like. The terminal information may be information in which the terminal identification information, the output information and a flag are associated with each other. The flag is information that indicates whether or not to be extracted in the case where the type information included in a sending instruction indicates an automatic sending instruction, or whether or not to be extracted when the type information included in a sending instruction indicates a manual sending instruction. The type information is information that indicates the type of the sending instruction, and indicates whether the sending instruction is a sending instruction (automatic sending instruction) that is sent in the case where the non-communication environment detection unit 524 has detected movement to an environment where communication with the server 51 is impossible, or a sending instruction (manual sending instruction) that is sent in the case where the accepting unit 523 has accepted an output instruction. The flag may be, for example, information for identifying information that is not extracted in the case where the information included in the sending instruction indicates the automatic sending instruction. Generally, the flag is set to not the attribute value, but the attribute. For example, the attribute having a flag is not extracted in the case where the type information included in the sending instruction indicates the automatic sending instruction, and is extracted in the case where the type information included in the sending instruction indicates the manual sending instruction. Also, the flag may be set to specific attribute values only. The flag may be set for each user and each attribute. Furthermore, the flag may be set for each user and each attribute value.

The terminal information storage unit 511 is preferably a non-volatile recording medium, but it can be realized also by a volatile recording medium. There is no restriction to the process by which the terminal information is stored in the terminal information storage unit 511. For example, the terminal information may be stored in the terminal information storage unit 511 via a recording medium, or the terminal information sent via a communication line or the like may be stored in the terminal information storage unit 511. Alternatively, the terminal information input via an input device may be stored in the terminal information storage unit 511.

A sending instruction receiving unit 552 receives a sending instruction from the terminal apparatus 52. The sending instruction is an instruction that includes the terminal identification information that identifies the terminal apparatus 52, and is an instruction to send output information. The sending instruction may include the terminal identification information and the type information. Note that the automatic sending instruction, which is an example of the type information, is "1", for example, and the manual sending instruction is "0", for example. The sending instruction receiving unit 552 is generally realized by a wireless or wired communication means, but may be realized by a means for receiving broadcasting.

In the case where the sending instruction receiving unit 552 has received a sending instruction, the output information acquiring unit 513 acquires output information that is paired with the terminal identification information included in the sending instruction from the terminal information storage unit 511. It is preferable that in the case where the sending instruction receiving unit 552 has received a sending instruction, the output information acquiring unit 513 acquires, from the terminal information storage unit 511, output information that is paired with the terminal identification information included in the sending instruction and that corresponds to the type information included in the sending instruction. Note that the output information that corresponds to the type information is output information acquired by checking the flag. The output information acquiring unit 513 may or may not include an output device such as a display or a speaker. The output information acquiring unit 513 can be realized by a driver software of an output device, or a driver software of an output device and an output device, etc.

The output information sending unit 514 sends the output information acquired by the output information acquiring unit 513 to the terminal apparatus 52. The output information sending unit 514 is generally realized by a wireless or wired communication means, but may also be realized by a broadcasting means.

The terminal identification information storage unit 521 can have stored therein the terminal identification information that identifies the terminal apparatus 52. The terminal identification information is, for example, the telephone number, the MAC address, and the like. The terminal identification information storage unit 521 is preferably a non-volatile recording medium, but it can be realized also by a volatile recording medium. There is no restriction to the process by which the terminal identification information is stored in the terminal identification information storage unit 521. For example, the terminal identification information may be stored in the terminal identification information storage unit 521 via a recording medium, or the terminal identification information sent via a communication line or the like may be stored in the terminal identification information storage unit 521. Alternatively, the terminal identification information input via an input device may be stored in the terminal identification information storage unit 521.

The output information storage unit 522 can have stored therein one or more pieces of output information. The output information storage unit 522 is preferably a non-volatile recording medium, but it can be realized also by a volatile recording medium. There is no restriction to the process by which the output information is stored in the output information storage unit 522. For example, the output information may be stored in the output information storage unit 522 via a recording medium, or the output information sent via a communication line or the like may be stored in the output information storage unit 522. Alternatively, the output information input via an input device may be stored in the output information storage unit 522.

The accepting unit 523 accepts an input of the output instruction. The accepting unit 523 accepts inputs of various types of instructions, data and the like. The output instruction and the like may be input by any means such as a keyboard, a mouse, a numerical keypad, and a menu screen. The accepting unit 523 can be realized by a device driver of the input means such as a keyboard, menu screen control software, or the like.

The non-communication environment detection unit 524 detects movement to an environment where communication with the server 51 is impossible. Here, detection includes prediction. There are various methods for detecting movement to an environment where communication with the server 51 is impossible. The first method is as described below. The non-communication environment detection unit 524 acquires the radio wave reception level, and detects movement to an environment where communication with the server 51 is impossible if it has detected that a state in which the acquired reception level is less than a predetermined threshold has continued for a period of time that is longer than a predetermined threshold. Also, the meaning of "continue for a period of time that is longer than" is broadly interrupted so as to include a case in which communication cannot be performed for a certain percentage or more of a predetermined period of time (such as a case in which communication of information alternately becomes possible and impossible), a case in which the reception level is less than a threshold for a predetermined percentage or more of a predetermined period of time, and the like. The non-communication environment detection unit 524 may detect movement to an environment where communication with the server 51 is impossible, if the reception level has dropped to less than or equal to a threshold value. That is, the element of time is not essential for this detection.

As a second method, the non-communication environment detection unit 524 may detect movement to an environment where communication with the server 51 is impossible by using the region information storage section 5241, the position information acquiring section 5242 and the non-communication environment detection section 5243 described below.

As a third method, the non-communication environment detection unit 524 may detect movement to an environment where communication with the server 51 is impossible upon receipt of information that indicates movement to an environment where communication with the server 51 is impossible by the close-range wireless communication means. For example, it is assumed that an information sending apparatus that sends, by the close-range wireless communication means, information that indicates movement to an environment where communication with the server 51 is impossible is provided at places just before areas where communication is impossible (non-communication areas), such as a start of a trail up a mountain. In such a case, the non-communication environment detection unit 524 receives, from the information sending apparatus, information that indicates movement to an environment where communication with the server 51 is impossible by the close-range wireless communication means, and detects movement to an environment where communication with the server 51 is impossible. Note that needless to say, the determination method of the non-communication environment detection unit 524 is not limited to the above-described three methods.

The non-communication environment detection unit 524 can be generally realized by a communication module, an MPU, or the like. The processing procedure of the non-communication environment detection unit 524 is generally realized by software, and the software for this is recorded in a recording medium such as a ROM. Note that the processing procedure also may be realized by hardware (dedicated circuitry).

The region information storage section 5241 has stored therein region information that specifies regions where communication is or will be impossible, or regions where communication is possible. The region information generally includes one or more pieces of position information indicating a region. The region information storage section 5241 is preferably a non-volatile recording medium, but it can be realized also by a volatile recording medium. There is no restriction to the process by which the region information is stored in the region information storage section 5241. For example, the region information may be stored in the region information storage section 5241 via a recording medium, or the region information sent via a communication line or the like may be stored in the region information storage section 5241. Alternatively, the region information input via an input device may be stored in the region information storage section 5241.

The position information acquiring section 5242 acquires the position information indicating the position of the terminal apparatus 52. The position information is information of (latitude, longitude), for example. Note that the position information may be information that specifies a position or a region, such as an address. The position information acquiring section 5242 is realized by, for example, a GPS receiver, or a module that specifies the position based on the radio wave reception state from three base stations, or the like. Also, the position information acquiring section 5242 may be realized by a close-range wireless communication means that receives address information.

The non-communication environment detection section 5243 applies the position information to the region information, and detects movement to an environment where communication with the server 51 is impossible. In the case where the region information indicates a region of non-communication environment, the non-communication environment detection section 5243 may detect movement to an environment where communication with the server 51 is impossible by detecting that the position information indicates a position that is within a predetermined threshold from a point that is indicated by the region information and has the shortest distance from the position. In the case where the region information indicates a region of communication environment, the non-communication environment detection section 5243 may determine movement to an environment where communication with the server 51 is impossible by detecting that it is moving toward the region of non-communication environment based on the history of the position information, and also that the terminal apparatus is about to enter the region of non-communication environment (located within a predetermined threshold from the region of non-communication environment). There is no restriction to the determination method of the non-communication environment detection section 5243. The non-communication environment detection section 5243 can be generally realized by an MPU, memory or the like. The processing procedure of the non-communication environment detection section 5243 is generally realized by software, and the software for this is recorded in a recording medium such as a ROM. Note that the processing procedure also may be realized by hardware (dedicated circuitry).

If the non-communication environment detection unit 524 has detected movement to an environment where communication with the server 51 is impossible, the sending instruction sending unit 525 reads out terminal identification information from the terminal identification information storage unit 521, configures a sending instruction including the terminal identification information, and sends the sending instruction to the server 51. The sending instruction is, for example, a command such as "send_info terminal identification information". The sending instruction sending unit 525 is generally realized by a wireless or wired communication means, but may also be realized by a broadcasting means.

The sending instruction configuring section 5251 configures a sending instruction that includes the type information and the terminal identification information. Note that the sending instruction is not required to include the type information. The sending instruction configuring section 5251 can be generally realized by an MPU, memory or the like. The processing procedure of the sending instruction configuring section 5251 is generally realized by software, and the software for this is recorded in a recording medium such as a ROM. Note that the processing procedure also may be realized by hardware (dedicated circuitry).

The sending instruction sending section 5252 sends the sending instruction configured by the sending instruction configuring section 5251 to the server 51. The sending instruction sending section 5252 is generally realized by a wireless or wired communication means, but may also be realized by a broadcasting means.

The output information receiving unit 526 receives output information from the server 51 in response to sending of the sending instruction. The output information receiving unit 526 is generally realized by a wireless or wired communication means, but may be realized by a means for receiving broadcasting.

The output information accumulation unit 527 accumulates the output information received by the output information receiving unit 526 in the output information storage unit 522. The output information accumulation unit 527 can be generally realized by an MPU, memory or the like. The processing procedure of the output information accumulation unit 527 is generally realized by software, and the software for this is recorded in a recording medium such as a ROM. Note that the processing procedure also may be realized by hardware (dedicated circuitry).

The output information output unit 528 outputs the output information accumulated in the output information storage unit 522. Also, the output information output unit 528 outputs the output information received by the output information receiving unit 526. Generally, the output information output unit 528 outputs output information if the accepting unit 523 has accepted the output instruction. However, the output information output unit 528 may automatically output output information in the case where the output information receiving unit 526 has received output information. Here, "output" may be a concept that includes output to a display, projection by a projector, printing with a printer, output of a sound, sending to an outside device, accumulation in a recording medium, and delivery of processing results to other processing apparatuses or programs. The output information output unit 528 may or may not include an output device such as a display or a speaker. The output information output unit 528 can be realized by a driver software of an output device, or a driver software of an output device and an output device, etc.

The communication environment detection unit 529 detects that the terminal apparatus 52 has moved to an environment where communication with the server 51 is possible. There may be cases where communication environment detection unit 529 and the non-communication environment detection unit 524 are physically configured as a single unit. Note that "the terminal apparatus 52 has moved" also includes a case where the prediction has been obtained that it will move to an environment where communication with the server 51 is possible. The communication environment detection unit 529 may be realized by, specifically, a means similar to the non-communication environment detection unit 524. The communication environment detection unit 529 can be generally realized by a communication module, MPU, or the like. The processing procedure of the communication environment detection unit 529 is generally realized by software, and the software for this is recorded in a recording medium such as a ROM. Note that the processing procedure also may be realized by hardware (dedicated circuitry).

In the case where the communication environment detection unit 529 has detected that the terminal apparatus 52 has moved to an environment where communication with the server 51 is possible, the output information deletion unit 530 deletes output information stored in the output information storage unit 522. "In the case where the communication environment detection unit 529 has detected that the terminal apparatus 52 has moved to an environment where communication with the server 51" also includes, for example, a case where communication with the server 51 has been continuously attempted, and if the communication has succeeded, the communication environment detection unit 529 detects that the terminal apparatus 52 has moved to an environment where communication with the server 51 is possible. The output information deletion unit 530 can be generally realized by an MPU, memory or the like. The processing procedure of the output information deletion unit 530 is generally realized by software, and the software for this is recorded in a recording medium such as a ROM. Note that the processing procedure also may be realized by hardware (dedicated circuitry).

Next, an operation performed by the information processing system 5 will be described. First, the operation performed by the server 51 will be described with reference to the flowchart shown in FIG. 31.

(Step S3101) The sending instruction receiving unit 552 determines whether a sending instruction has been received from the terminal apparatus 52. If the sending instruction has been received, the procedure proceeds to step S3102, and if not, the procedure returns to step S3101.

(Step S3102) If the sending instruction has been received in step S3101, the output information acquiring unit 513 acquires, from the sending instruction, the terminal identification information and the type information included in the sending instruction.

(Step S3103) The output information acquiring unit 513 acquires, from the terminal information storage unit 511, output information that is paired with the terminal identification information acquired in step S3102, and that corresponds to the type information acquired in step S3102.

(Step S3104) The output information sending unit 514 sends the output information acquired in step S3103 to the terminal apparatus 52. Then, the processing ends.

Note that in the flowchart shown in FIG. 31, the sending instruction may not include the type information. In this case, in step S3103, the output information acquiring unit 513 acquires, from the terminal information storage unit 511, output information paired with the terminal identification information acquired in step S3102.

Next, an operation performed by the terminal apparatus 52 will be described with reference to the flowchart shown in FIG. 32.

(Step S3201) The non-communication environment detection unit 524 acquires a communication environment. The communication environment is, for example, the radio wave reception level. Also, the communication environment is, for example, position information of the current position. Note that here, there may be cases where the communication environment cannot be acquired. If the communication environment cannot be acquired, generally, it is determined in step S3202 that the terminal apparatus 52 will not move to the non-communication environment.

(Step S3202) The non-communication environment detection unit 524 determines whether the terminal apparatus 52 will move an environment where communication with the server 51 is impossible (non-communication environment) by using the communication environment acquired in step S3201. If it has been determined that the terminal apparatus 52 will move to the non-communication environment, the procedure proceeds to step S3203, and if not, the procedure proceeds to step S3209.

(Step S3203) The sending instruction configuring section 5251 of the sending instruction sending unit 525 reads out terminal identification information from the terminal identification information storage unit 521.

(Step S3204) The sending instruction configuring section 5251 of the sending instruction sending unit 525 configures a sending instruction including the terminal identification information acquired in step S3203 and the type information (automatic sending instruction "1").

(Step S3205) The sending instruction sending section 5252 of the sending instruction sending unit 525 sends the sending instruction configured in step S3204 to the server 51.

(Step S3206) The output information receiving unit 526 determines whether output information has been received from the server 51 in response to sending of the sending instruction. If output information has been received, the procedure proceeds to step S3207, and if not, the procedure returns to step S3206.

(Step S3207) The output information accumulation unit 527 accumulates the output information received in step S3206 in the output information storage unit 522.

(Step S3208) The accepting unit 523 determines whether an output instruction has been accepted. If an output instruction has been accepted, the procedure proceeds to step S3251, and if not, the procedure returns to step S3201.

(Step S3209) The output information deletion unit 530 determines whether output information is stored in the output information storage unit 522. If output information is stored, the procedure proceeds to step S3210, and if not, the procedure returns to step S3208.

(Step S3210) The output information deletion unit 530 deletes the output information stored in the output information storage unit 522. Here, deletion may be physical deletion, processing for setting a deletion flag, processing for moving the output information to a deletion folder, and the like.

(Step S3251) The communication environment detection unit 529 detects whether communication with the server 51 is possible. If communication is possible, the procedure proceeds to step S3252, and if not, the procedure returns to step S3217.

(Step S3252) The sending instruction configuring section 5251 of the sending instruction sending unit 525 reads out terminal identification information from the terminal identification information storage unit 521.

(Step 3213) The sending instruction configuring section 5251 of the sending instruction sending unit 525 configures a sending instruction including the terminal identification information acquired in step S3252 and the type information (manual sending instruction "0").

(Step S3214) The sending instruction sending section 5252 of the sending instruction sending unit 525 sends the sending instruction configured in step S3213 to the server 51.

(Step S3215) The output information receiving unit 526 determines whether output information has been received from the server 51 in response to sending of the sending instruction. If output information has been received, the procedure proceeds to step S3216, and if not, the procedure returns to step S3215.

(Step S3216) The output information output unit 528 outputs the output information received in step S3215, or the output information read out in step S3217. Then, the procedure returns to step S3201.

(Step S3217) The output information output unit 528 reads out output information from the output information storage unit 522.

Note that in the flowchart shown in FIG. 32, the processing ends due to powering off or interruption for aborting the processing.

A specific operation of the information processing system 5 of the present embodiment will be described below. The conceptual diagram of the information processing system 5 is shown in FIG. 29.

First, an output information management table shown in FIG. 33 and a flag management table shown in FIG. 34 are held in the terminal information storage unit 511 of the server 51. The output information management table holds one or more records, each record including "Terminal identification information" and "Output information". "Terminal identification information" is information that identifies the terminal apparatus 52, and here, it is the telephone number of the terminal apparatus 52. Note that the terminal apparatus 52 in this case is, for example, a so-called mobile phone. "Output information" includes attributes of the user (patient) of the terminal apparatus 52, medical record information (medical information), which is information related to diseases, of the user (patient), and the like.

In this case, in the flag management table, information is managed that specifies information that is not extracted in the case where the type information included in the sending instruction is the automatic sending instruction. The flag "1" indicates that the corresponding information will not be extracted if the type information included in the sending instruction indicates an automatic sending instruction. In the flag management table in FIG. 34, all information is specified as information that is not extracted if the type information included in the sending instruction indicates the automatic sending instruction, and thus the attribute "flag" may be omitted. In FIG. 34, the first record indicates that in the case where the attribute "Disease under treatment" has the value "lung cancer" in the output information management table in FIG. 33, that information of "lung cancer" is not acquired (is not sent to the terminal apparatus 52) if the type information included in the sending instruction indicates the automatic sending instruction. Also, the second record indicates that the attribute value of the attribute "treatment history of cancer" is not acquired (is not sent to the terminal apparatus 52) if the type information included in the sending instruction indicates the automatic sending instruction. That is, the flag may be set to the attribute of the output information, to a specific attribute value, or to a specific attribute value selected by the user. Setting a flag to a specific attribute value selected by the user means, for example, in FIG. 33, it is possible that the user "Akiko Tanaka" sets a flag to the attribute value "appendicitis (age 20)", and thereby designates that attribute value as information that is not extracted if the type information included in the sending instruction indicates the automatic sending instruction, and that the user "Hiroko Yamamoto" does not set a flag to the attribute value "appendicitis (age 20)" such that that attribute value is extracted even if the type information included in the sending instruction indicates the automatic sending instruction.

In such a condition, it is assumed that the user "Akiko Tanaka" (hereinafter referred to as the "user A") and the user "Hiroko Yamamoto" (hereinafter referred to as the "user B") went out for mountain climbing while carrying their own terminal apparatuses 52. It is assumed that the user A and the user B went out for mountain climbing from a city area where communication with the server 51 is possible to a place where communication with the server 51 is impossible.

The terminal identification information "090-5234-5678" is stored in the terminal identification information storage unit 521 of the terminal apparatus 52 of the user A.

Also, terminal identification information "090-5222-7753" is stored in the terminal identification information storage unit 521 of the terminal apparatus 52 of the user B.

It is assumed that the user A has become ill in a region where communication with the server 51 is possible, and the user A has visited a hospital near the place where she has become ill to have an examination by a doctor who is not the doctor who usually sees her.

The doctor who is to examine the user A has desired to acquire the attributes, medical information and the like of the user A before examination, and asked the user A to operate her terminal apparatus 52 to acquire medical information and the like of the user A.

It is assumed that then, the user A or the doctor, with the consent of the user A, has operated the terminal apparatus 52 of the user A, and input an output instruction.

Note that the non-communication environment detection unit 524 of the terminal apparatus 52 is assumed to be continuously acquiring a communication environment. The non-communication environment detection unit 524 determines that the terminal apparatus will not move to an environment where communication with the server 51 is impossible (non-communication environment).

Next, the output information deletion unit 530 determines that no output information is stored in the output information storage unit 522.

Then, the accepting unit 523 accepts the output instruction.

Next, the communication environment detection unit 529 detects that communication with the server 51 is possible.

Next, the sending instruction configuring section 5251 of the sending instruction sending unit 525 reads out terminal identification information from the terminal identification information storage unit 521.

Next, the sending instruction configuring section 5251 of the sending instruction sending unit 525 configures a sending instruction (e.g., "send_patient_info, 09012345678, 0") including the acquired terminal identification information "090-5234-5678" and the type information (manual sending instruction "0").

Then, the sending instruction sending section 5252 of the sending instruction sending unit 525 sends the configured sending instruction (e.g., "send_patient_info, 09012345678, 0") to the server 51.

Next, the sending instruction receiving unit 552 of the server 51 receives the sending instruction (e.g., "send_patient_info, 09012345678, 0") from the terminal apparatus 52.

Then, the output information acquiring unit 513 acquires the terminal identification information (09012345678) and the type information (0) included in the sending instruction from the sending instruction.

The output information acquiring unit 513 acquires, from the terminal information storage unit 511, output information that is paired with the terminal identification information (09012345678) and that corresponds to the flag corresponding to the acquired type information (0). Specifically, the output information acquiring unit 513 acquires all output information paired with the terminal identification information (09012345678) from the output information management table in FIG. 33. Then, the output information acquiring unit 513 acquires "Name: Akiko Tanaka, Age: 48, Sex: female, Medical history: appendicitis (age 20), gastric ulcer (age 28), diabetes (age 30 to the present), Treatment history of cancer: no, etc.". Note that the type information (0) is information indicating that a sending instruction has been sent manually with the consent of the user A, and that the user A has agreed to disclose all output information.

Next, the output information sending unit 514 sends the acquired output information to the terminal apparatus 52.

Next, the output information receiving unit 526 of the terminal apparatus 52 receives, from the server 51, the output information "Name: Akiko Tanaka, Age: 48, Sex: female, Medical history: appendicitis (age 20), gastric ulcer (age 28), diabetes (age 30 to the present), Treatment history of cancer: no, etc.", in response to sending of the sending instruction.

Next, the output information output unit 528 outputs the received output information. An example of the output is shown in FIG. 35.

Then, the doctor performs appropriate medical procedure while referencing the information shown in FIG. 35.

Next, it is assumed that the user B has arrived at a start of a trail up a mountain without any problem from a city area where communication with the server 51 is possible. It is assumed that until that time, the non-communication environment detection unit 524 has continuously acquired the communication environment, and has continued to determine that the terminal apparatus 52 will not move to an environment where communication with the server 51 is impossible (non-communication environment). The output information deletion unit 530 has continued to determine that no output information is stored in the output information storage unit 522. It is assumed that until arrival at the start of a trail up a mountain, the accepting unit 523 has continued to determine that no output instruction has been accepted.

Then, it is assumed that while the user B is climbing a mountain after arrival at the start of a trail up a mountain, the non-communication environment detection unit 524 has determined that the terminal apparatus 52 will move to an environment where communication with the server 51 is impossible (non-communication environment). Specifically, for example, the non-communication environment detection unit 524 acquires the radio wave reception level, and has detected that a state in which the acquired reception level is less than a predetermined threshold (e.g., the smallest level of four reception levels (level 1)) has continued for a period of time that is longer than a predetermined threshold (e.g., one minute), and has determined that the terminal apparatus 52 will move to an environment where communication with the server 51 is impossible. Note that it is preferable that the non-communication environment detection unit 524 determines that the terminal apparatus 52 will move to the non-communication environment in the case where the user moves in a direction in which the reception level decreases, and there is no restriction to the algorithm used therefor.

Next, the sending instruction configuring section 5251 of the sending instruction sending unit 525 reads out the terminal identification information "090-5222-7753" from the terminal identification information storage unit 521 of the terminal apparatus 52 of the user B.

Next, the sending instruction configuring section 5251 of the sending instruction sending unit 525 configures a sending instruction (e.g., "send_patient_info, 09012227753, 1") including the acquired terminal identification information "090-5222-7753" and the type information (automatic sending instruction "1").

Next, the sending instruction sending section 5252 of the sending instruction sending unit 525 sends the configured sending instruction (e.g., "send_patient_info, 09012227753, 1") to the server 51.

Next, sending instruction receiving unite 552 of the server 51 receives the sending instruction (e.g., "send_patient_info, 09012227753, 1") from the terminal apparatus 52.

Then, the output information acquiring unit 513 acquires the terminal identification information (09012227753) and the type information (1) included in the sending instruction from the sending instruction.

Next, the output information acquiring unit 513 acquires output information that is paired with the terminal identification information (09012227753), and that corresponds to a flag corresponding to the acquired type information (1). Specifically, the output information acquiring unit 513 acquires output information that is paired with the terminal identification information (09012227753), and that does not include the attribute value "lung cancer" of the attribute "Disease under treatment", and the attribute value of the attribute "Treatment history of cancer", namely, "Name: Hiroko Yamamoto, Age: 28, Sex: female, Medical history: appendicitis (age 25), Disease under treatment: gastric ulcer, etc.". Note that the type information (1) indicates that information highly confidential to the user is not disclosed.

Next, the output information sending unit 514 sends the acquired output information "Name: Hiroko Yamamoto, Age: 28, Sex: female, Medical history: appendicitis (age 25), Disease under treatment: gastric ulcer, etc." to the terminal apparatus 52.

Next, the output information receiving unit 526 of the terminal apparatus 52 receives, in response to sending of the sending instruction, the output information "Name: Hiroko Yamamoto, Age: 28, Sex: female, Medical history: appendicitis (age 25), Disease under treatment: gastric ulcer, etc." from the server 51.

The output information accumulation unit 527 accumulates the received output information "Name: Hiroko Yamamoto, Age: 28, Sex: female, Medical history: appendicitis (age 25), Disease under treatment: gastric ulcer, etc." in the output information storage unit 522.

By the processing described above, even in the case where any trouble has occurred with the user B during mountain climbing, such as falling sick in an environment where communication with the server 51 is impossible, the medical record information and the like of the user B is stored in the terminal apparatus 52 of the user B who is climbing a mountain.

It is assumed that the user B has continued mountain climbing, and has felt sick in the mountain.

Then, a doctor who has happened to be near the user B attempts to provide first aid to the user B. Specifically, the doctor inputs an output instruction to the terminal apparatus 52 of the user B.

Then, the accepting unit 523 of the terminal apparatus 52 of the user B accepts an output instruction.

Next, the communication environment detection unit 529 of the terminal apparatus 52 determines that communication with the server 51 is impossible.

Then, the output information output unit 528 reads out, from the output information storage unit 522, the output information "Name: Hiroko Yamamoto, Age: 28, Sex: female, Medical history: appendicitis (age 25), Disease under treatment: gastric ulcer, etc.".

Next, the output information output unit 528 outputs the read-out output information "Name: Hiroko Yamamoto, Age: 28, Sex: female, Medical history: appendicitis (age 25), Disease under treatment: gastric ulcer, etc.". An output example of the output information is shown in FIG. 36.

It is assumed that the doctor provides first aid while referencing the output information (medical record information) output by the terminal apparatus 52, and the user B feels better and goes down the mountain.

Then, the non-communication environment detection unit 524 of the terminal apparatus 52 acquires a communication environment, and determines that the terminal apparatus 52 has moved to an environment where communication with the server 51 is possible (communication environment).

Next, the output information deletion unit 530 determines that output information is stored in the output information storage unit 522.

Then, the output information deletion unit 530 deletes the output information stored in the output information storage unit 522 of the terminal apparatus 52.

By the processing described above, the fact that communication with the server 51 has become possible is detected, and the output information that may include confidential information can be deleted from the terminal apparatus 52.

As described above, with the present embodiment, information can be acquired in advance even if transition is made to an environment where communication is impossible. As a result, for example, even in the case where a user has suddenly become sick in an environment where communication is impossible, since medical information is stored in the terminal apparatus 52, it is possible to provide appropriate first aid.

Also, with the present embodiment, it is possible to acquire different information in the case where output information is acquired by the user's instruction and in the case where output information is automatically acquired. Therefore, it is possible to appropriately handle confidential information. Specifically, in the case where output information is medical information, if output information is acquired by the intention of the user, all output information is acquired that includes information that is not desired to be known by others (for example, treatment history of cancer, specific names of cancer (such as stomach cancer, lung cancer, pancreas cancer, and the like), etc.), such that more appropriate medical procedure can be performed. In the case where output information is automatically acquired, information that is confidential and thus is not desired to be known by others is excluded from the output information acquired, such that appropriate medical procedure can be performed while securing confidentiality. In this case, even if the terminal apparatus 52 is lost, confidential information will not be acquired by third parties, so that the user does not need to worry.

Furthermore, with the present embodiment, output information can be deleted if transition has been made from an environment where communication with the server 51 is impossible to an environment where communication with the server 51 is possible. Therefore, for example, personal privacy, confidential information, and the like can be protected.

Note that although medical information was used as an example of the output information in the present embodiment, the output information is not limited to medical information, naturally. The output information may be any information such as news information, TV program information (such as a program listing), or the like.

Also, in the specific examples of the present embodiment, output information that is output in an environment where communication with the server 51 is possible is different from output information that is accumulated in the terminal apparatus 52 and then output. However, the same output information may be output.

Furthermore, the processing in the present embodiment may be realized by software. Such software may be distributed by downloading of software product or the like. In addition, such software may be recorded on a recording medium such as a CD-ROM and distributed. Also, needless to say, such software or the recording medium in which the software is recorded may be distributed as a computer program product. Note that this applies to other embodiments of the invention as well. Software that realizes a terminal apparatus of the present embodiment may be a program as described below. That is, this program allows storage in a storage medium of terminal identification information, and causes a computer to function as, a non-communication environment detection unit that detects movement to an environment where communication with the server is impossible, a sending instruction sending unit that sends, in a case where the non-communication environment detection unit has detected movement to an environment where communication with the server is impossible, a sending instruction that includes the terminal identification information to the server, an output information receiving unit that receives output information from the server in response to sending of the sending instruction, an output information storage unit that accumulates the output information received by the output information receiving unit in a storage medium, and an output information output unit that outputs output information accumulated in the storage medium.

Also, with the program, it is preferable that the program causes the computer to function such that the non-communication environment detection unit acquires the radio wave reception level, and in a case where it has been detected that a state in which the acquired reception level is less than a predetermined threshold has continued for a period of time that is longer than a predetermined threshold, the non-communication environment detection unit detects movement to an environment where communication with the server is impossible.

Also, with the program, it is preferable that the program causes the computer to function such that the non-communication environment detection unit includes a region information storage section in which region information that specifies a region where communication is or will be impossible, or a region where communication is possible is stored, a position information acquiring section that acquires position information that indicates a position of the terminal apparatus, and a non-communication environment detection section that applies the position information to the region information, and detects movement to an environment where communication with the server is impossible.

Also, with the program, it is preferable that the program causes the computer to function such that the non-communication environment detection unit receives, by the close-range wireless communication means, information indicating movement to an environment where communication with the server is impossible, and detects movement to an environment where communication with the server is impossible upon receipt of the information.

Also, with the program, it is preferable that the program further causes the computer to function as a communication environment detection unit that detects movement to an environment where communication with the server is possible has been made, and as an output information deletion unit that deletes output information stored in the output information storage unit in a case where the communication environment detection unit has detected that movement to an environment where communication with the server is possible has been made.

Also, with the program, it is preferable that the program further causes the computer to function such that an accepting unit that accepts an input of an output instruction is further included, the sending instruction sending unit includes a sending instruction configuring section that configures a sending instruction that includes the terminal identification information and type information that indicates whether the sending instruction is a sending instruction that is sent in a case where the non-communication environment detection unit has detected movement to an environment where communication with the server is impossible, or a sending instruction that is sent in a case where the accepting unit has accepted an output instruction, and a sending instruction sending section that sends the sending instruction configured by the sending instruction configuring section to the server, one or more pieces of terminal information, in each of which terminal identification information that identifies a terminal apparatus, output information to be sent to the terminal apparatus, a flag that indicates whether the output information is extracted in a case where the sending instruction includes non-communication environment information or in a case where the sending instruction includes output instruction acceptance information are associated with each other, are stored in the storage medium, and the output information acquiring unit acquires, in a case where the sending instruction receiving unit has received a sending instruction, from the storage medium, output information that is paired with the terminal identification information included in the sending instruction and that is paired with the flag corresponding to the type information included in the sending instruction.

Note that in Embodiment 1, the information processing system 1 was described in which position information is acquired and the authentication method is changed according to the position information. Also, in this Embodiment 2, the information processing system 3 was described in which the authentication result is success of authentication only in the case where the positions of two terminal apparatuses satisfy a specific condition. Also in Embodiment 3, the information processing system 4 was described in which information to be output can be changed according to the authentication method. In Embodiment 4, an information processing system was described that detects (predicts) that transition to an environment where communication is impossible is likely to be made or is to be made, and automatically downloads information. Needless to say, systems described in the embodiments may be combined. For example, the information processing system described below can be achieved by combining the systems of Embodiment 1 and Embodiment 3. That is, the information processing system is an information processing system including a terminal apparatus and a server, wherein the terminal apparatus includes: a position information acquiring unit that acquires position information that indicates a current position of the terminal apparatus; an authentication method deciding unit that selects one of two or more authentication methods according to the position information acquired by the position information acquiring unit; an authentication screen output unit that outputs a screen that corresponds to the one authentication method selected by the authentication method deciding unit; an accepting unit that accepts authentication information that is input by a user on the screen output by the authentication screen output unit; an authentication information sending unit that sends, to the server, an authentication method identifier that identifies the authentication method selected by the authentication method deciding unit and the authentication information accepted by the accepting unit; an output information receiving unit that receives, in a case where an execution result of an authentication unit of the server is success of authentication, from the server, one or more pieces of output information corresponding to the authentication method identification information; and an output information output unit that outputs the output information, and the server includes: an information storage unit in which two or more pieces of output information that is information to be output are each stored in association with at least one of two or more different authentication methods; an authentication information receiving unit that receives, from the terminal apparatus, the authentication method identification information and the authentication information; an authentication unit that performs authentication processing by executing, by using the authentication information received by the authentication information receiving unit, one of the two or more different authentication methods that is identified by the authentication method identification information received by the authentication information receiving unit; an information acquiring unit that acquires, in a case where an execution result of the authentication unit is success of authentication, one or more pieces of output information corresponding to the authentication method identification information; and an information sending unit that sends the output information acquired by the information acquiring unit to the terminal apparatus.

Also, the information processing system described below can be achieved by combining the above-described information processing system with the information processing system described in Embodiment 3. That is, in the information processing system, the terminal apparatus further includes: a terminal identification information storage unit in which terminal identification information can be stored; an output information storage unit in which output information can be stored; a non-communication environment detection unit that detects movement to an environment where communication with the server is impossible; and a sending instruction sending unit that sends, in a case where the non-communication environment detection unit has detected movement to an environment where communication with the server is impossible, a sending instruction including the terminal identification information to the server, the output information receiving unit receives output information from the server in response to sending of the sending instruction, the output information output unit accumulates the output information received by the output information receiving unit in the output information storage unit, the information storage unit of the server has stored therein two or more pieces of output information in association with at least one of the two or more different authentication methods, and has stored therein terminal identification information that identifies the terminal apparatus and output information associated with each other, the server further includes a sending instruction receiving unit that receives, from a terminal apparatus, a sending instruction that includes terminal identification information that identifies that terminal apparatus and that is an instruction to send output information, and in a case where the sending instruction receiving unit has received a sending instruction, the information acquiring unit acquires, from the information storage unit, output information that is paired with the terminal identification information included in that sending instruction. The block diagram of this information processing system is shown in FIG. 37. That is, the information processing system includes a terminal apparatus 371 and a server 372. The terminal apparatus 371 includes the accepting unit 111, the position information acquiring unit 112, the authentication method deciding unit 113, the authentication screen output unit 114, the authentication information sending unit 115, the authentication result accepting unit 116, the authentication result output unit 117, the processing unit 118, an output information receiving unit 1714, an output information output unit 1715, the information storage unit 1731, the information acquiring unit 1736, and the information sending unit 1738. Also, the server 372 includes the authentication information receiving unit 132, the authentication unit 133, the authentication result sending unit 134, the terminal identification information storage unit 521, the non-communication environment detection unit 524, and the sending instruction sending unit 525.

FIG. 38 shows the external appearance of a computer that executes the programs referred to in the specification to realize the terminal apparatus, the server, the second terminal, the first terminal apparatus, the second terminal apparatus, and the like in the foregoing embodiments. The foregoing embodiments may be realized using computer hardware and a computer program executed thereon. FIG. 38 is a schematic diagram of a computer system 340. FIG. 39 is a diagram illustrating an internal configuration of the computer system 340.

In FIG. 38, the computer system 340 includes a computer 341 including an FD drive 3411 and a CD-ROM drive 3412, a keyboard 342, a mouse 343, and a monitor 344.

In FIG. 39, the computer 341 includes not only the FD drive 3411 and the CD-ROM drive 3412, but also an MPU 3413, a bus 3414 that is connected to the CD-ROM drive 3412 and the FD drive 3411, a ROM 3415 in which a program such as a startup program is to be stored, a RAM 3416 that is connected to a CPU 3413 and in which a command of an application program is temporarily stored and by which a temporary storage area is provided, and a hard disk 3417 in which an application program, a system program, and data are to be stored. Although not shown, the computer 341 may further include a network card that provides connection to a LAN.

The program for causing the computer system 340 to execute the functions of the terminal apparatus, the server and the like in the foregoing embodiments may be stored in a CD-ROM 3501 or an FD 3502, which are inserted into the CD-ROM drive 3412 or the FD drive 3411, and may be transmitted to the hard disk 3417. Alternatively, the program may be transmitted to the computer 341 via a network (not shown) and stored in the hard disk 3417. At the time of execution, the program is loaded into the RAM 3416. The program may be loaded from the CD-ROM 3501 or the FD 3502, or directly from the network.

The program does not necessarily have to include, for example, an operating system (OS), a third party program, or the like to cause the computer 341 to execute the functions of the terminal apparatus, the server, and the like in the above-described embodiments. The program may only include a portion of commands capable of calling an appropriate function (module) in a controlled mode and obtaining the desired results. The manner in which the computer system 340 operates is well known, and, thus, a detailed description thereof is omitted.

It should be noted that, in the program, a process performed by hardware, for example, a process performed by a modem or an interface card in the step of sending (a process that can be performed only by such hardware) is not included in the step of sending information, the step of receiving information, and the like.

Furthermore, the computer that executes this program may be a single computer, or may be multiple computers. More specifically, centralized processing may be performed, or distributed processing may be performed.

Furthermore, in the foregoing embodiments, needless to say, two or more communication means provided in a single apparatus may be realized by a physically single medium.

Furthermore, in the foregoing embodiments, each process (each function) may be realized as an integrated process using a single apparatus (system), or may be realized as a distributed process using multiple apparatuses.

The present invention is not limited to the embodiments set forth herein, and various modifications are possible. Needless to say, such modifications are also embraced in the scope of the present invention.

INDUSTRIAL APPLICABILITY

As described above, the information processing system of the present invention has an effect of appropriately providing necessary information while appropriately securing the privacy of the user, and is useful as a medical information management system or the like.

BRIEF DESCRIPTION OF THE DRAWINGS

FIG. 5 is a diagram illustrating a region authentication information management table in Embodiment 1.

FIG. 6 is a diagram illustrating a medical record information management table in Embodiment 1.

FIG. 12 is a diagram illustrating another region authentication information management table in Embodiment 1.

FIG. 21 is a diagram illustrating a medical record information management table in Embodiment 3.

FIG. 22 is a diagram illustrating a search condition management table in Embodiment 3.

FIG. 23 is a diagram illustrating a registration information management table in Embodiment 3.

FIG. 33 is a diagram illustrating an output information management table in Embodiment 4.

FIG. 34 is a diagram illustrating a flag management table in Embodiment 4.

Figure 1:
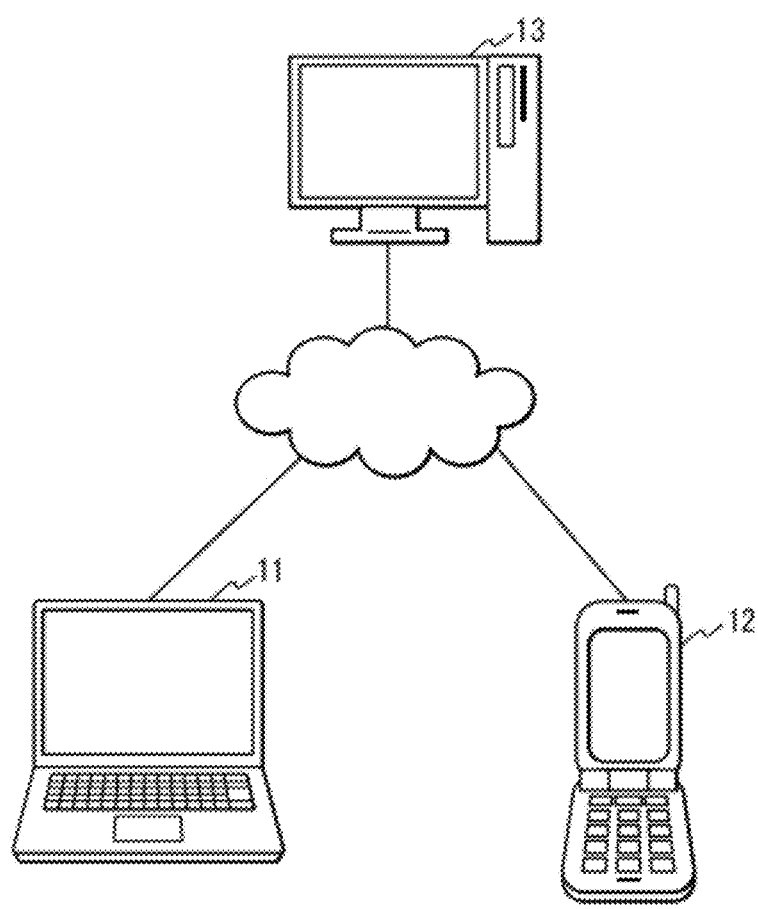
FIG. 1 is a conceptual diagram of an information processing system in Embodiment 1.
Figure 2:
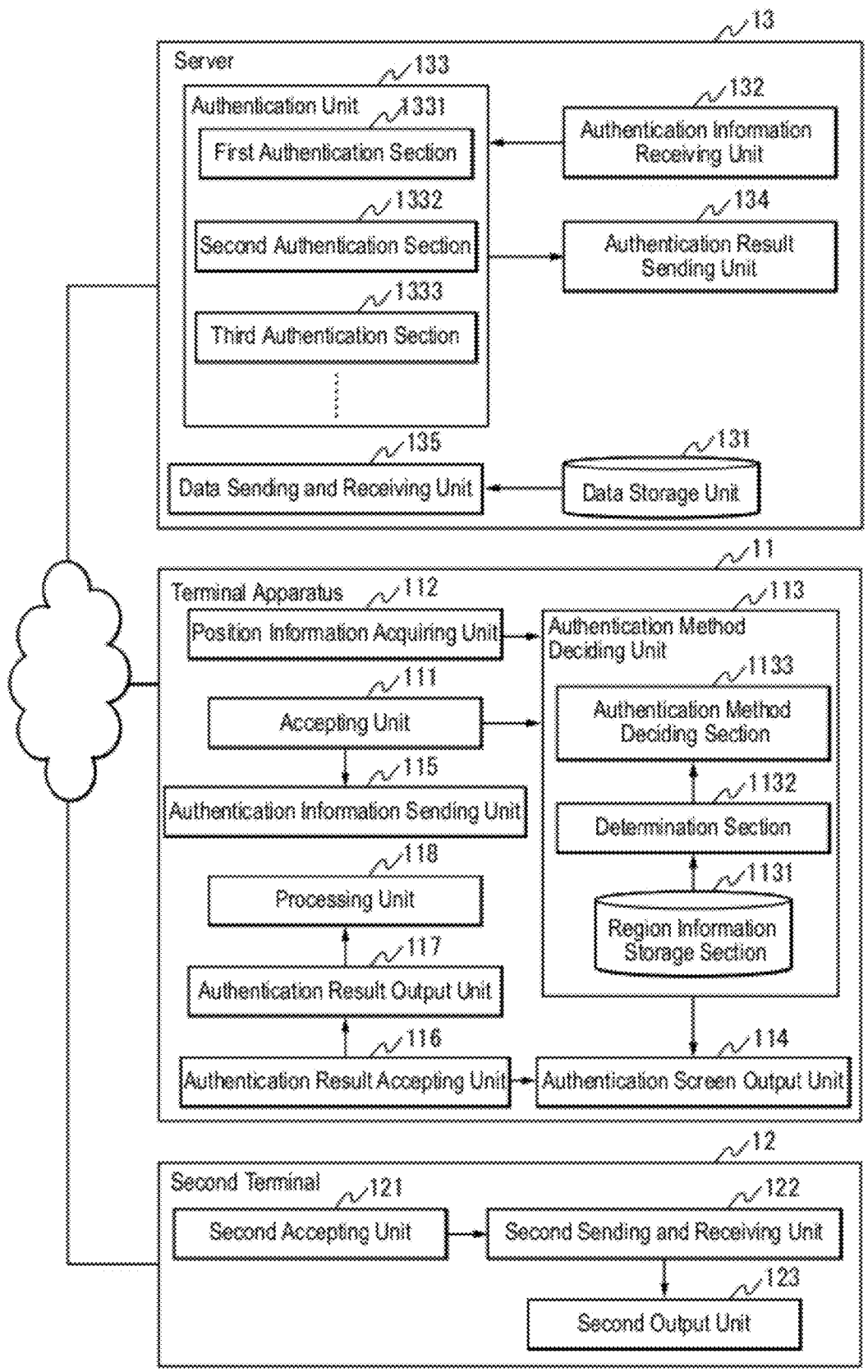
FIG. 2 is a block diagram of the information processing system in Embodiment 1.
Figure 3:
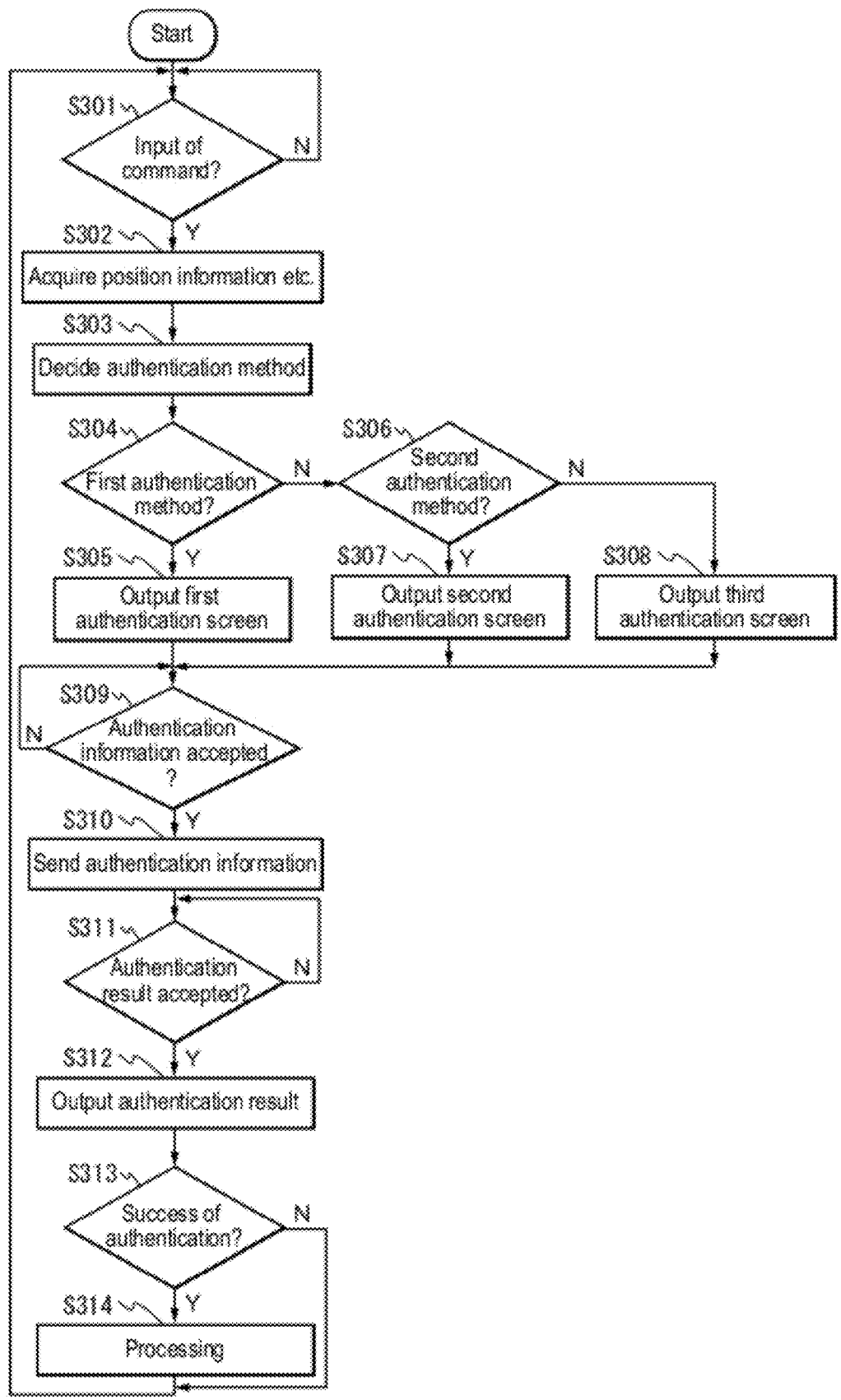
FIG. 3 is a flowchart illustrating an operation of a terminal apparatus in Embodiment 1.
Figure 4:
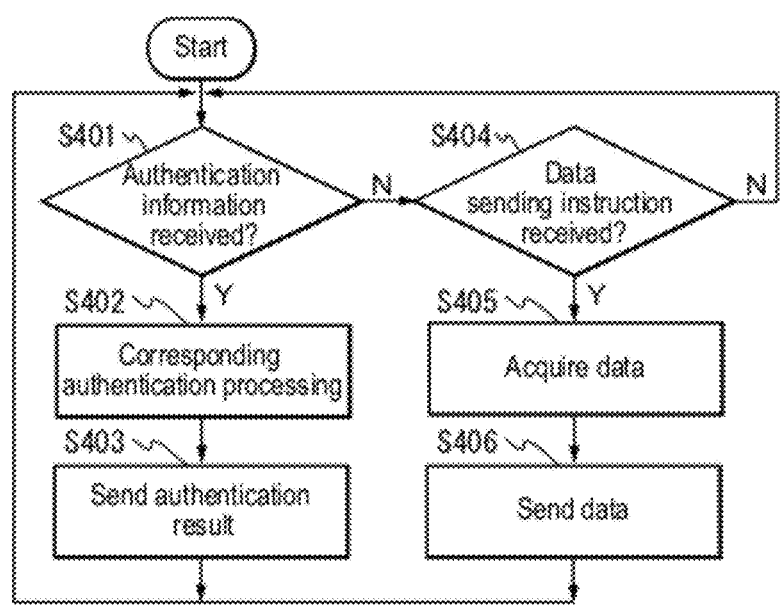
FIG. 4 is a flowchart illustrating an operation of a server in Embodiment 1.
Figure 7:
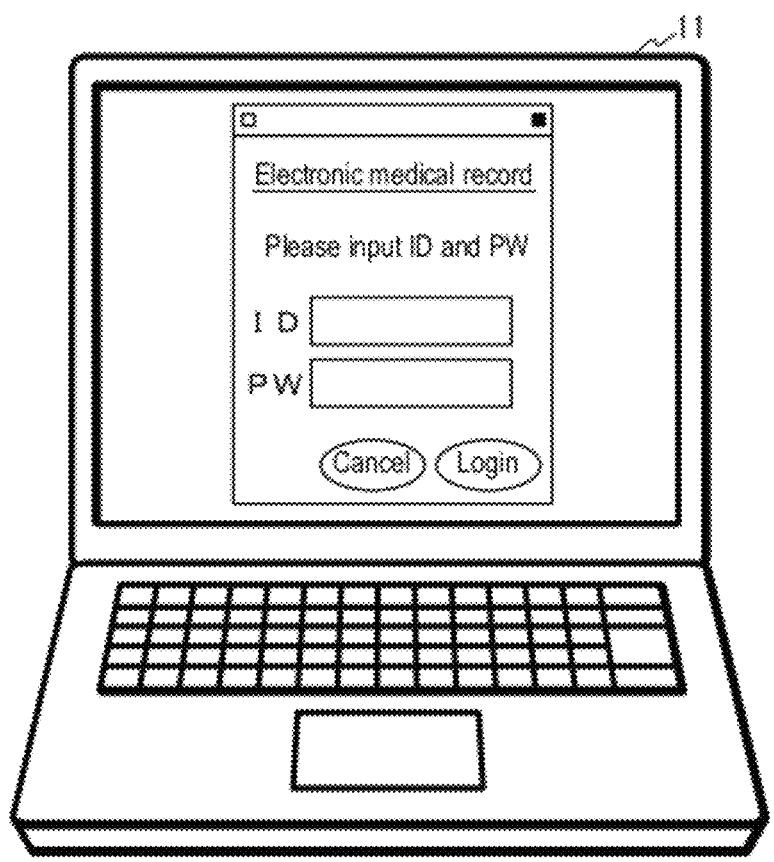
FIG. 7 shows an example of an authentication screen in Embodiment 1.
Figure 8:
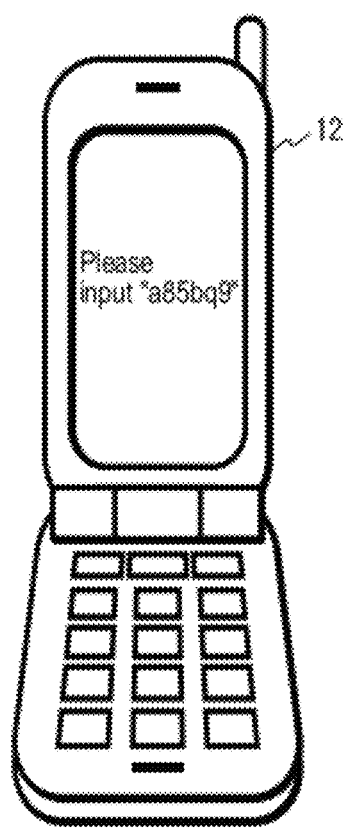
FIG. 8 shows an example of second authentication information output to a second terminal 52 in Embodiment 1.
Figure 9:
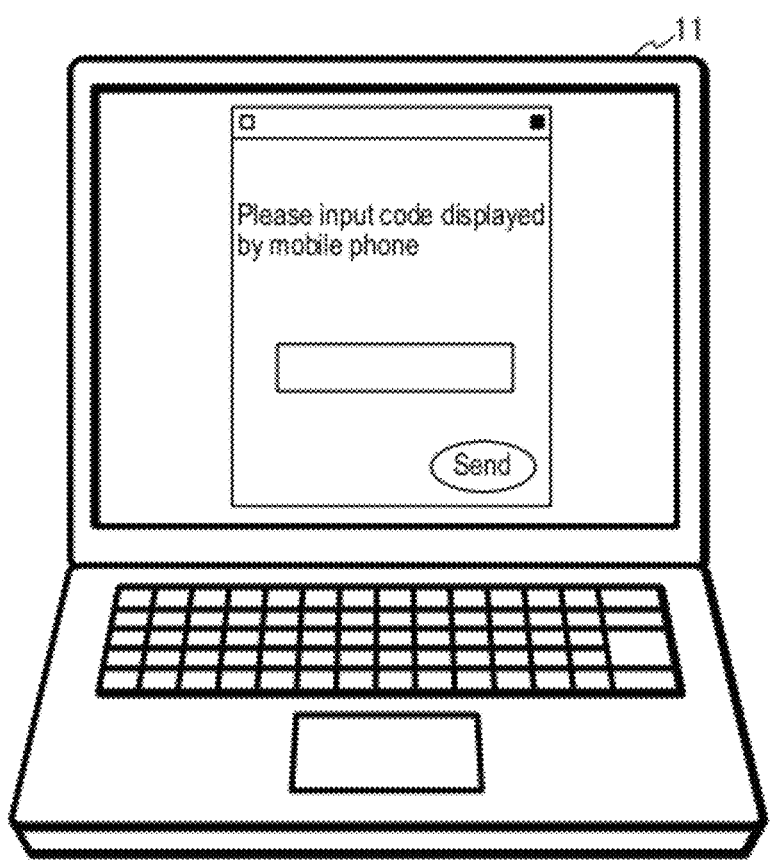
FIG. 9 shows an example of a second authentication screen in Embodiment 1.
Figure 10:
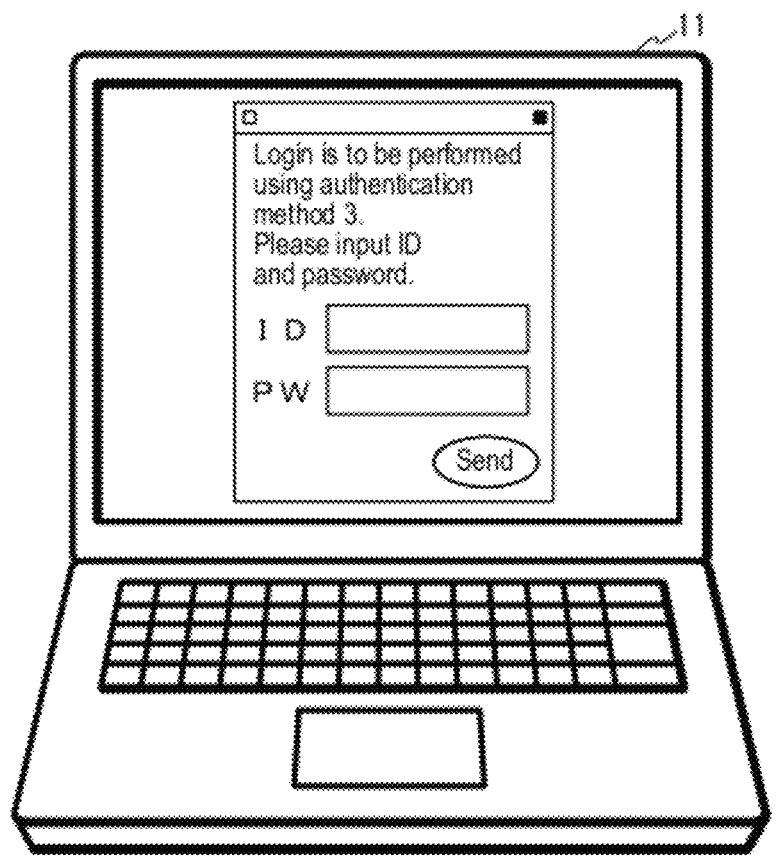
FIG. 10 is an example of an authentication screen in Embodiment 1.
Figure 11:
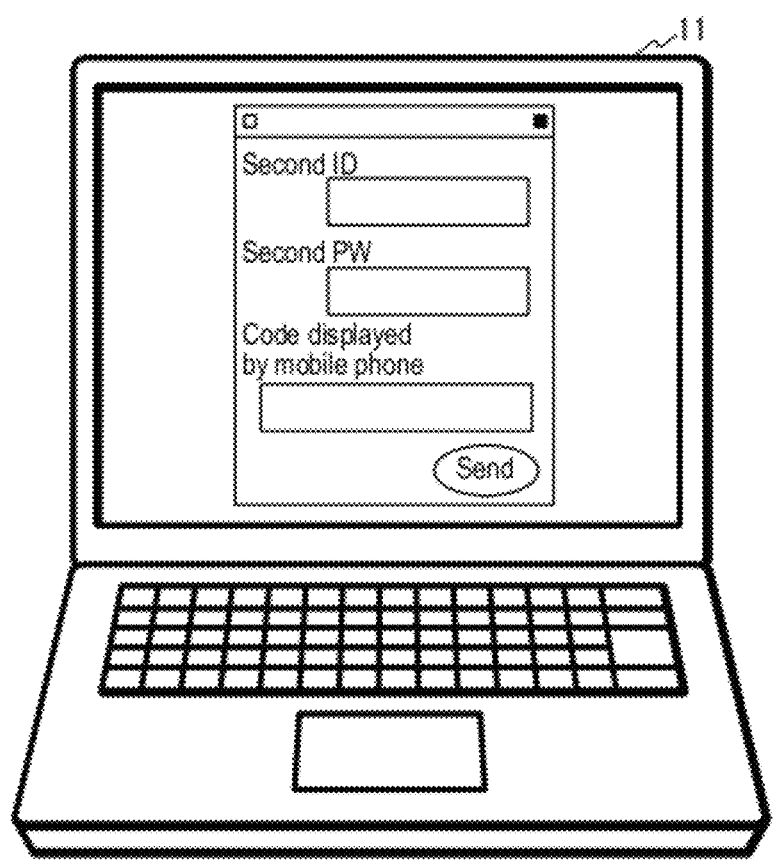
FIG. 11 is another example of the second authentication screen in Embodiment 1.
Figure 13:
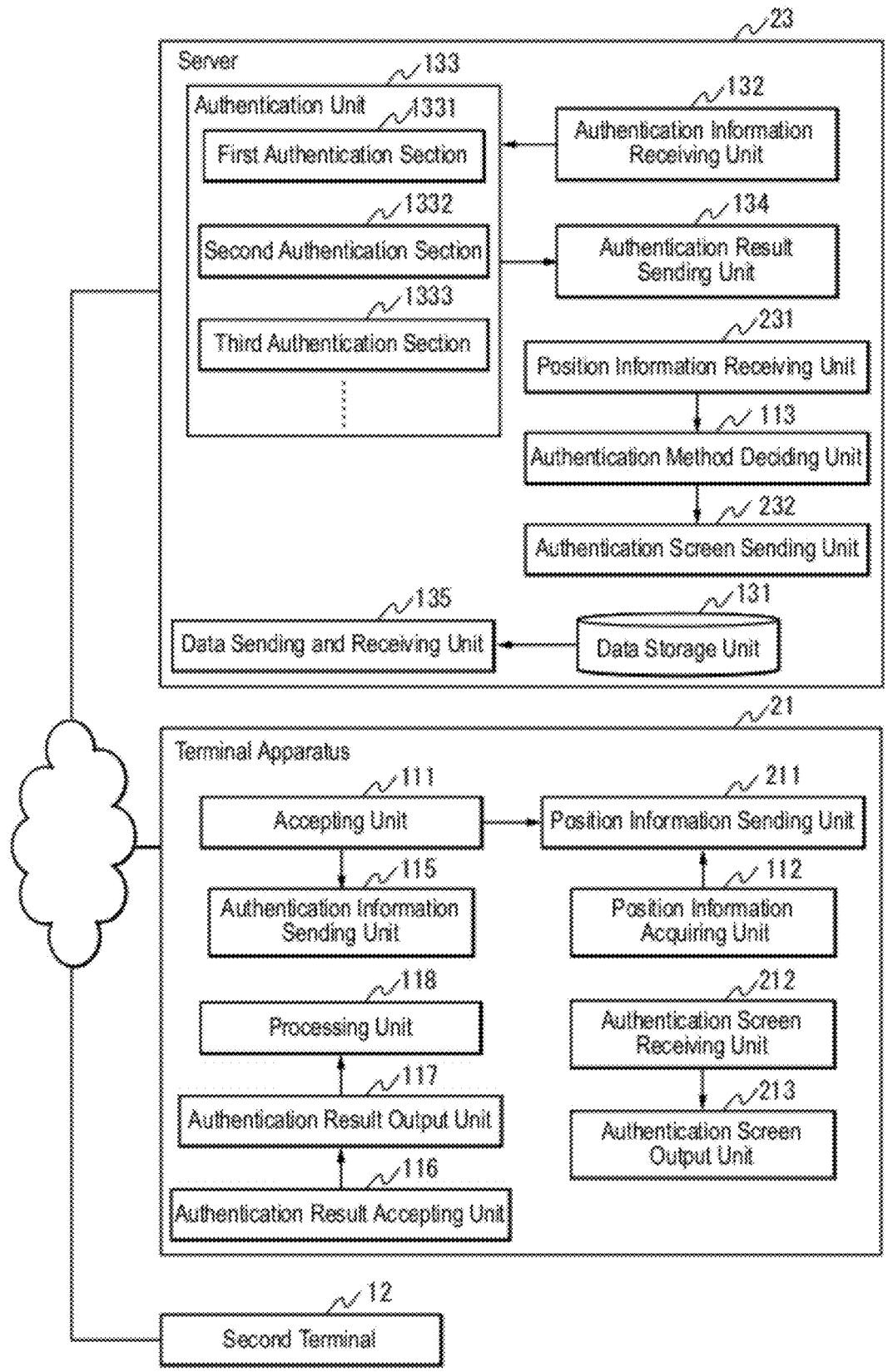
FIG. 13 is another block diagram of the information processing system in Embodiment 1.
Figure 14:
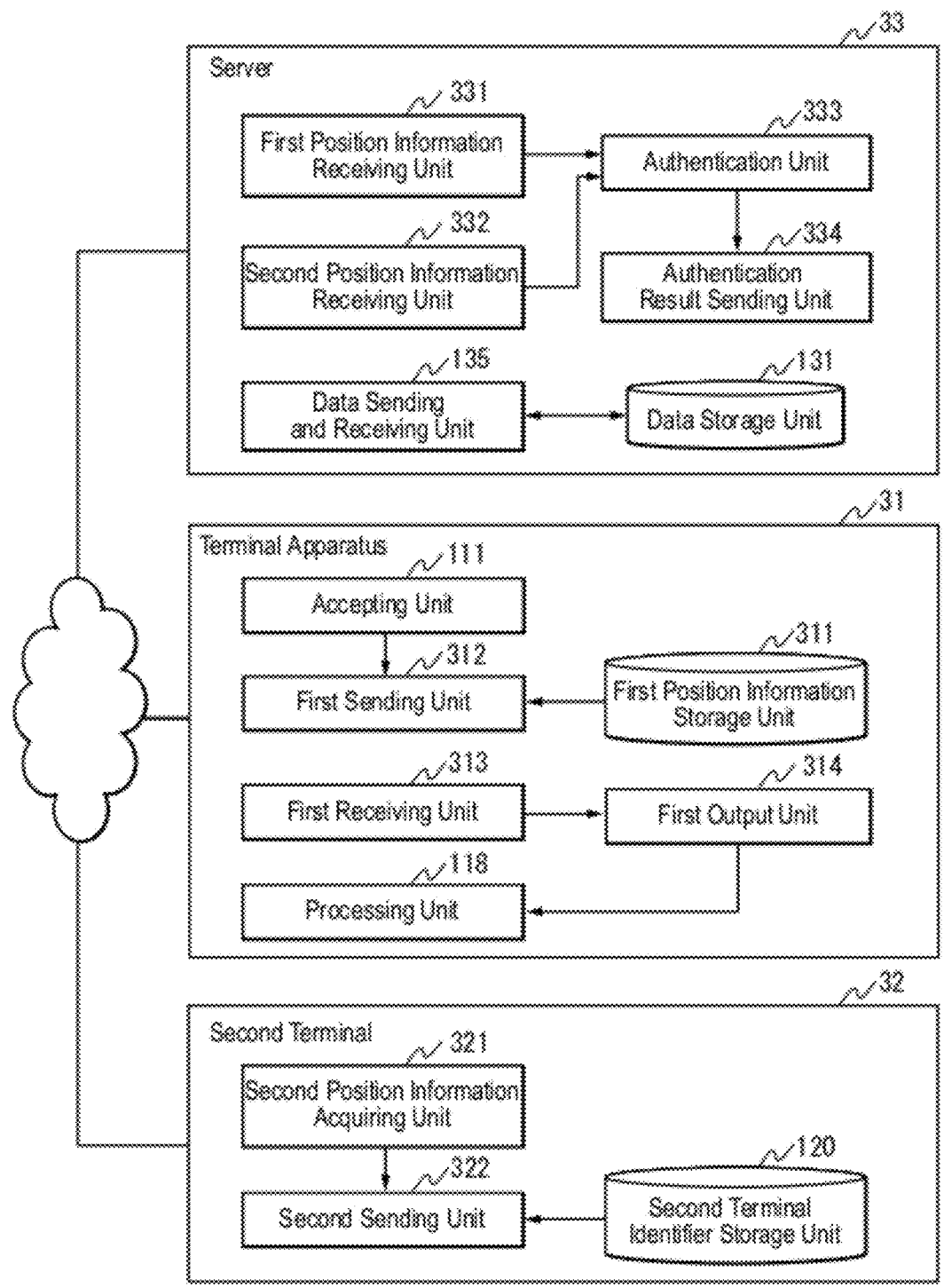
FIG. 14 is a block diagram of an information processing system in Embodiment 2.
Figure 15:
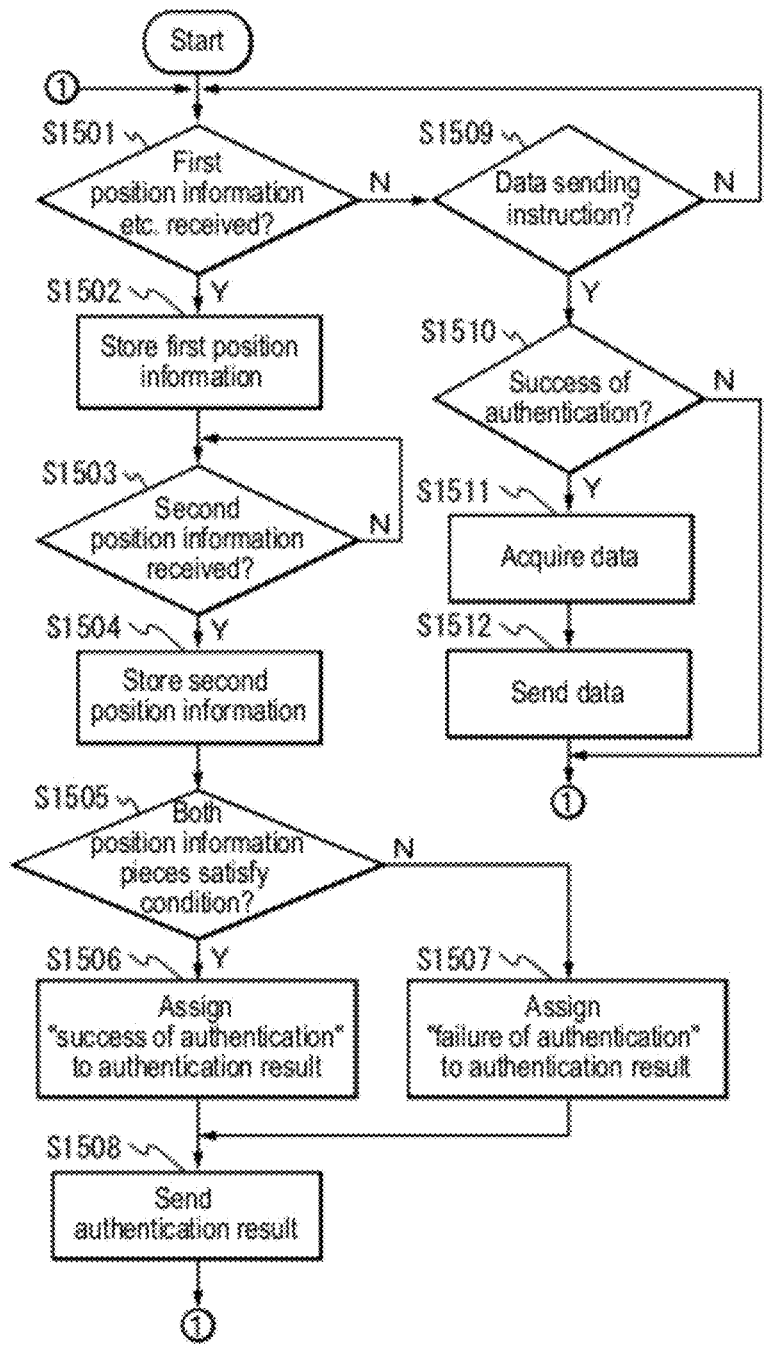
FIG. 15 is a flowchart illustrating an operation of a server in Embodiment 2.
Figure 16:
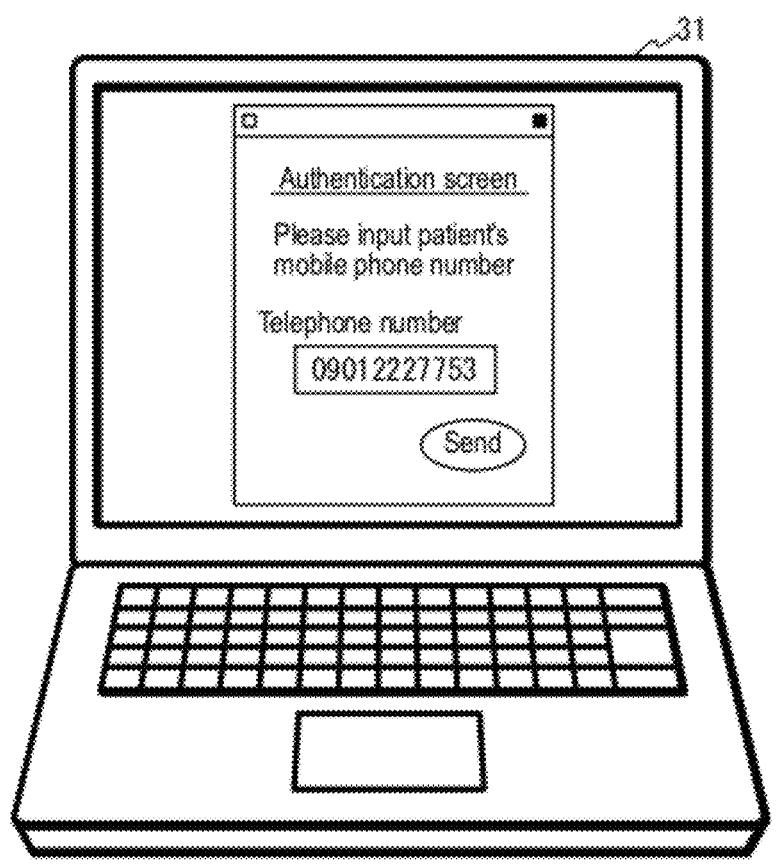
FIG. 16 shows an example of a second authentication screen in Embodiment 2.
Figure 17:
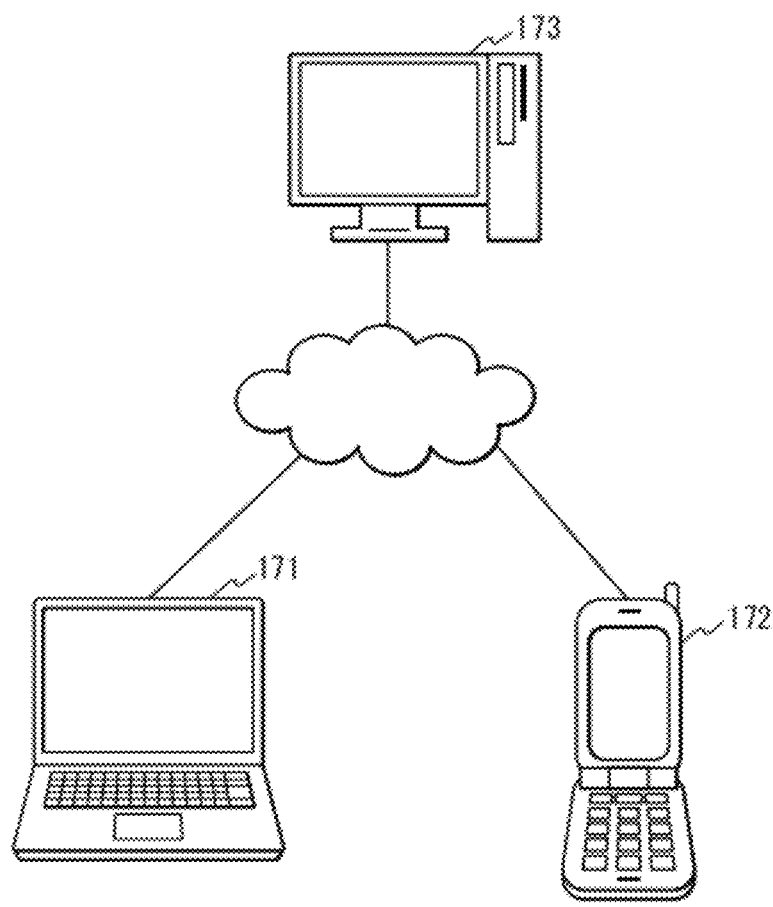
FIG. 17 is a conceptual diagram of an information processing system in Embodiment 3.
Figure 18:
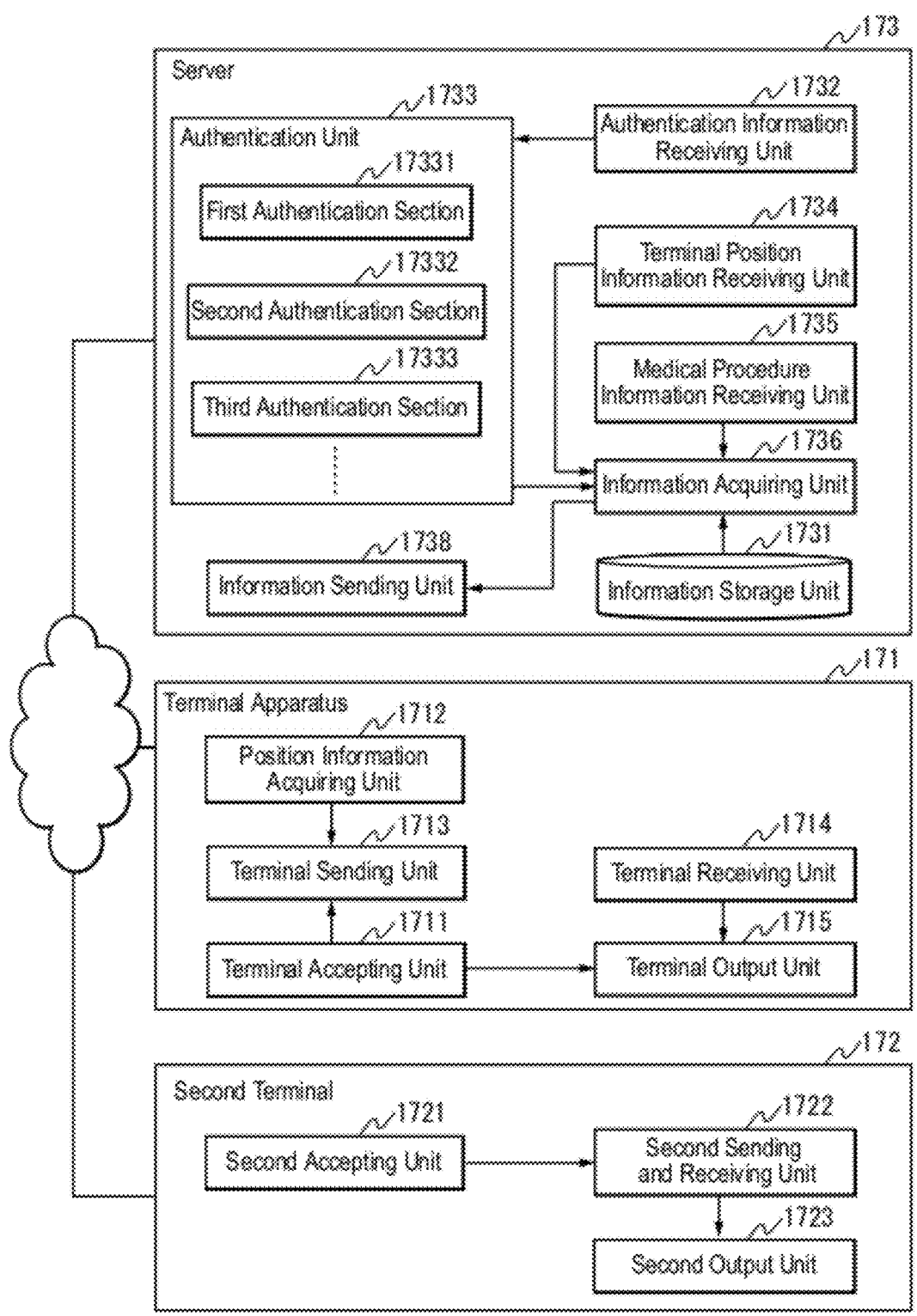
FIG. 18 is a block diagram of the information processing system in Embodiment 3.
Figure 19:
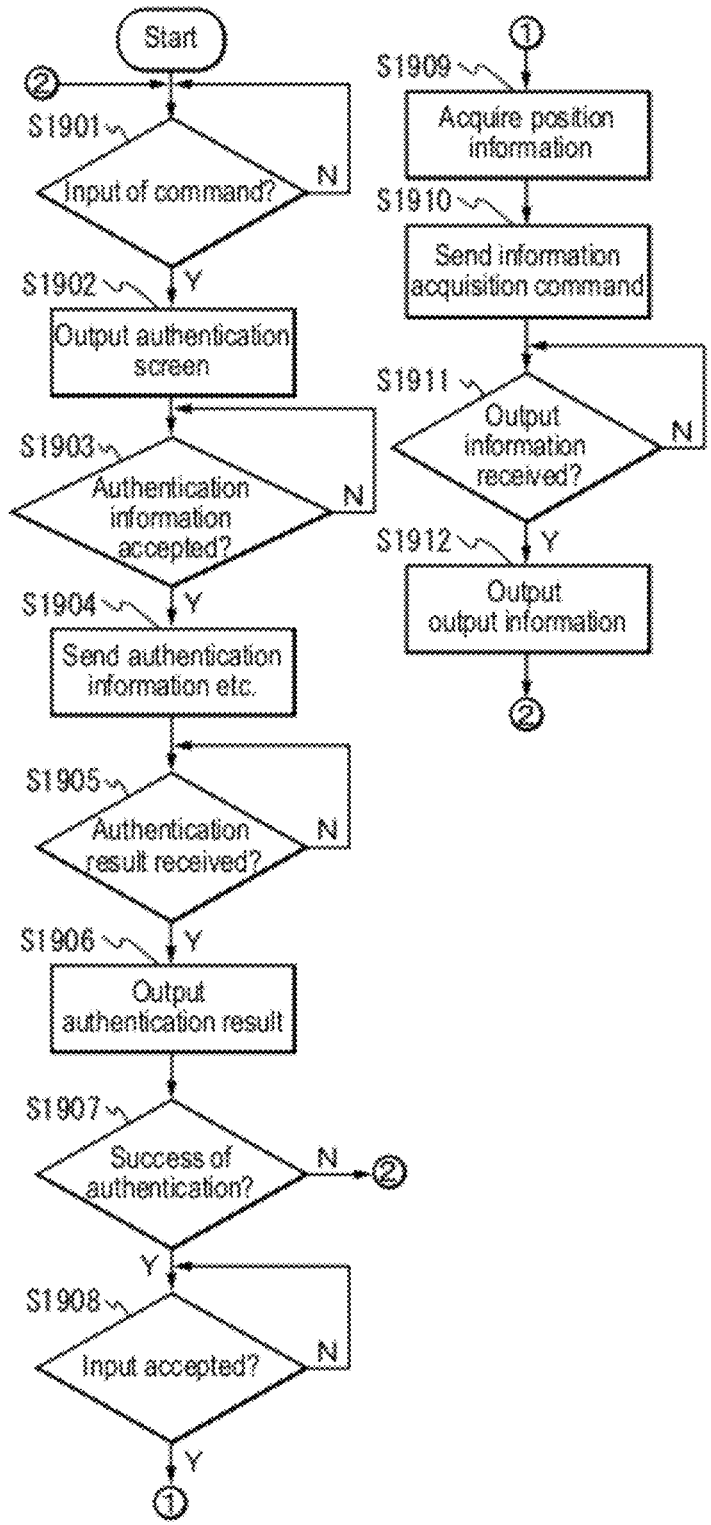
FIG. 19 is a flowchart illustrating an operation of a terminal apparatus in Embodiment 3.
Figure 20:
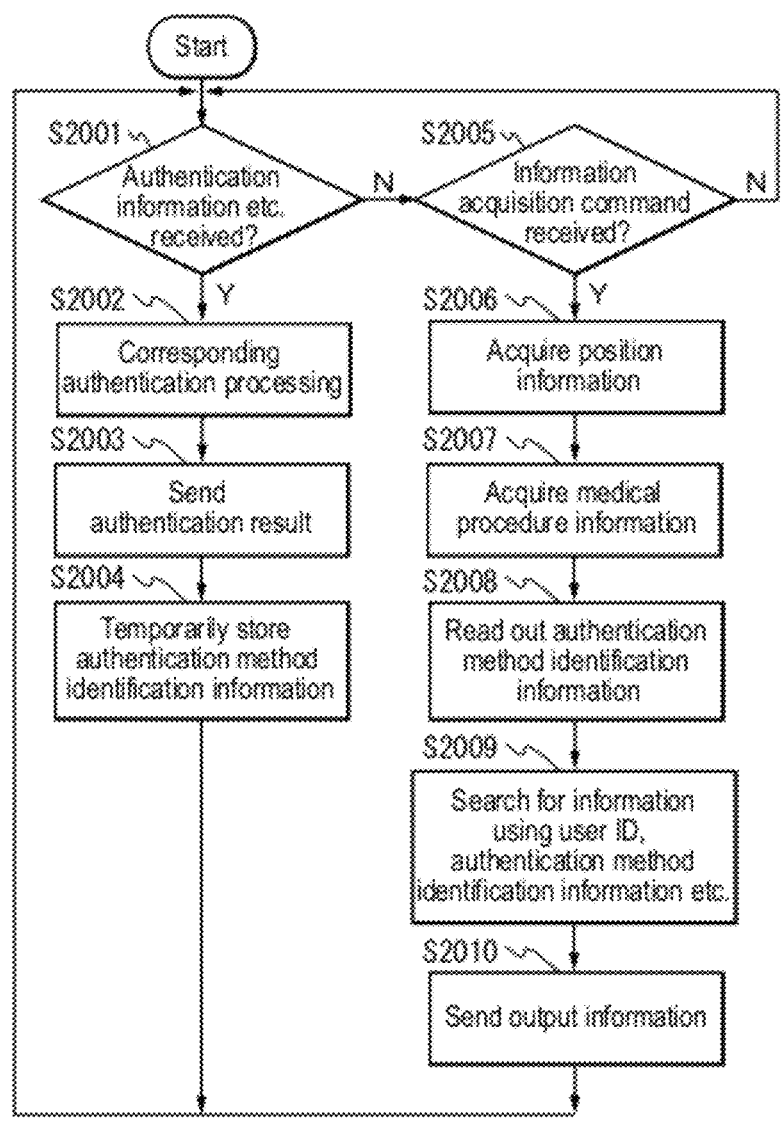
FIG. 20 is a flowchart illustrating an operation of a server in Embodiment 3.
Figure 24:
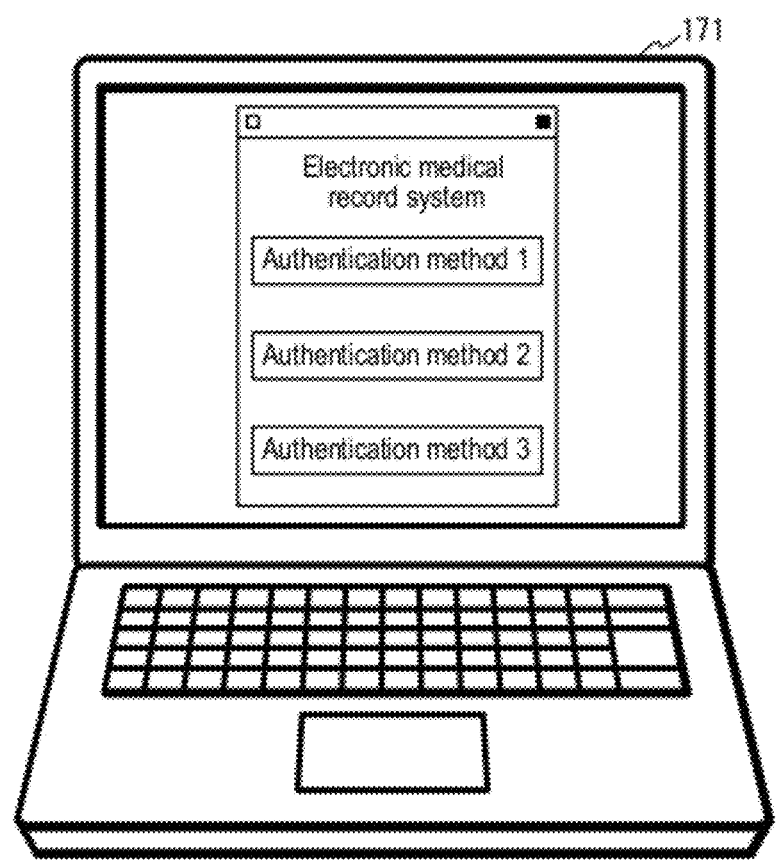
FIG. 24 shows an example of a screen of a terminal apparatus 51 in Embodiment 3.
Figure 25:
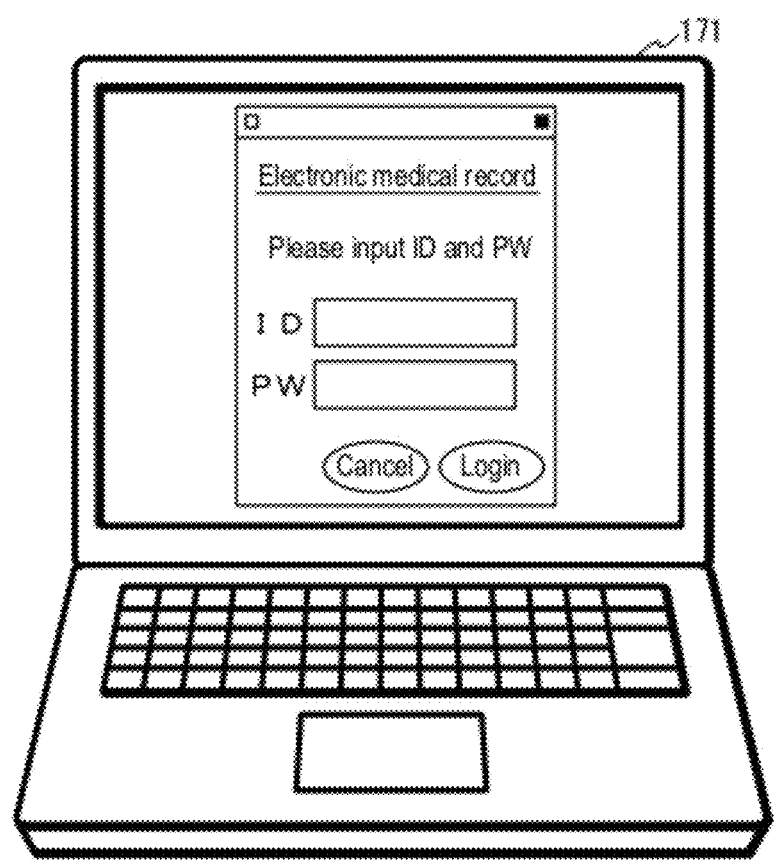
FIG. 25 shows an example of an authentication screen in Embodiment 3.
Figure 26:
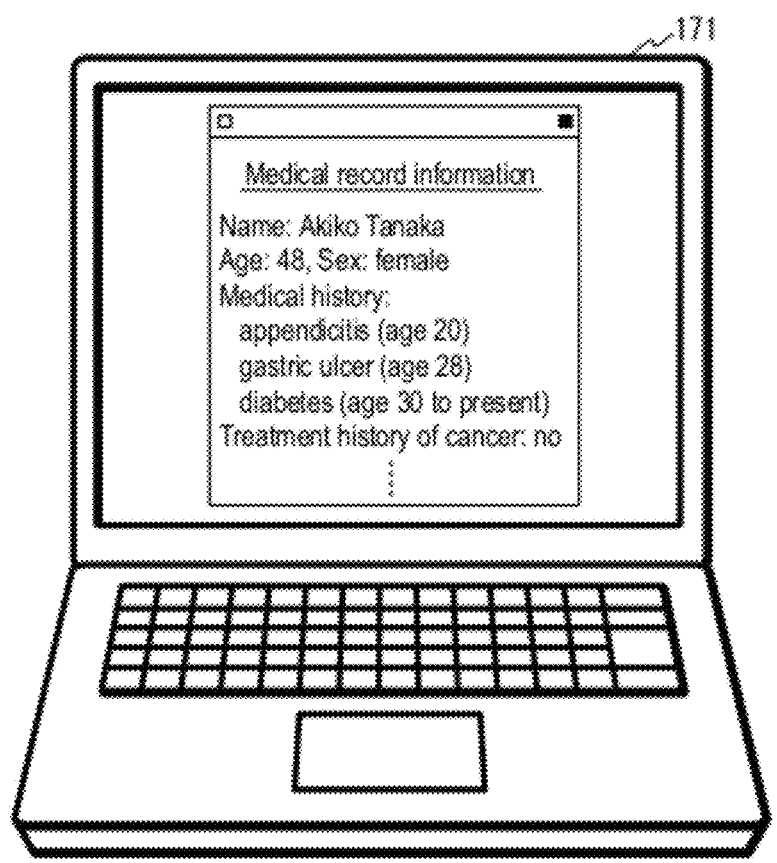
FIG. 26 shows an output example of output information in Embodiment 3.
Figure 27:
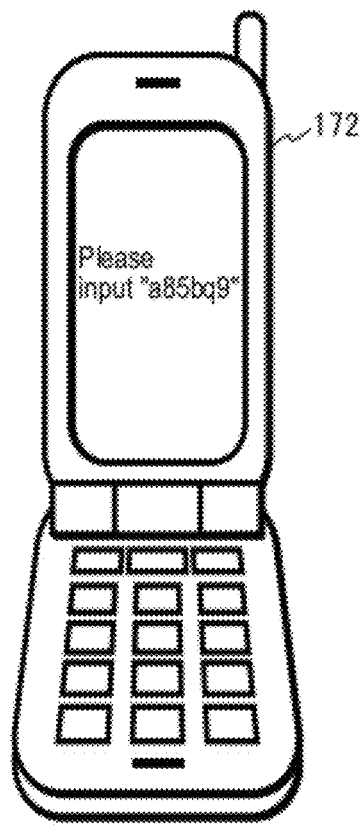
FIG. 27 shows another output example of output information in Embodiment 3.
Figure 28:
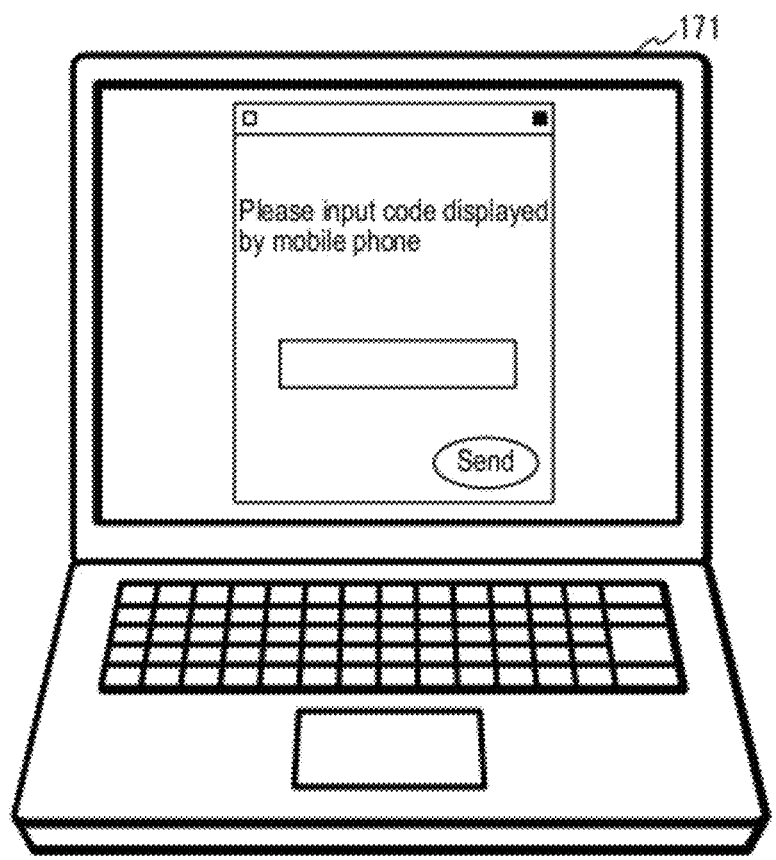
FIG. 28 is a diagram illustrating a second authentication screen in Embodiment 3.
Figure 29:
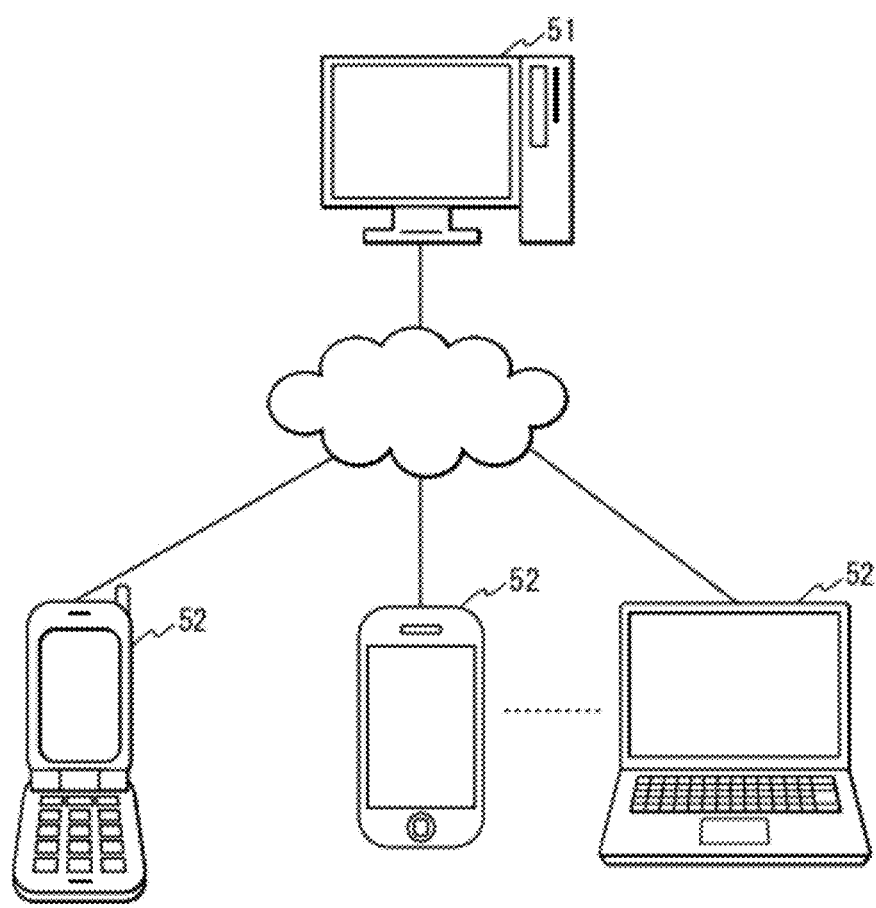
FIG. 29 is a conceptual diagram of an information processing system in Embodiment 4.
Figure 30:
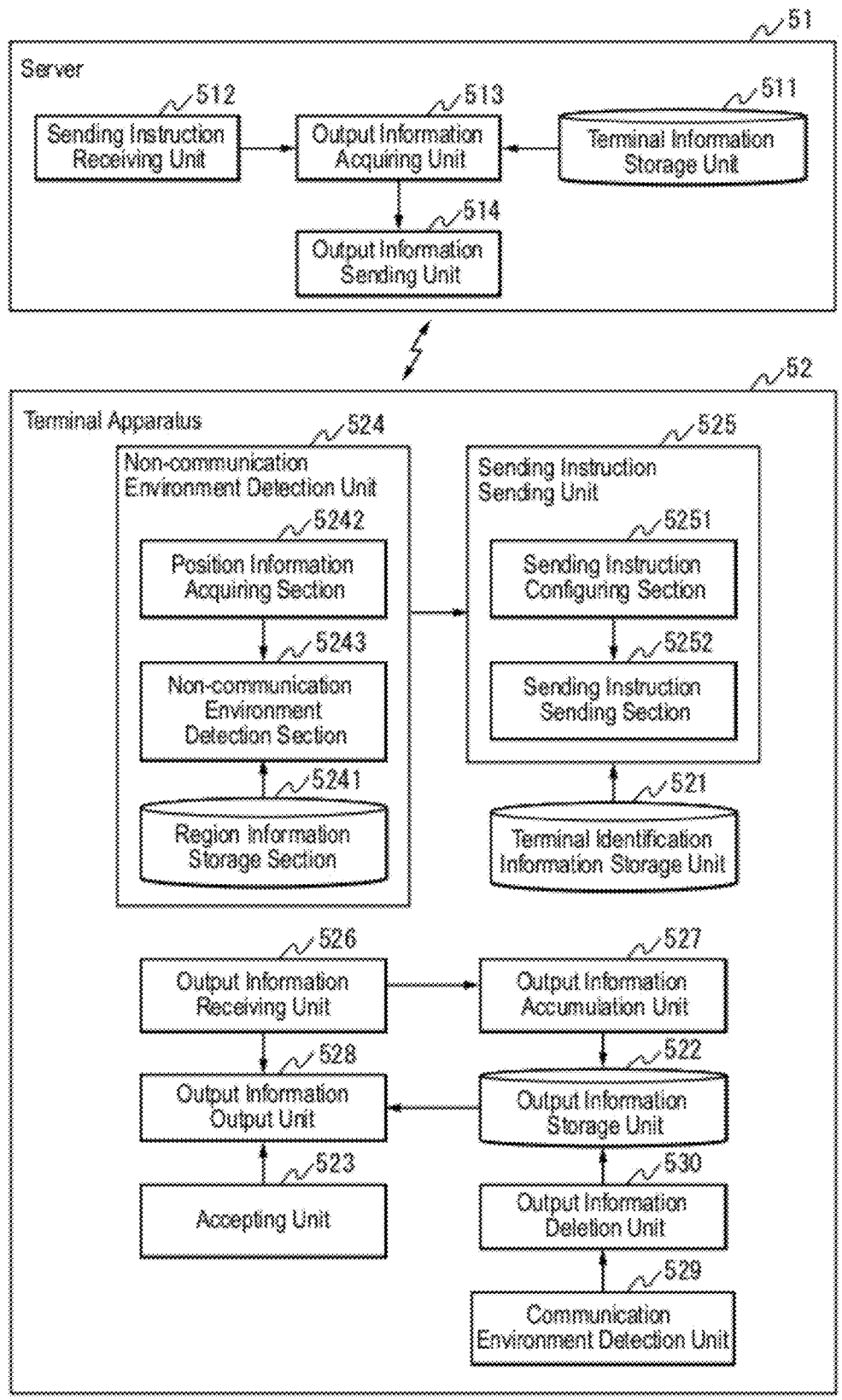
FIG. 30 is a block diagram of an information processing system in Embodiment 4.
Figure 31:
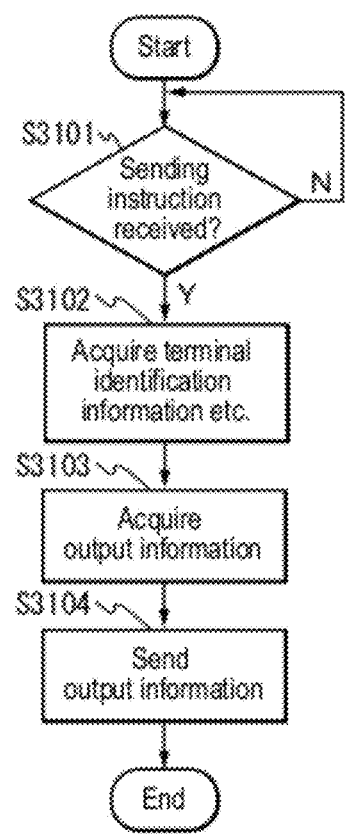
FIG. 31 is a flowchart illustrating an operation of a server in Embodiment 4.
Figure 32:
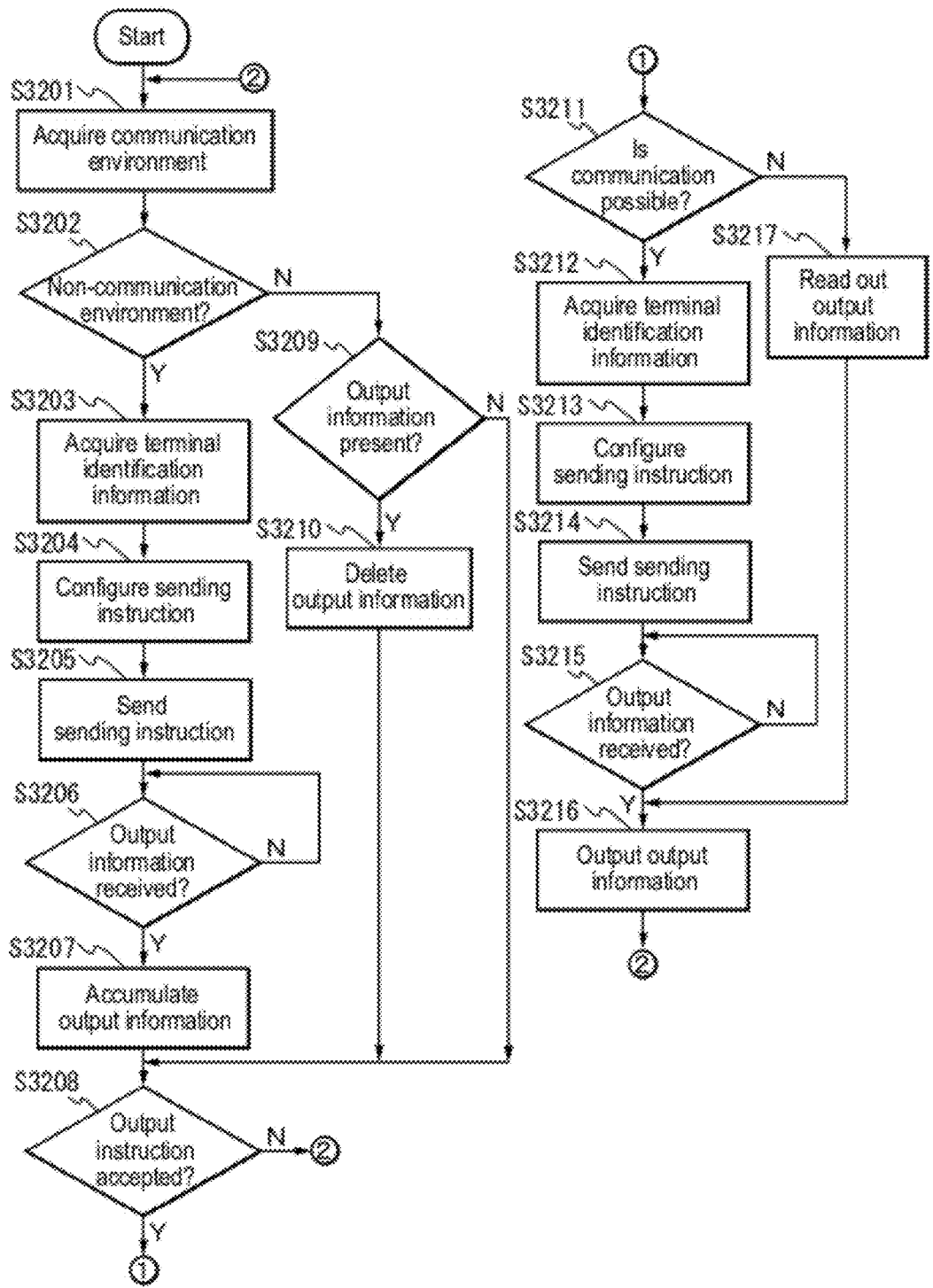
FIG. 32 is a flowchart illustrating an operation of a terminal apparatus in Embodiment 4.
Figure 35:
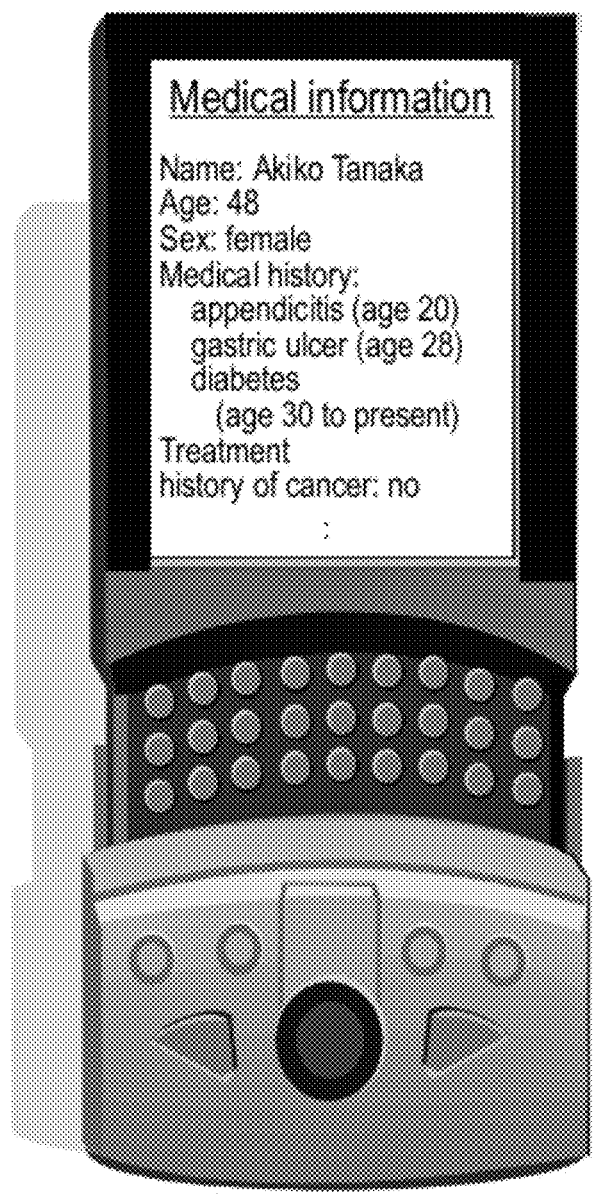
FIG. 35 shows an output example of output information in Embodiment 4.
Figure 36:
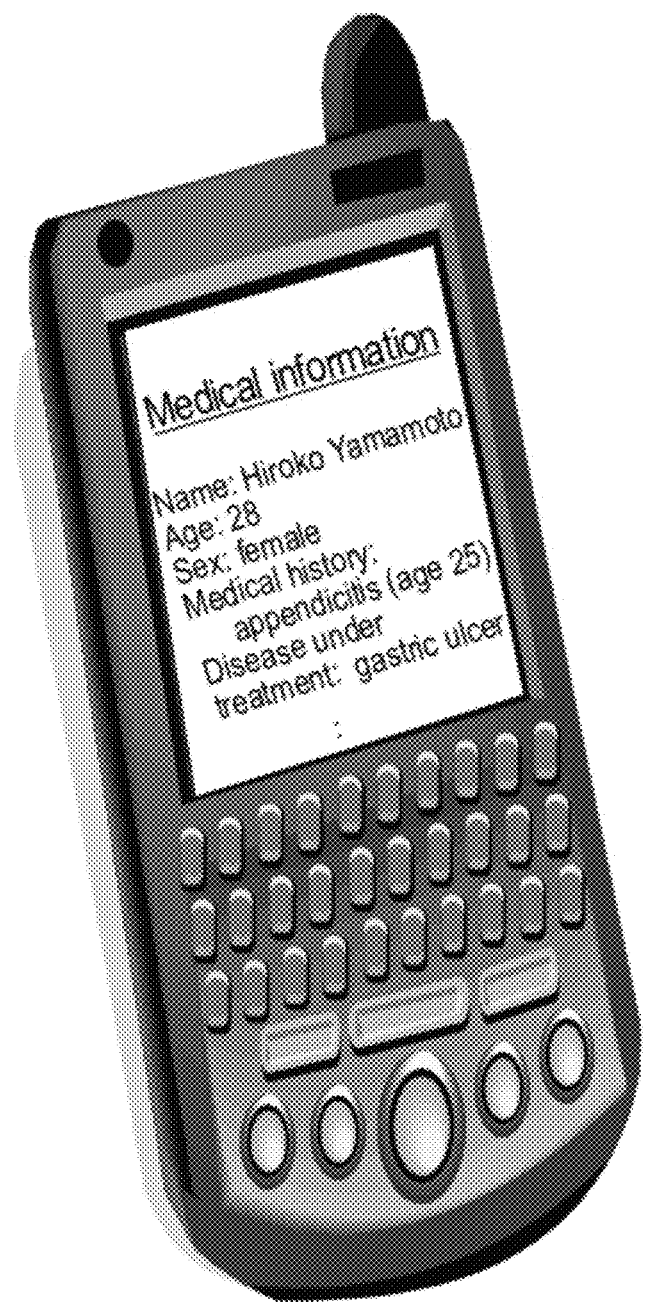
FIG. 36 shows another output example of output information in Embodiment 4.
Figure 37:
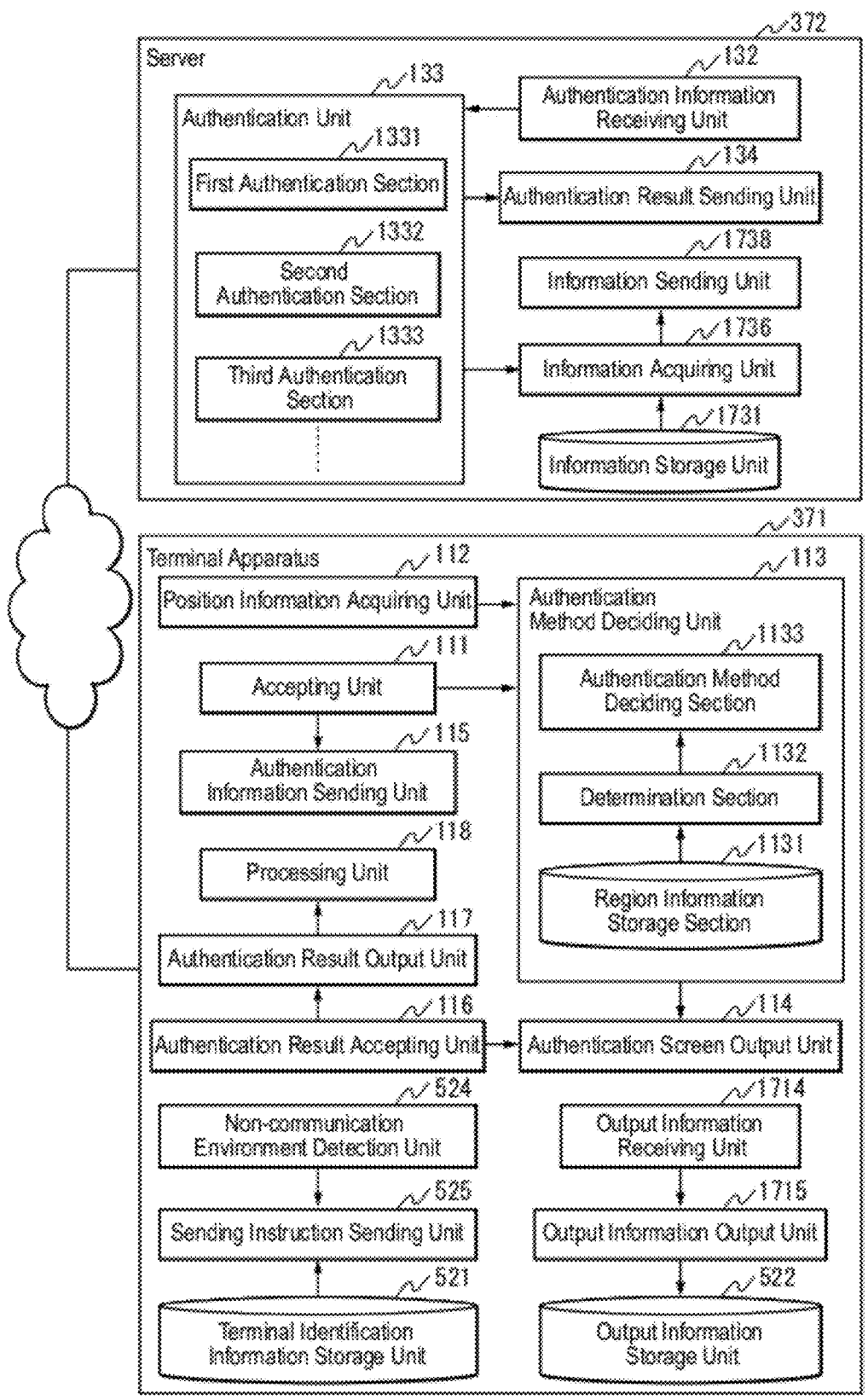
FIG. 37 is a block diagram of an information processing system of the foregoing embodiments.
Figure 38:
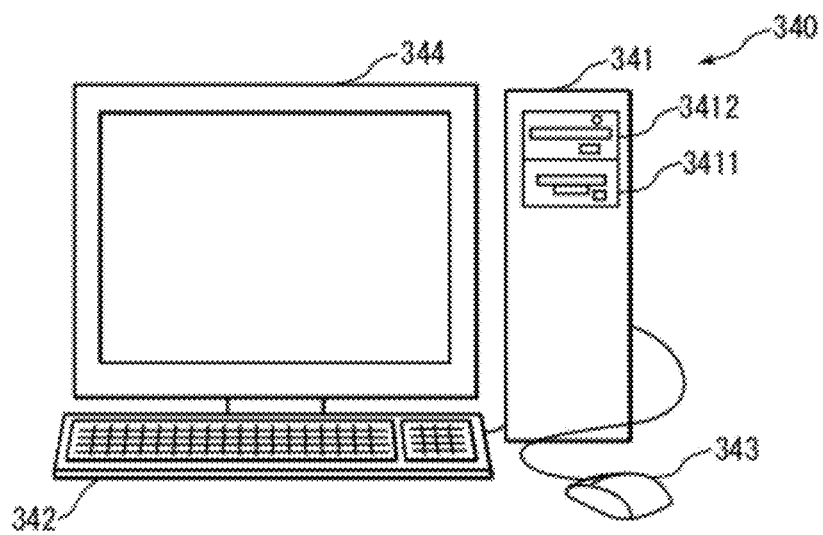
FIG. 38 is a schematic diagram of a computer system of the foregoing embodiments.
Figure 39:
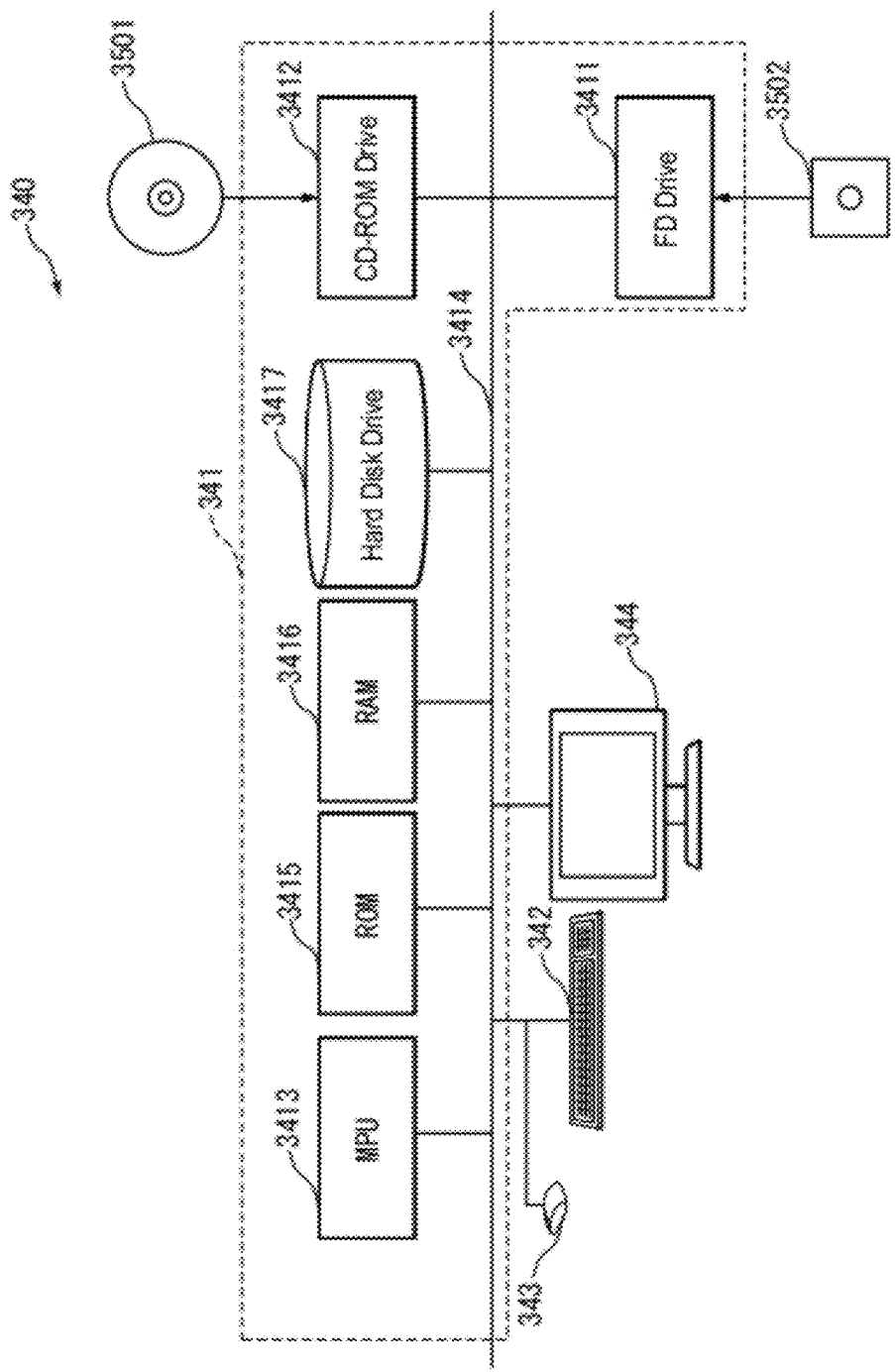
FIG. 39 is a diagram illustrating an internal configuration of the computer system of the foregoing embodiments.

The invention claimed is:

1. An information processing system comprising a terminal apparatus and a server, wherein the terminal apparatus comprises:

a position information acquiring unit that acquires position information that indicates a current position of the terminal apparatus;

an authentication method deciding unit that selects one of two or more authentication methods according to the position information acquired by the position information acquiring unit;

an authentication screen output unit that outputs a screen that corresponds to the one authentication method selected by the authentication method deciding unit;

an accepting unit that accepts authentication information that is input by a user on the screen output by the authentication screen output unit;

an authentication information sending unit that sends, to the server, an authentication method identifier that identifies the authentication method selected by the authentication method deciding unit and the authentication information accepted by the accepting unit;
an output information receiving unit that receives, in a case where an execution result of an authentication unit of the server is success of authentication, from the server, one or more pieces of output information corresponding to the authentication method identification information; and
an output information output unit that outputs the output information, and
the server comprises:
an information storage unit in which two or more pieces of output information that is information to be output are each stored in association with at least one of two or more different authentication methods;
an authentication information receiving unit that receives, from the terminal apparatus, the authentication method identification information and the authentication information;
an authentication unit that performs authentication processing by executing, by using the authentication information received by the authentication information receiving unit, one of the two or more different authentication methods that is identified by the authentication method identification information received by the authentication information receiving unit;
an information acquiring unit that acquires, in a case where an execution result of the authentication unit is success of authentication, one or more pieces of output information corresponding to the authentication method identification information; and
an information sending unit that sends the output information acquired by the information acquiring unit to the terminal apparatus,
wherein the output information is medical record information that includes information that identifies a patient and medical history of the patient, and is associated with at least one authentication method, a doctor identifier that identifies a doctor, and emergency information that indicates an emergency level for performing medical procedure,
the server further comprises a medical procedure information receiving unit that receives, from the terminal apparatus, medical procedure information that includes the doctor identifier or the emergency information that indicates an emergency level for performing medical procedure, and
in a case where the execution result of the authentication unit is success of authentication, the information acquiring unit acquires one or more pieces of output information corresponding to the authentication method identification information and the medical procedure information.

2. The information processing system according to claim 1, wherein the terminal apparatus further comprises:
a terminal identification information storage unit in which terminal identification information can be stored;
an output information storage unit in which output information can be stored;
a non-communication environment detection unit that detects movement to an environment where communication with the server is impossible; and
a sending instruction sending unit that sends, in a case where the non-communication environment detection unit has detected movement to an environment where communication with the server is impossible, a sending instruction including the terminal identification information to the server,
the output information receiving unit receives output information from the server in response to sending of the sending instruction,
the output information output unit accumulates the output information received by the output information receiving unit in the output information storage unit,
the information storage unit of the server has stored therein two or more pieces of output information in association with at least one of the two or more different authentication methods, and has stored therein terminal identification information that identifies the terminal apparatus and output information associated with each other,
the server further comprises a sending instruction receiving unit that receives, from a terminal apparatus, a sending instruction that includes terminal identification information that identifies that terminal apparatus and that is an instruction to send output information, and
in a case where the sending instruction receiving unit has received a sending instruction, the information acquiring unit acquires, from the information storage unit, output information that is paired with the terminal identification information included in that sending instruction.

3. The information processing system according to claim 1, wherein the output information is associated with at least one authentication method and position information that indicates a position,
the server further comprises a terminal position information receiving unit that receives position information that indicates a position of the terminal apparatus from the terminal apparatus, and
in a case where the execution result of the authentication unit is success of authentication, the information acquiring unit acquires one or more pieces of output information corresponding to the authentication method identification information and the position information.

4. The information processing system according to claim 1, wherein the authentication method deciding unit comprises:
a region information storage section in which one or more pieces of region information each of which indicates a region can be stored;
a determination section that determines whether the position that is indicated by the position information acquired by the position information acquiring unit is included in any of one or more regions that are indicated by the one or more pieces of region information stored in the region information storage section; and
an authentication method deciding section that selects one of the two or more authentication methods in a case where the determination section has determined that the position indicated by the position information is included in any of the one or more regions.

5. The information processing system according to claim 4, wherein the two or more authentication methods include a first authentication method and a second authentication method having a security level that is higher than that of the first authentication method, and
in a case where the determination section has determined that the position indicated by the position information is included in any of the one or more regions, the authentication method deciding section selects the first authentication method from among the two or more authentication methods, and in a case where the determination section has determined that the position indicated by the position information is included in none of the one or more regions, the authentication method deciding section selects the second authentication method from among the two or more authentication methods.

6. The information processing system according to claim 4, wherein the region information storage section has stored therein two or more pieces of region authentication information, each piece associating region information with authentication method identification information that identifies the authentication method corresponding to that region information, the determination section determines a region where the position that is indicated by the position information acquired by the position information acquiring unit is included by using the one or more pieces of region information stored in the region information storage section, and the authentication method deciding section acquires, from the region information storage section, the authentication method identification information that is associated with the region information corresponding to the region determined by the determination section.

7. The information processing system according to claim 4, wherein the two or more authentication methods includes a first authentication method and a second authentication method in which authentication processing is not performed, and in a case where the determination section has determined that the position indicated by the position information is included in any of the one or more regions, the authentication method deciding section selects the second authentication method in which authentication processing is not performed, and in a case where the determination section has determined that the position indicated by the position information is included in none of the one or more regions, the authentication method deciding section selects the first authentication method from among the two or more authentication methods.

8. A terminal apparatus that constitutes the information processing system of claim 1.

9. A server that constitutes the information processing system of claim 1.

* * * * *